(12) United States Patent
Hueter et al.

(10) Patent No.: US 10,323,030 B2
(45) Date of Patent: *Jun. 18, 2019

(54) PESTICIDALLY ACTIVE HETEROCYCLIC DERIVATIVES WITH SULPHUR CONTAINING SUBSTITUENTS

(71) Applicant: Syngenta Participations AG, Basel (CH)

(72) Inventors: Ottmar Franz Hueter, Stein (CH); Andrew Edmunds, Stein (CH); Andre Jeanguenat, Stein (CH); Pierre Joseph Marcel Jung, Stein (CH); Anke Buchholz, Stein (CH); Michel Muehlebach, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/536,820

(22) PCT Filed: Dec. 10, 2015

(86) PCT No.: PCT/EP2015/079188
§ 371 (c)(1),
(2) Date: Jun. 16, 2017

(87) PCT Pub. No.: WO2016/096584
PCT Pub. Date: Jun. 23, 2016

(65) Prior Publication Data
US 2017/0342065 A1    Nov. 30, 2017

(30) Foreign Application Priority Data

Dec. 17, 2014 (EP) .................... 14198495

(51) Int. Cl.
| A01N 43/90 | (2006.01) |
| C07D 471/04 | (2006.01) |
| C07D 498/04 | (2006.01) |
| C07D 513/04 | (2006.01) |

(52) U.S. Cl.
CPC .......... *C07D 471/04* (2013.01); *A01N 43/90* (2013.01)

(58) Field of Classification Search
CPC .. C07D 471/04; C07D 498/04; C07D 513/04; A01N 43/90
USPC ...... 548/303.1, 218, 153; 504/276, 270, 266
See application file for complete search history.

(56) References Cited

U.S. PATENT DOCUMENTS

2017/0260182 A1 * 9/2017 Edmunds ............ C07D 471/04

FOREIGN PATENT DOCUMENTS

| WO | 2010125985 A1 | 11/2010 |
| WO | 2011040629 A1 | 4/2011 |
| WO | 2012086848 A1 | 6/2012 |
| WO | 2013018928 A1 | 2/2013 |
| WO | 2013180194 A1 | 12/2013 |
| WO | 2014119494 A1 | 8/2014 |

OTHER PUBLICATIONS

Extended European Search Report for EP14198495, dated Mar. 27, 2015.
International Search Report and Written Opinion for PCT/EP2015/079188, dated Feb. 19, 2016.

* cited by examiner

*Primary Examiner* — Matthew P Coughlin
*Assistant Examiner* — Sagar Patel
(74) *Attorney, Agent, or Firm* — BakerHostetler; Toni-Junell Herbert

(57) ABSTRACT

Compounds of formula (I), wherein the substituents are as defined in claim 1, and the agrochemically acceptable salts, stereoisomers, enantiomers, tautomers and N-oxides of those compounds, can be used as insecticides and can be prepared in a manner known per se.

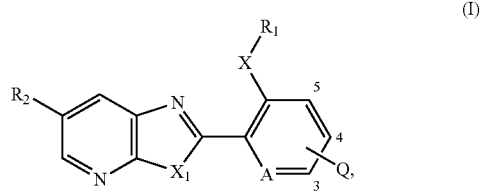

14 Claims, No Drawings

PESTICIDALLY ACTIVE HETEROCYCLIC DERIVATIVES WITH SULPHUR CONTAINING SUBSTITUENTS

RELATED APPLICATION INFORMATION

This application is a 371 of International Application No. PCT/EP2015/079188 filed 10 Dec. 2015, which claims priority to EP 14198495.5 filed 17 Dec. 2014, the contents of which are incorporated herein by reference herein.

The present invention relates to pesticidally active, in particular insecticidally active heterocyclic derivatives containing sulphur substituents, to intermediates for the preparation of those compounds, to compositions comprising those compounds, and to their use for controlling animal pests (including arthropods and in particular insects or representatives of the order Acarina).

Heterocyclic compounds with pesticidal action are known and described, for example, in WO 2012/086848 and WO 2013/018928.

There have now been found novel pesticidally active heterocyclic 6/5-bicyclic ring derivatives with sulphur containing phenyl and pyridyl substituents which are further substituted by a cycloalkyl group.

The present invention accordingly relates to compounds of formula I,

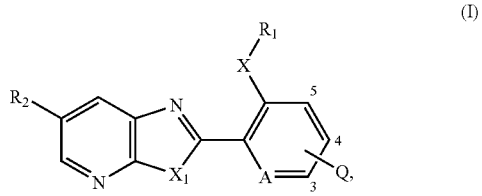

wherein
A represents CH or N;
Q is attached to the 3- or 4-position; and is $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, $C_3$-$C_6$cycloalkyl, —C(O)OH, —C(O)NH$_2$, phenyl and phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and —C(O)$C_1$-$C_4$haloalkyl;
X is S, SO or SO$_2$;
$R_1$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl or $C_3$-$C_6$cycloalkyl mono- or polysubstituted by substituents selected from the group consisting of halogen, cyano and $C_1$-$C_4$alkyl; or
$R_1$ is $C_3$-$C_6$cycloalkyl-$C_1$-$C_4$alkyl mono- or polysubstituted by substituents selected from the group consisting of halogen, cyano and $C_1$-$C_4$alkyl; or
$R_1$ is $C_2$-$C_6$alkenyl, $C_2$-$C_6$haloalkenyl or $C_2$-$C_6$alkynyl;
$R_2$ is halogen, cyano, $C_1$-$C_6$haloalkyl or $C_1$-$C_6$haloalkyl substituted by one or two substituents selected from the group consisting of hydroxyl, methoxy and cyano; or
$R_2$ is $C_1$-$C_4$haloalkylsulfanyl, $C_1$-$C_4$haloalkylsulfinyl, $C_1$-$C_4$haloalkylsulfonyl, O($C_1$-$C_4$haloalkyl), or —C(O)$C_1$-$C_4$haloalkyl; or
$R_2$ is $C_3$-$C_6$cycloalkyl which can be mono- or polysubstituted by substituents selected from the group consisting of halogen, cyano and $C_1$-$C_4$alkyl;
$X_1$ is O, S or NR$_3$, wherein R$_3$ is hydrogen, $C_1$-$C_4$alkyl, $C_2$-$C_6$alkenyl, $C_2$-$C_6$alkynyl, $C_1$-$C_4$alkoxy-$C_1$-$C_4$alkyl or $C_3$-$C_6$cycloalkyl;
and agrochemically acceptable salts, stereoisomers, enantiomers, tautomers and N-oxides of those compounds.

Compounds of formula I which have at least one basic centre can form, for example, acid addition salts, for example with strong inorganic acids such as mineral acids, for example perchloric acid, sulfuric acid, nitric acid, nitrous acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl. In connection with the invention haloalkyl groups are preferably trichloromethyl, difluorochloromethyl, difluoromethyl, trifluoromethyl and dichlorofluoromethyl.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals. In connection with the invention alkoxy groups are preferably methoxy and ethoxy.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkoxycarbonyl is for example methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

Alkylsulfanyl is for example methylsulfanyl, ethylsulfanyl, propylsulfanyl, isopropylsulfanyl, butylsulfanyl, pentylsulfanyl, and hexylsulfanyl.

Alkylsulfinyl is for example methylsulfinyl, ethylsulfinyl, propylsulfinyl, isopropylsulfinyl, a butylsulfinyl, pentylsulfinyl, and hexylsulfinyl.

Alkylsulfonyl is for example methylsulfonyl, ethylsulfonyl, propylsulfonyl, isopropylsulfonyl, butylsulfonyl, pentylsulfonyl, and hexylsulfonyl.

The cycloalkyl groups preferably have from 3 to 6 ring carbon atoms, for example cyclopropyl, cyclobutyl, cyclopentyl and cyclohexyl.

Haloalkoxy groups preferably have a chain length of from 1 to 4 carbon atoms. Haloalkoxy is, for example, difluoromethoxy, trifluoromethoxy or 2,2,2-trifluoroethoxy.

Haloalkylsulfanyl groups preferably have a chain length of from 1 to 4 carbon atoms. Haloalkylsulfanyl is, for example, difluoromethylsulfanyl, trifluoromethylsulfanyl or 2,2,2-trifluoroethylsulfanyl. Similar considerations apply to the radicals $C_1$-$C_4$haloalkylsulfinyl and $C_1$-$C_4$haloalkylsulfonyl, which may be, for example, trifluoromethylsulfinyl, trifluoromethylsulfonyl or 2,2,2-trifluoroethylsulfonyl.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

Free radicals represent methyl groups.

The compounds of formula I according to the invention also include hydrates which may be formed during the salt formation.

Preferably, Q is always in the 4-position and is $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, $C_3$-$C_6$cycloalkyl, phenyl and phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and —C(O)$C_1$-$C_4$haloalkyl.

A preferred group of compounds of formula I is represented by the compounds of formula I-1

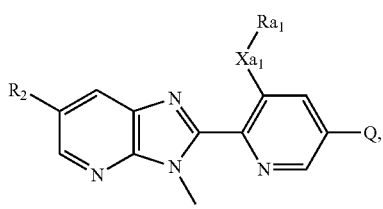

(I-1)

wherein $R_2$ and Q are as defined under formula I above; and wherein $Xa_1$ is S, SO or $SO_2$; $Ra_1$ is methyl, ethyl, n-propyl, i-propyl or cyclopropylmethyl; and agrochemically acceptable salts, stereoisomers, enantiomers, tautomers and N-oxides of those compounds. In said preferred group of compounds of formula I-1, Q is preferably $C_3$-$C_6$cycloalkyl or $C_3$-$C_6$cycloalkyl monosubstituted by substituents selected from the group consisting of cyano, —C(O)OH and —C(O)NH$_2$, in particular Q is $C_3$-$C_6$cycloalkyl or 1-cyanocycloalkyl; $R_2$ is preferably $C_1$-$C_4$haloalkyl; $Xa_1$ is preferably S or $SO_2$ and $Ra_1$ is preferably ethyl. In another preferred group of compounds of formula I-1, Q is preferably $C_3$-$C_6$cycloalkyl or $C_3$-$C_6$cycloalkyl monosubstituted by cyano, —C(O)OH or —C(O)NH$_2$, in particular Q is $C_3$-$C_6$cycloalkyl; $R_2$ is preferably $C_1$-$C_4$haloalkylsulfanyl, $C_1$-$C_4$haloalkylsulfinyl or $C_1$-$C_4$haloalkylsulfonyl; $Xa_1$ is preferably S or $SO_2$ and $Ra_1$ is preferably ethyl.

A further preferred group of compounds of formula I is represented by the compounds of formula I-2

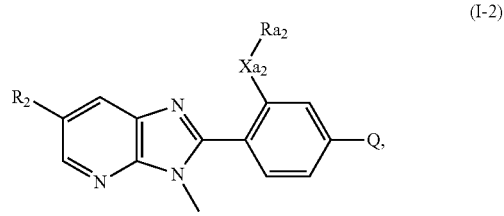

(I-2)

wherein $R_2$ and Q are as defined under formula I above; $Xa_2$ is S, SO or $SO_2$; and $Ra_2$ is methyl, ethyl, n-propyl, i-propyl or cyclopropylmethyl; and agrochemically acceptable salts, stereoisomers, enantiomers, tautomers and N-oxides of those compounds. In this preferred group of compounds of formula I-2, Q is preferably $C_3$-$C_6$cycloalkyl or 1-cyanocycloalkyl; $R_2$ is preferably $C_1$-$C_4$haloalkyl, $Xa_2$ is preferably S or $SO_2$ and $Ra_2$ is preferably ethyl. In another preferred group of compounds of formula I-2, Q is preferably $C_3$-$C_6$cycloalkyl; $R_2$ is preferably $C_1$-$C_4$haloalkylsulfanyl, $C_1$-$C_4$haloalkylsulfinyl or $C_1$-$C_4$haloalkylsulfonyl, $Xa_1$ is preferably S or $SO_2$ and $Ra_1$ is preferably ethyl.

A further preferred group of compounds of formula I is represented by the compounds of formula I-10

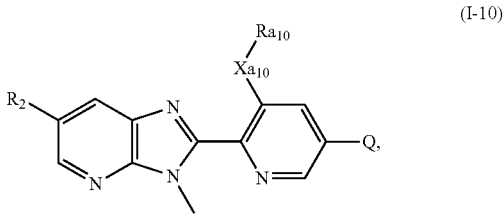

(I-10)

wherein
$R_2$ and Q are as defined under formula I in claim 1;
$Xa_{10}$ is S, SO or $SO_2$; and
$Ra_{10}$ is methyl, ethyl, n-propyl, i-propyl or cyclopropylmethyl.

Preferred compounds of formula I-10 are those, wherein Q is $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, $C_3$-$C_6$cycloalkyl, —C(O)OH, —C(O)NH$_2$ and phenyl, or is phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and —C(O)$C_1$-$C_4$haloalkyl; in particular those wherein Q is $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, or is phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and —C(O)$C_1$-$C_4$haloalkyl.

Even more preferred are those compounds of formula I-10, wherein
Q is $C_3$-$C_6$cycloalkyl, or $C_3$-$C_6$cycloalkyl monosubstituted by substituents selected from the group consisting of cyano, —C(O)OH and —C(O)NH$_2$.

A further preferred group of compounds of formula I is represented by the compounds of formula I-20

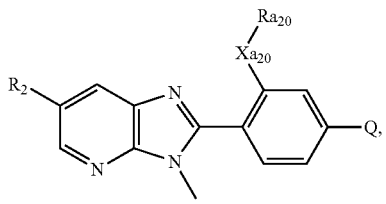

wherein
$R_2$ and Q are as defined under formula I in claim 1;
$Xa_{20}$ is S, SO or SO$_2$; and
$Ra_{20}$ is methyl, ethyl, n-propyl, i-propyl or cyclopropylmethyl.

Preferred compounds of formula I-20 are those, wherein Q is $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, or is phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and —C(O)$C_1$-$C_4$haloalkyl.

Especially preferred compounds of formula I are represented by the compounds of formula Ia-1

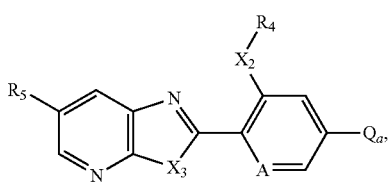

wherein
A is CH or N;
$X_2$ is S or SO$_2$;
$X_3$ is N—($C_1$-$C_4$alkyl);
$R_4$ is $C_1$-$C_4$alkyl;
$R_5$ is $C_1$-$C_4$haloalkyl or $C_1$-$C_4$haloalkylsulfanyl, in particular $C_1$-$C_4$haloalkyl; and
$Q_a$ is $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, —C(O)OH and —C(O)NH$_2$; in particular
$Q_a$ is $C_3$-$C_6$cycloalkyl, or $C_3$-$C_6$cycloalkyl mono- or polysubstituted by substituents selected from the group consisting of halogen, cyano, $C_1$-$C_4$alkyl or $C_1$-$C_4$haloalkyl.

In said preferred compounds of formula Ia-1, $Q_a$ is preferably $C_3$-$C_6$cycloalkyl, or $C_3$-$C_6$cycloalkyl monosubstituted by substituents selected from the group consisting of cyano, —C(O)OH and —C(O)NH$_2$; in particular $Q_a$ is preferably $C_3$-$C_6$cycloalkyl.

An especially preferred group of compounds of formula I are represented by the compounds of formula Ia-2

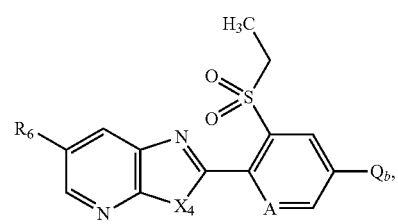

wherein
A is CH or N;
$X_4$ is N—($C_1$-$C_4$alkyl);
$R_6$ is $C_1$-$C_4$haloalkyl or $C_1$-$C_4$haloalkylsulfanyl, in particular $C_1$-$C_4$haloalkyl; and
$Q_b$ is $C_3$-$C_6$cycloalkyl, or $C_3$-$C_6$cycloalkyl monosubstituted by substituents selected from the group consisting of cyano, —C(O)OH and —C(O)NH$_2$; in particular $Q_b$ is $C_3$-$C_6$cycloalkyl.

Another preferred group of compounds of formula I is represented by the compounds of formula I-3

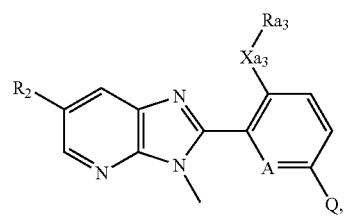

wherein A, $R_2$ and Q are as defined under formula I above; and wherein $Xa_3$ is S, SO or SO$_2$; $Ra_3$ is methyl, ethyl, n-propyl, i-propyl or cyclopropylmethyl; and agrochemically acceptable salts, stereoisomers, enantiomers, tautomers and N-oxides of those compounds. In said preferred group of compounds of formula I-3, Q is preferably $C_3$-$C_6$cycloalkyl or $C_3$-$C_6$cycloalkyl monosubstituted by substituents selected from the group consisting of cyano, —C(O)OH and —C(O)NH$_2$; $R_2$ is preferably $C_1$-$C_4$haloalkyl or $C_1$-$C_4$haloalkylsulfanyl; $Xa_3$ is preferably S or SO$_2$ and $Ra_3$ is preferably ethyl.

A further preferred group of compounds of formula I is represented by the compounds of formula I-30

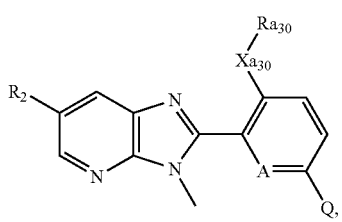

wherein
A, $R_2$ and Q are as defined under formula I in claim 1;
$Xa_{30}$ is S, SO or SO$_2$; and
$Ra_{30}$ is methyl, ethyl, n-propyl, i-propyl or cyclopropylmethyl.

Preferred compounds of formula I-30 are those, wherein Q is $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, $C_3$-$C_6$cycloalkyl, —C(O)OH, —C(O)NH$_2$ and phenyl, or is phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and —C(O)$C_1$-$C_4$haloalkyl.

Even more preferred are those compounds of formula I-30, wherein Q is $C_3$-$C_6$cycloalkyl, or $C_3$-$C_6$cycloalkyl monosubstituted by substituents selected from the group consisting of cyano, —C(O)OH and —C(O)NH$_2$.

Especially preferred compounds of formula I are represented by the compounds of formula Ia-3

(Ia-3)

[Structure of formula Ia-3 with substituents $R_{4p}$, $X_{2p}$, $R_{5p}$, $X_{3p}$, A, $Q_{ap}$]

wherein
A is CH or N, preferably N;
$X_{2p}$ is S or SO$_2$;
$X_{3p}$ is N—($C_1$-$C_4$alkyl);
$R_{4p}$ is $C_1$-$C_4$alkyl;
$R_{5p}$ is $C_1$-$C_4$haloalkyl or $C_1$-$C_4$haloalkylsulfanyl, preferably $C_1$-$C_4$haloalkyl; and
$Q_{ap}$ is $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, —C(O)OH, —C(O)NH$_2$ and phenyl. In said preferred compounds of formula Ia-1, $Q_{ap}$ is preferably $C_3$-$C_6$cycloalkyl, or $C_3$-$C_6$cycloalkyl monosubstituted by substituents selected from the group consisting of cyano, —C(O)OH and —C(O)NH$_2$.

An especially preferred group of compounds of formula I are represented by the compounds of formula Ia-4

(Ia-4)

[Structure of formula Ia-4 with H$_3$C-CH$_2$-S(O)$_2$-, $R_{6p}$, $X_{4p}$, A, $Q_{bp}$]

wherein
A is CH or N, preferably N;
$X_{4p}$ is N—($C_1$-$C_4$alkyl);
$R_{6p}$ is $C_1$-$C_4$haloalkyl or $C_1$-$C_4$haloalkylsulfanyl, preferably $C_1$-$C_4$haloalkyl; and
$Q_{bp}$ is $C_3$-$C_6$cycloalkyl, or $C_3$-$C_6$cycloalkyl monosubstituted by substituents selected from the group consisting of cyano, —C(O)OH and —C(O)NH$_2$.

Even more preferred are those compounds of formula Ia-4, wherein
A is N;
$X_{4p}$ is N—($C_1$-$C_4$alkyl);
$R_{6p}$ is $C_1$-$C_4$haloalkyl; and
$Q_{bp}$ is $C_3$-$C_6$cycloalkyl, or $C_3$-$C_6$cycloalkyl monosubstituted by cyano.

In an outstanding group of compounds of formula I,
$R_1$ is $C_1$-$C_4$alkyl;
$R_2$ is $C_1$-$C_4$haloalkyl or $C_1$-$C_4$haloalkylsulfanyl;
X is S or SO$_2$;
$X_1$ is N—($C_1$-$C_4$alkyl);
A is N;
Q is $C_3$-$C_6$cycloalkyl, or $C_3$-$C_6$cycloalkyl monosubstituted by substituents selected from the group consisting of cyano, —C(O)OH or —C(O)NH$_2$; and Q can be in the 3- or 4-position; and the N-oxides of said outstanding compounds of formula I.

The process according to the invention for preparing compounds of formula I is carried out in principle by methods known to those skilled in the art. The following processes describe the preparation of compounds of formula I, wherein Q is in the 4-position. Compounds of formula I, wherein Q is in the 3-position can be prepared analogously.

More specifically, compounds of formula I can be prepared (as depicted in scheme 1) by reacting compounds of formula II with compounds of formula III, wherein $X_{b1}$ can be a halogen, preferentially chlorine, bromine or iodine, or a sulfonate, like for example a trifluoromethanesulfonate and $Y_{b1}$ can be a boron-derived functional group, as for example B(OH)$_2$ or B(OR$_{b1}$)$_2$ wherein R$_{b1}$ can be a $C_1$-$C_6$alkyl group or the two groups OR$_{b1}$ can form together with the boron atom a five- or six-membered ring, as for example a pinacol boronic ester (Suzuki cross-coupling, see for example Tetrahedron Letters, 43(39), 6987-6990; 2002). In formula II and III, A, $X_1$, $R_1$, $R_2$, X and Q are as described in formula I. The reaction can be catalyzed by a palladium based catalyst, for example tetrakis(triphenylphosphine) palladium(0), bis(triphenylphosphine)palladium(II) dichloride, chloro(2-dicyclohexylphosphino-2',4',6'-triisopropyl-1,1'-biphenyl)[2-(2'-amino-1,1'-biphenyl)]palladium(II) (XPhos palladacycle), (1,1'bis(diphenylphosphino)-ferrocene)dichloropalladium-dichloromethane (1:1 complex) or palladium acetate plus phosphine ligands (such as, for example, triphenylphosphine or tricyclohexylphosphine) in presence of a base, like sodium carbonate, tripotassium phosphate or cesium fluoride, in a solvent (such as toluene, 1,2-dimethoxy-ethane DME, tetrahydrofuran or dioxane) or a solvent mixture, like, for example a mixture of 1,2-dimethoxyethane (or dioxane, toluene, or tetrahydrofuran) and water, preferably under inert atmosphere. The reaction temperature can preferably range from ambient temperature to the boiling point of the reaction mixture, or alternatively heating may be performed under microwave irradiation.

Scheme 1

[Scheme showing compound II with $R_1$, X, $R_2$, $X_1$, A, $Xb_1$ substituents + $Yb_1$—Q (III) → compound I with $R_1$, X, $R_2$, $X_1$, A, Q substituents]

Alternatively, compounds of formula II, wherein $X_{b1}$ can be a halogen, preferentially chlorine, bromine or iodine, or a sulfonate, like for example a trifluoromethanesulfonate, may be reacted with compounds of formula III, wherein $Y_{b1}$ is a magnesium halide group, such as —MgBr (Kumada cross-coupling), optionally in the presence of additives, such as zind halides (Journal of Organic Chemistry, 75(19), 6677-6680; 2010). The reaction may be catalyzed by a palladium based catalyst, or may involve a nickel based catalyst, such as 1,3-is(diphenylphosphino)propanenickel dichloride (dppp)$NiCl_2$.

Also known are reactions between compounds of formula II, wherein $X_{b1}$ can be a halogen, preferentially chlorine, bromine or iodine, or a sulfonate, like for example a trifluoromethanesulfonate, with compounds of formula III, wherein $Y_{b1}$ is a zinc halide group, such as —ZnBr (Negishi cross-coupling), as illustrated for example in Synthetic Communications, 28(2), 225-232; 1998. The reaction may be catalyzed by a palladium based catalyst, such as for example, (1,1'bis(diphenylphosphino)-ferrocene)dichloropalladium Pd(dppf)$Cl_2$ or bis(triphenylphosphine)palladium (II) dichloride, optionally in the presence of phosphine additives (such as, for example, 2-dicyclohexyl-phosphino-2',6'-dimethoxy-biphenyl S-PHOS), in a solvent, like, for example 1,2-dimethoxyethane, dioxane, toluene, or tetrahydrofuran, preferably under inert atmosphere. The reaction temperature can preferentially range from ambient temperature to the boiling point of the reaction mixture.

Compounds of formula I can also be made (as depicted in scheme 2) by reacting compounds of formula IV with compounds of formula V, wherein $X_{b2}$ can be a halogen, preferentially chlorine, bromine or iodine, or a sulfonate, like for example a trifluoromethanesulfonate and $Y_{b2}$ can be a boron-derived functional group, as for example $B(OH)_2$ or $B(OR_{b2})_2$ wherein $R_{b2}$ can be a $C_1$-$C_6$alkyl group or the two groups $OR_{b2}$ can form together with the boron atom a five- or six-membered ring, as for example a pinacol boronic ester. In formula IV and V, A, $X_1$, $R_1$, $R_2$, X and Q are as described in formula I. The reaction can be catalyzed by a palladium based catalyst, for example tetrakis(triphenylphosphine)palladium(0), bis(triphenylphosphine) palladium (II) dichloride or (1,1'bis(diphenylphosphino)-ferrocene)dichloropalladium-dichloromethane (1:1 complex), in presence of a base, like sodium carbonate, tripotassium phosphate or cesium fluoride, in a solvent (such as toluene, 1,2-dimethoxy-ethane DME, tetrahydrofuran or dioxane) or a solvent mixture, like, for example a mixture of 1,2-dimethoxyethane and water, or of dioxane and water, preferably under inert atmosphere. The reaction temperature can preferentially range from ambient temperature to the boiling point of the reaction mixture, or alternatively heating may be performed under microwave irradiation.

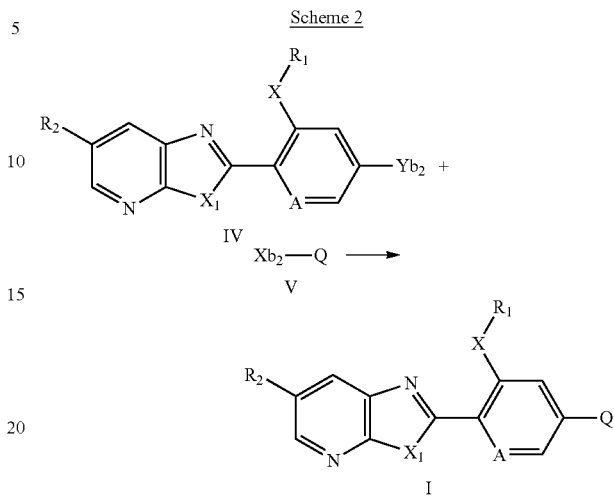

Scheme 2

Compounds of formula I-a3, wherein A, $R_1$, $R_2$, $X_1$ and Q have the values defined in formula I, and X is —$SO_2$—, can be prepared by oxidation of compounds of formula I-a2, wherein A, $R_1$, $R_2$, $X_1$ and Q have the values defined in formula I, and X is —SO—. The reaction can be performed with reagents like, for example, a peracid such as peracetic acid or m-chloroperbenzoic acid, or a hydroperoxide, as for example, hydrogen peroxide or tert-butylhydroperoxide, or an inorganic oxidant, like a monoperoxo-disulfate salt or potassium permanganate. In a similar way, compounds of formula I-a2, wherein A, $R_1$, $R_2$, $X_1$ and Q have the values defined in formula I, and X is —SO—, can be prepared by oxidation of compounds of formula I-a1, wherein A, $R_1$, $R_2$, $X_1$ and Q have the values defined in formula I, and X is —S—, under analogous conditions described above. These reactions can be performed in various organic (dichloromethane for example) or aqueous solvents compatible to these conditions, by temperatures from below 0° C. up to the boiling point of the solvent system. The transformation of compounds of the formula 1-a1 into compounds of the formula 1-a2 and 1-a3 is represented in scheme 3.

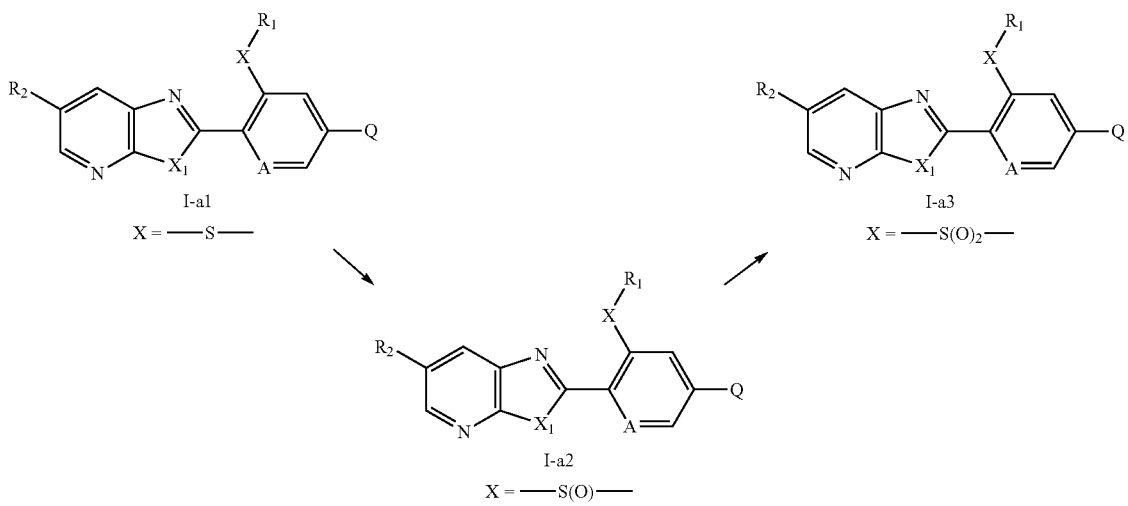

Scheme 3

Compounds of formula I-a1 may also be prepared (scheme 4) by reacting a compound of the formula VI with a compound of the formula VII, wherein A, $R_1$, $R_2$, $X_1$ and Q have the values defined in formula I and X is sulphur and M is a metal or non-metal cation. In the scheme 4, the cation M is assumed to be monovalent, but polyvalent cations associated with more than one S—$R_1$ group can also be considered. Preferred cations are, for example lithium, sodium, potassium or cesium. For this transformation to work, $Xb_3$ is a leaving group like, for example, fluorine, chlorine, bromine or iodine, or an aryl- or alkylsulfonate, but many other leaving groups could be considered. The reaction can be performed in a solvent, preferably aprotic (such as N,N-dimethylformamide or acetonitrile), at temperatures below 0° C. or up to the boiling temperature of the reaction mixture.

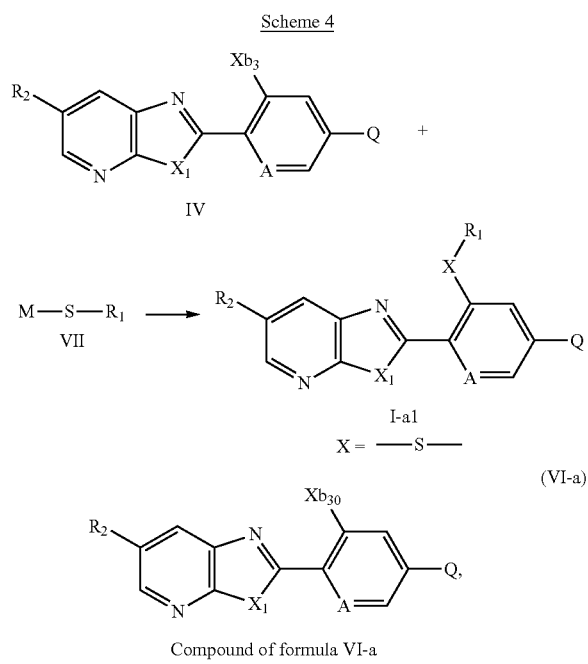

wherein
A, Q, $X_1$ and $R_2$ are as defined under formula I in claim 1; and
$Xb_{30}$ is halogen;
are novel and especially developed for the preparation of the compounds according to the present invention. The compounds of formula VI-a therefore constitute a further object of the invention.

Compounds of formula VI, wherein $Xb_3$ is a leaving group like, for example, fluorine, chlorine, bromine or iodine, or an aryl- or alkylsulfonate such as trifluoromethanesulfonate, or any other similar leaving group, can be prepared (scheme 5) by reacting compounds of formula VIII with compounds of formula IX, wherein $X_{b4}$ can be a halogen, preferentially chlorine, bromine or iodine, or a sulfonate, like for example a trifluoromethanesulfonate, most preferably bromine or iodine and $Y_{b4}$ can be a boron-derived functional group, as for example $B(OH)_2$ or $B(OR_{b4})_2$ wherein $R_{b4}$ can be a $C_1$-$C_6$alkyl group or the two groups $OR_{b4}$ can form together with the boron atom a five- or six-membered ring, as for example a pinacol boronic ester. In formula VI, VIII and IX, A, $X_1$, $R_2$ and Q are as described in formula I. The reaction can be catalyzed by a palladium based catalyst, for example tetrakis(triphenylphosphine)palladium(0), bis(triphenylphosphine) palladium (II) dichloride or (1,1'bis(diphenyl-phosphino)-ferrocene) dichloropalladium-dichloromethane (1:1 complex), in presence of a base, like sodium carbonate, tripotassium phosphate or cesium fluoride, in a solvent (such as toluene, 1,2-dimethoxy-ethane DME, tetrahydrofuran or dioxane) or a solvent mixture, like, for example a mixture of 1,2-dimethoxyethane and water, or of dioxane and water, preferably under inert atmosphere. The reaction temperature can preferentially range from ambient temperature to the boiling point of the reaction mixture, or alternatively heating may be performed under microwave irradiation.

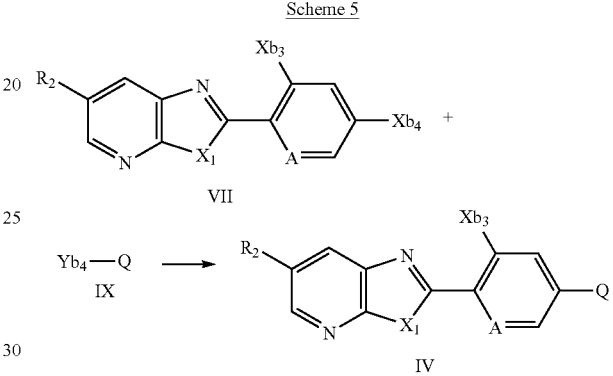

Alternatively, compounds of formula VIII, wherein $X_{b4}$ can be a halogen, preferentially chlorine, bromine or iodine, or a sulfonate, like for example a trifluoromethanesulfonate, may be reacted with compounds of formula IX, wherein $Y_{b4}$ is a magnesium halide group, such as —MgBr (Kumada cross-coupling), optionally in the presence of additives, such as zind halides (Journal of Organic Chemistry, 75(19), 6677-6680; 2010). The reaction may be catalyzed by a palladium based catalyst, or may involve a nickel based catalyst, such as 1,3-is(diphenylphosphino)propanenickel dichloride (dppp)NiCl$_2$.

Also known are reactions between compounds of formula VIII, wherein $X_{b4}$ can be a halogen, preferentially chlorine, bromine or iodine, or a sulfonate, like for example a trifluoromethanesulfonate, with compounds of formula IX, wherein $Y_{b4}$ is a zinc halide group, such as —ZnBr (Negishi cross-coupling), as illustrated for example in Synthetic Communications, 28(2), 225-232; 1998. The reaction may be catalyzed by a palladium based catalyst, such as for example, (1,1'bis(diphenylphosphino)-ferrocene)dichloropalladium Pd(dppf)C$_2$ or bis(triphenylphosphine)palladium (II) dichloride, optionally in the presence of phosphine additives (such as, for example, 2-dicyclohexyl-phosphino-2',6'-dimethoxy-biphenyl S-PHOS), in a solvent, like, for example 1,2-dimethoxyethane, dioxane, toluene, or tetrahydrofuran, preferably under inert atmosphere. The reaction temperature can preferentially range from ambient temperature to the boiling point of the reaction mixture.

In an alternative way depicted in scheme 6, compounds of formula VI can also be prepared by reacting compounds of formula X, wherein $Xb_3$ is a leaving group like, for example, fluorine, chlorine, bromine or iodine, or an aryl- or alkylsulfonate such as trifluoromethanesulfonate, or any other similar leaving group, with compounds of formula XI, wherein $X_{b5}$ can be a halogen, preferentially chlorine, bromine or iodine, or a sulfonate, like for example a trifluoromethanesulfonate, most preferably bromine or iodine, and $Y_{b5}$ can be a boron-derived functional group, as for example $B(OH)_2$ or $B(OR_{b5})_2$ wherein $R_{b5}$ can be a $C_1$-$C_6$alkyl group or the two groups $OR_{b5}$ can form together with the boron atom a five- or six-membered ring, as for example a pinacol boronic ester. In formula VI, X and XI, A, $X_1$, $R_2$ and Q are as described in formula I. The reaction can be catalyzed by a palladium based catalyst, for example tetrakis(triphenylphosphine)palladium(0), bis(triphenylphosphine) palladium (II) dichloride or (1,1'bis(diphenylphosphino)-ferrocene)dichloropalladium-dichloromethane (1:1 complex), in presence of a base, like sodium carbonate, tripotassium phosphate or cesium fluoride, in a solvent (such as toluene, 1,2-dimethoxy-ethane DME, tetrahydrofuran or dioxane) or a solvent mixture, like, for example a mixture of 1,2-dimethoxyethane and water, or of dioxane and water, preferably under inert atmosphere. The reaction temperature can preferentially range from ambient temperature to the boiling point of the reaction mixture, or alternatively heating may be performed under microwave irradiation.

Scheme 6

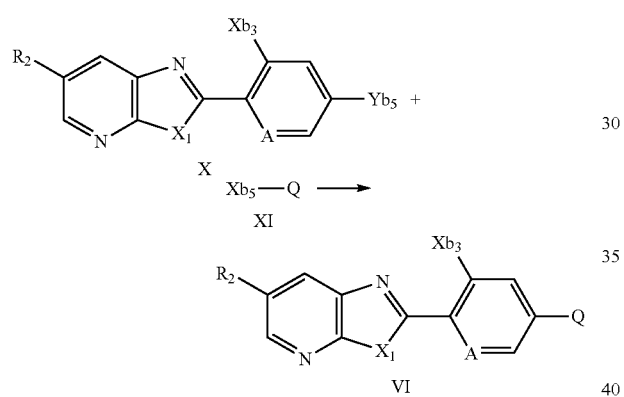

Compounds of formula I can also be prepared (scheme 7) by reacting compounds of formula XIII and compounds of formula XIV under various formal dehydration conditions, wherein A, $R_1$, $R_2$, X, $X_1$ and Q have the values defined in formula I. These methods are known to those skilled in the art or described for example in WO 2009/131237, WO 2011/043404, WO 2011/040629, WO 2010/125985, WO 2012/086848, WO 2013/018928, WO 2013/191113, WO 2013/180193 and WO 2013/180194. Such processes are well known and have been described for example in WO 2011/040629 or WO 2009131237 ($X_1$ is oxygen), WO 2011088990 or *Inorg. Chimica Acta*, 358(9), 2701-2710; 2005 ($X_1$ is sulfur) and *J. Am. Chem. Soc.*, 132(5), 1545-1557, 2010 or WO 2008128968 ($X_1$ is $NR_3$). Compounds of formula XIII are either commercial or have been described, for example, in WO 2012/086848.

Scheme 7

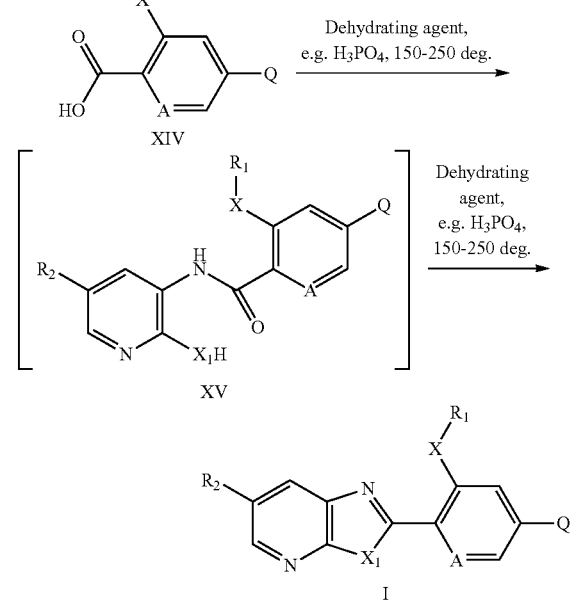

The process describing the reaction between compounds of formula XIII and compounds of formula XIV towards compounds of formula I is summarized in more details in scheme 8:

Scheme 8

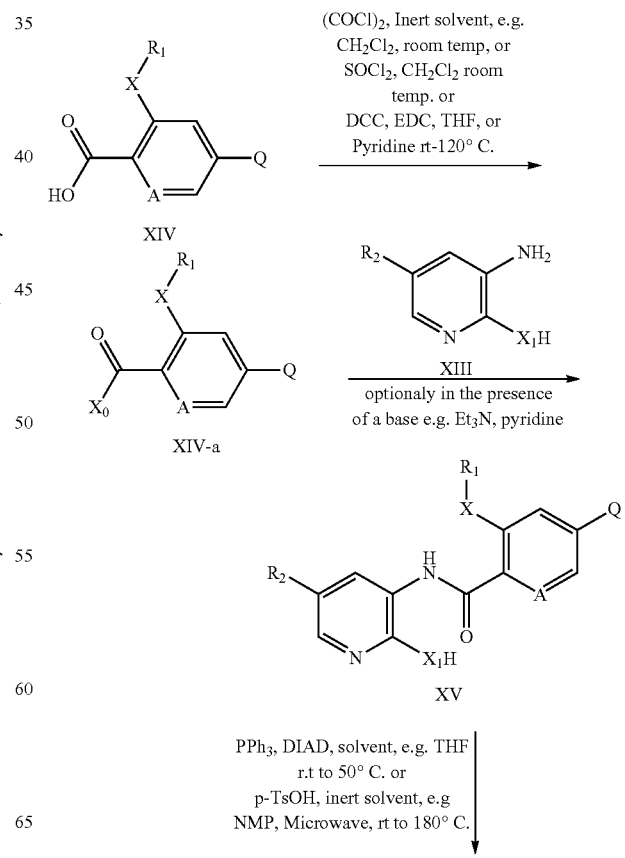

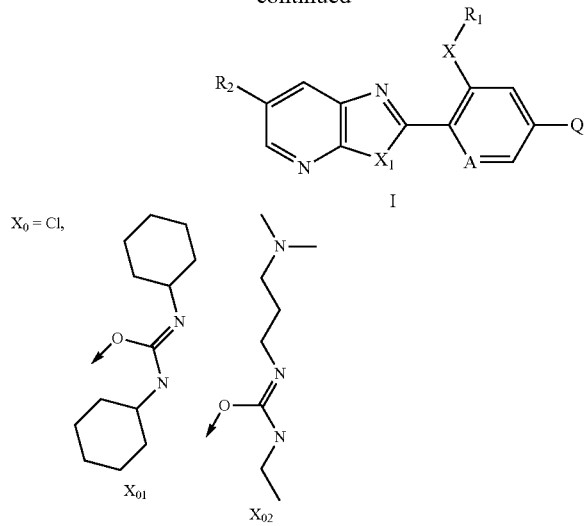

Compounds of formula XIV, wherein A, $R_1$, X and Q are as previously described, are activated (scheme 8) to compounds of formula XIV-a by methods known to those skilled in the art and described in for example Tetrahedron, 61 (46), 10827-10852, 2005. For example compounds where $X_0$ is chlorine are formed by treatment with for example, oxalyl chloride or thionyl chloride in the presence of catalytic quantities of DMF in inert solvents such as methylene chloride or THF at temperatures between 20° C. to 100° C., preferably 25° C. Treatment of XIV-a with compounds of formula XIII, wherein $R_2$ and $X_1$ are as described in formula I, optionally in the presence of a base, e.g. triethylamine or pyridine, leads to compounds of formula XV. Alternatively, compounds of formula I can be prepared by treatment of compounds of formula XIV with dicyclohexyl carbodiimide (DCC) or 1-ethyl-3-(3-dimethylaminopropyl)carbodiimide (EDC) to give the activated species XIV-a, wherein $X_0$ is $X_{01}$ and $X_{02}$ respectively, in an inert solvent, e.g. pyridine, or tetrahydrofuran (THF) optionally in the presence of a base, e.g. triethylamine, at temperatures between 50-180° C. Compounds of formula XV so obtained can then be converted to compounds of formula I by dehydration, eg. by heating the compounds, optionally under microwave irradiation, in the presence of an acid catalyst, for example methanesulfonic acid, or para-toluenesulfonic acid p-TsOH, in an inert solvent such as N-methyl pyrrolidone or xylene, at temperatures between 25-180° C., preferably 130-170° C. Such processes have been described previously in WO 2010/125985. Alternatively, compounds of formula XV can be converted to compounds of formula I (wherein $X_1$ is O) using triphenylphosphine, di-isopropyl azodicarboxylate in an inert solvent such as THF at temperatures between 25-50° C. Such Mitsunobu conditions have been previously described for such transformations (see WO 2009/131237).

In an analogous way (scheme 9), compounds of formula VI, wherein $Xb_3$ is a leaving group like, for example, fluorine, chlorine, bromine or iodine, or an aryl- or alkyl-sulfonate such as trifluoromethane-sulfonate, or any other similar leaving group, can be prepared by reacting compounds of formula XVI,

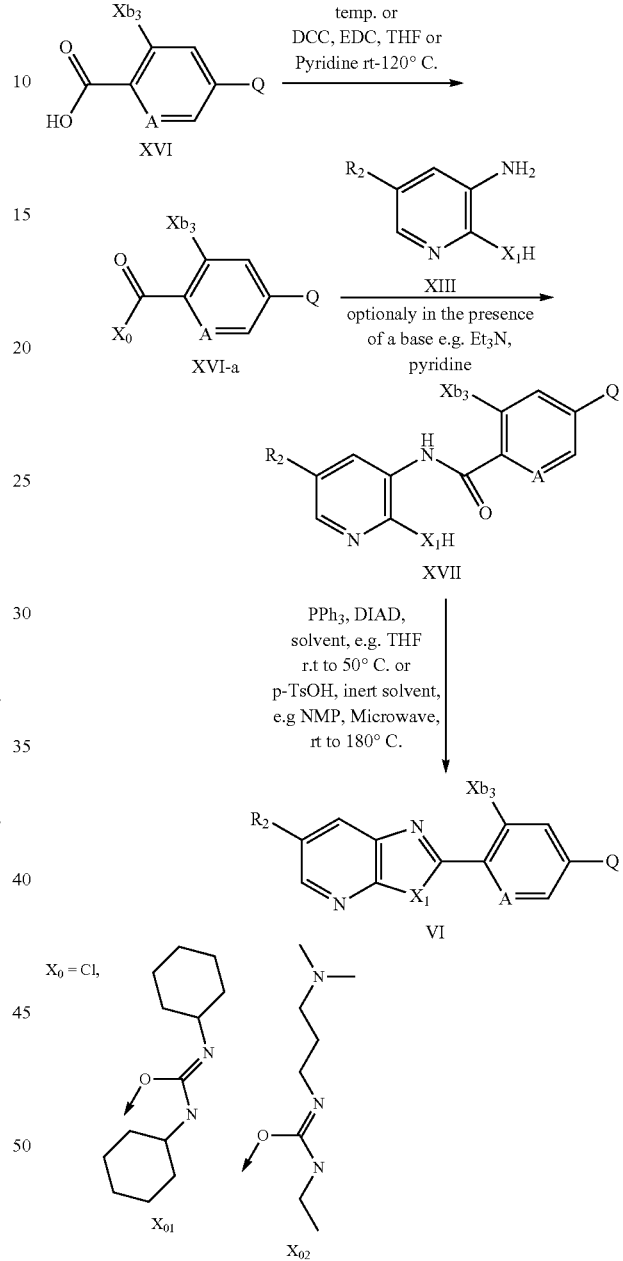

wherein A and Q have the values defined for formula I, with an activating agent, like, for example oxalyl chloride or thionyl chloride or a carbodiimid reagent to generate the activated species XVI-a, followed by reaction with compounds of formula XIII, wherein $R_2$ and $X_1$ are as described in formula I. The intermediate compounds of formula XVII may be isolated, but are preferentially converted into the compounds of formula VI in a similar way as described above for the transformation of compounds XV into compounds of formula I.

In a similar way as described above, compounds of formula VIII can be prepared as described in scheme 10,

Scheme 10

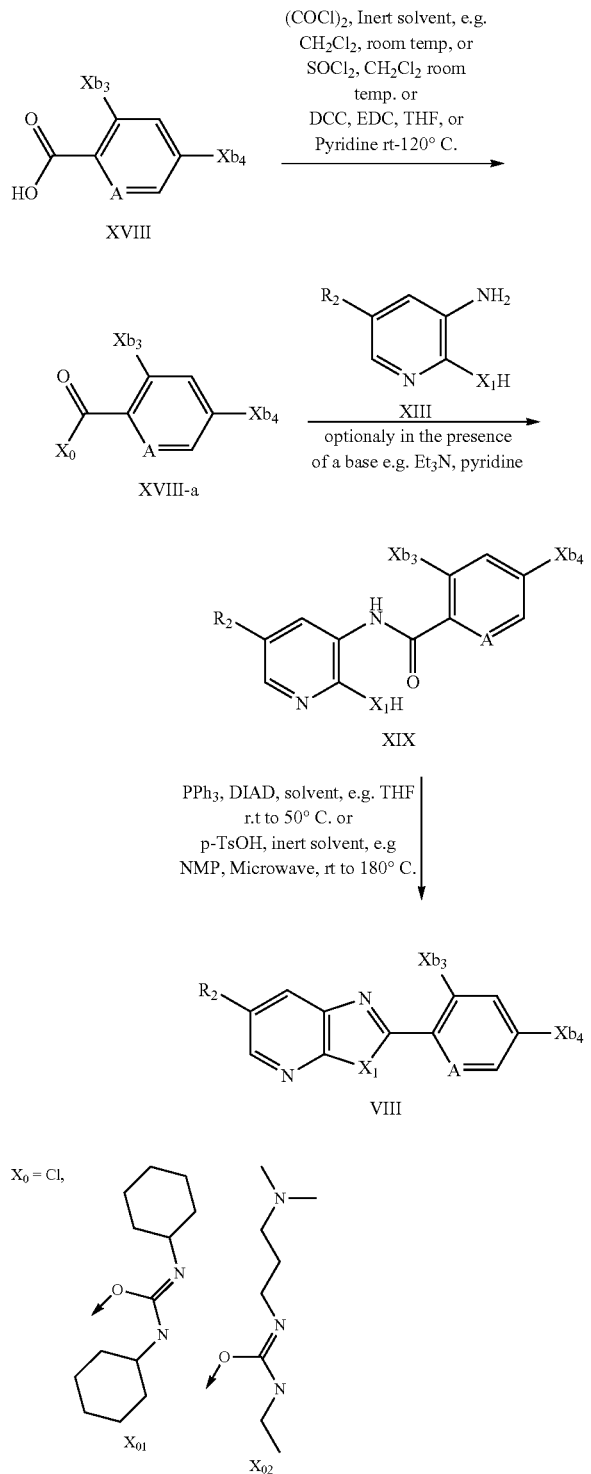

by reacting compounds of formula XVIII, respectively an activated form XVIII-a of compounds of formula XVIII, wherein A is carbon or nitrogen, and $X_{b3}$ is a leaving group like, for example fluorine, chlorine, bromine or iodine, or an aryl- or alkylsulfonate such as trifluoromethane-sulfonate, and $X_{b4}$ can be a halogen, preferentially chlorine, bromine or iodine, or a sulfonate, like for example a trifluoromethanesulfonate, most preferably bromine or iodine, with compounds of the formula XIII, wherein $X_1$ and $R_2$ are as defined in formula I. The intermediate compounds of formula XIX may be isolated, but are preferentially converted into the compounds of formula VIII in a similar way as described above (transformation of compounds XV into compounds of formula I).

Compounds of formula XXI can be prepared as described in scheme 10a, by reacting compounds of formula XX, wherein A is CH or nitrogen, and $X_{b3}$ is a leaving group like, for example nitro, fluorine, chlorine, bromine or iodine, or an aryl- or alkylsulfonate such as trifluoromethanesulfonate, and $X_{b4}$ can be a halogen, preferentially chlorine, bromine or iodine, or a sulfonate, like for example a trifluoromethanesulfonate, most preferably bromine or iodine, with a compound of formula VII, wherein $R_1$ is as defined in formula I, and M is a metal or non-metal cation. In scheme 10a, the cation M is assumed to be monovalent, but polyvalent cations associated with more than one S—$R_1$ group can also be considered. Preferred cations are, for example lithium, sodium, potassium or cesium. The reaction can be performed in a solvent, preferably polar aprotic, such as THF, N,N-dimethylformamide or MeCN, at temperatures between −78° C. and the boiling temperature of the reaction mixture. Compounds of formula XVIII-c can be prepared by hydrolysis of compounds of formula XXI under acidic (e.g. HCl or $H_2SO_4$) or basic conditions (e.g. NaOH or KOH) as described in scheme 10a, under conditions known to a person skilled in the art. Compounds of formula II-a1 can be prepared, as described in scheme 10a, by reacting compounds of formula XVIII-c respectively an activated form XVIII-d of compounds of formula XVIII-c with compounds of formula XIII, wherein $X_1$ and $R_2$ are as defined in formula I. The intermediate compounds of formula XXII may be isolated, but are preferentially converted into the compounds of formula II-a1 in a similar way as described above (transformation of compounds XV into compounds of formula I). In compounds of formula XXI, XVIII-c, XVIII-d, XXII and II-a1, X can be S, SO or $SO_2$ (when X is SO, compounds of formula II-a1 become compounds of formula II-a2; respectively, when X is $SO_2$, compounds of formula II-a1 become compounds of formula II-a3; see scheme 12). The appropriate oxidation forms of the sulfur atom in compounds of formula XXI, XVIII-c, XVIII-d, XXII and II-a1 wherein X is SO or $SO_2$, can be prepared by oxidation of compounds of formula XXI, XVIII-c, XVIII-d, XXII and II-a1 wherein X is S. The reaction can be performed with reagents like, for example a peracid as peracetic acid or m-chloroperbenzoic acid, or a hydroperoxide as for example hydrogen peroxide or tert-butylhydroperoxide, or an inorganic oxidant, like a mono-peroxodisulfate salt or potassium permanganate, preferentially meta-chloroperbenzoic acid as described before.

Scheme 10a

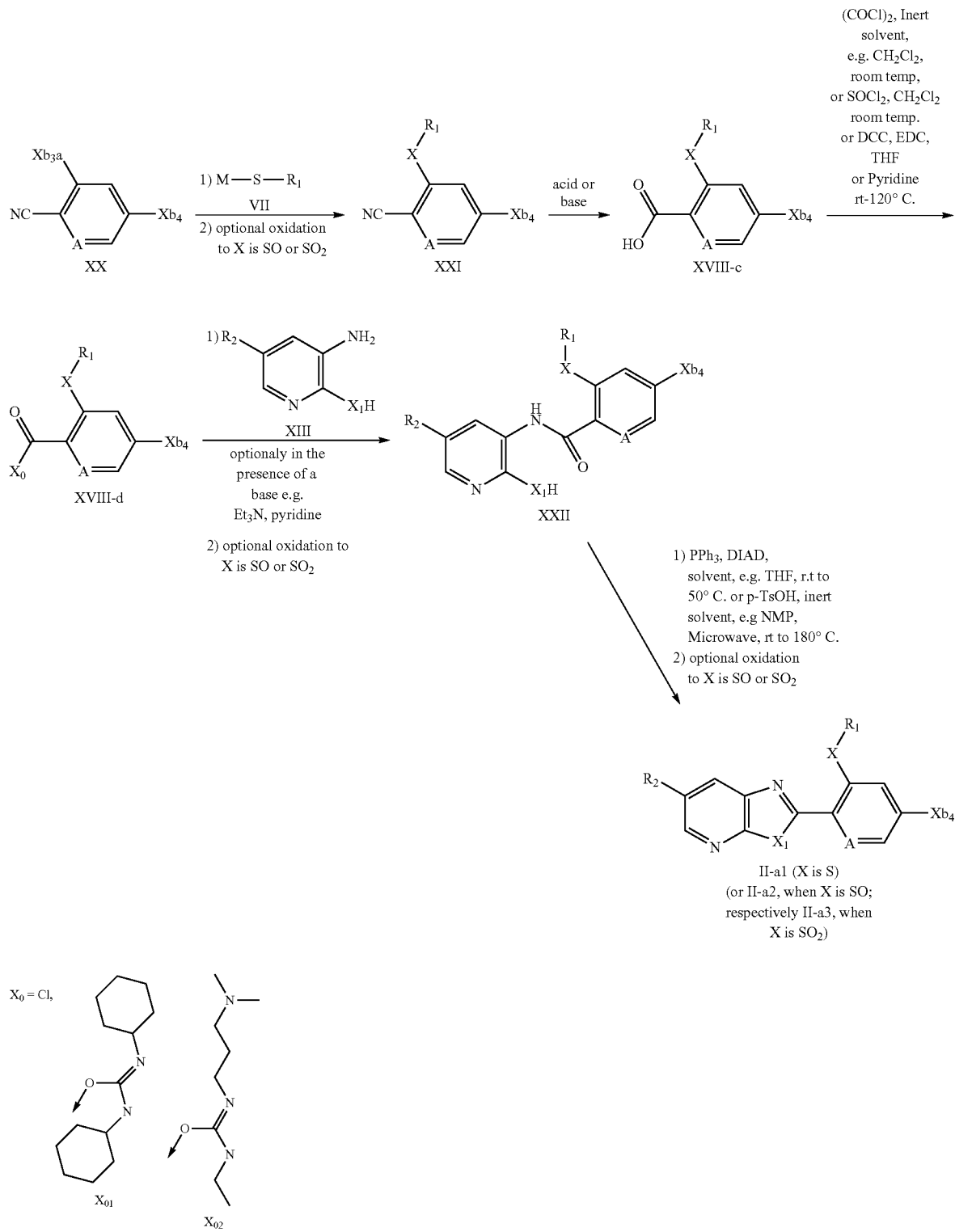

Compounds of formula XVIII-c, wherein X is S, SO or SO$_2$, can alternatively be prepared by analogous methods to those described in the literature (scheme 10b). For example, a compound of formula XVIII-c, wherein X is S, may be prepared by saponification of a compound of formula XXIV, wherein R$_{LG}$ is C$_1$-C$_4$alkyl, under conditions known to a person skilled in the art (R$_1$ is as defined in formula I, A is N or CH, and X$_{b4}$ can be a halogen, preferentially chlorine, bromine or iodine, or a sulfonate, like for example a trifluoromethanesulfonate, most preferably bromine or iodine).

Scheme 10b

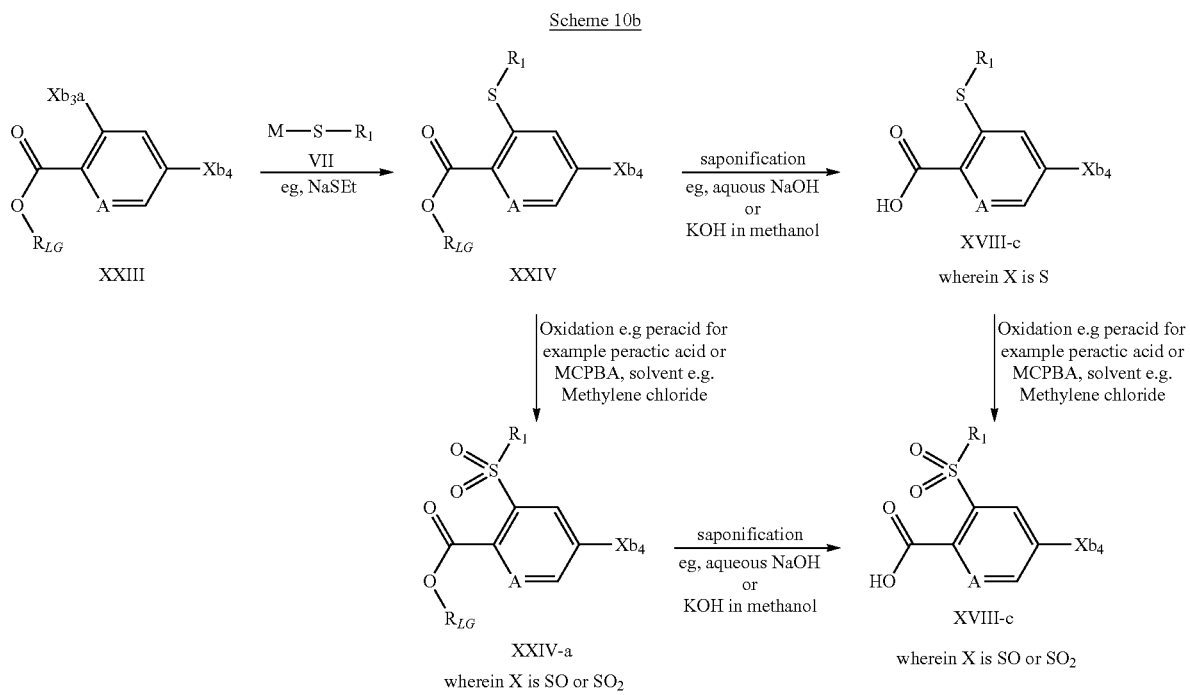

wherein $R_1$ is for example ethyl,
$Xb_4$ is for example bromine,
$Xb_3a$ is for example fluorine or chlorine,
$R_{LG}$ is for example methyl,
A is N or CH.

Compounds of formula XXIV, wherein $R_{LG}$ is $C_1$-$C_4$alkyl, may be prepared by treatment of compounds of formula XXIII, wherein $Xb_3a$ is a leaving group like, for example nitro, fluorine, chlorine, bromine or iodine, or an aryl- or alkylsulfonate such as trifluoromethanesulfonate, and wherein $R_{LG}$ is $C_1$-$C_4$alkyl, with a reagent M-S—$R_1$ of formula VII, wherein $R_1$ is as defined in formula I and M is a metal or non-metal cation, under conditions described above. Such processes involving for example sodium methane- or ethanethiolate as reagents M-S—$R_1$ are well known and have been described previously in, for example, WO2014/152738. Compounds of formula XXIV can be oxidised to compounds of formula XXIV-a using methods known to those skilled in the art and described for example in Scheme 12, and then saponified to compounds of formula XVIII-c, wherein X is SO or $SO_2$. Alternatively compounds of formula XXIV can be first saponified to compounds of formula XVIII-c, wherein X is S, and then oxidised to compounds of formula XVIII-c, wherein X is SO or $SO_2$. Compounds of formula XXIII are either commercial or have been described in WO 2012/086848.

Changing order of reaction conditions that have been described above may also allow to convert compounds of the formula XVIII-c, or their activated form XVIII-d, into useful compounds of the formula XXIV, or their oxidized form XXIV-a. This is illustrated in scheme 10c.

Scheme 10c:

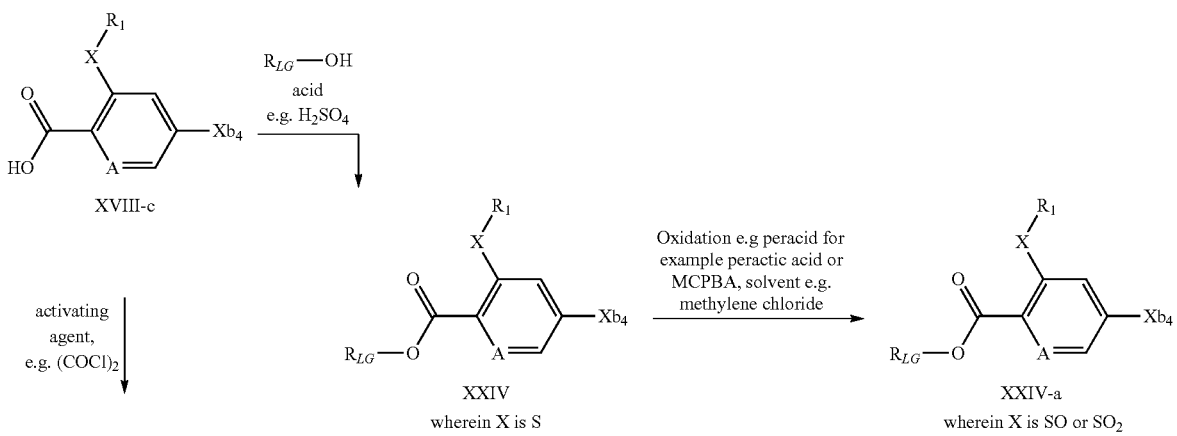

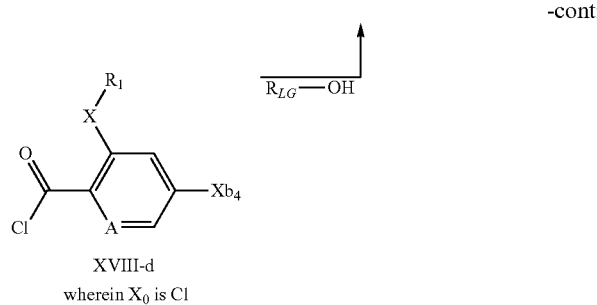

XVIII-d wherein $X_0$ is Cl

As described in scheme 10c, ester compounds of formula XXIV, wherein X is S and $R_{LG}$ is $C_1$-$C_4$alkyl, may be prepared from the corresponding carboxylic acid compounds of formula XVIII-c, wherein X is S, by reaction with an alcohol of formula $R_{LG}OH$, wherein $R_{LG}$ is $C_1$-$C_4$alkyl, optionally in the presence of an acid (such as sulfuric acid), or alternatively optionally in presence of an activating agent, such as for example oxalyl chloride $(COCl)_2$. Such esterification methods are well known to a person skilled in the art and described in the literature. Compounds of formula XXIV can be oxidised to compounds of formula XXIV-a as discussed in scheme 10b. The substituent definitions in compounds of formula XVIII-c, XVIII-d, XXIV and XXIV-a are as previously described.

Compounds of formula II-a1, wherein X is sulfur, can be prepared (scheme 11) by reacting a compound of the formula VIII, wherein A, $R_2$ and $X_1$ are as defined in formula I, and wherein $X_{b3}$ is a leaving group like, for example, fluorine, chlorine, bromine or iodine, or an aryl- or alkyl-sulfonate such as trifluoromethanesulfonate, preferentially fluorine or chlorine, and wherein $X_{b4}$ is a halogen, preferentially chlorine, bromine or iodine, or a sulfonate, like for example a trifluoromethanesulfonate, most preferably bromine or iodine, with a compound of the formula VII, wherein $R_1$ is as defined in formula I, and M is a metal or non-metal cation. In scheme 11, the cation M is assumed to be monovalent, but polyvalent cations associated with more than one S—$R_1$ group can also be considered. Preferred cations are, for example lithium, sodium, potassium or cesium. The reaction can be performed in a solvent, preferably polar aprotic, at temperatures below 0° C. or up to boiling temperature of the reaction mixture.

Scheme 11

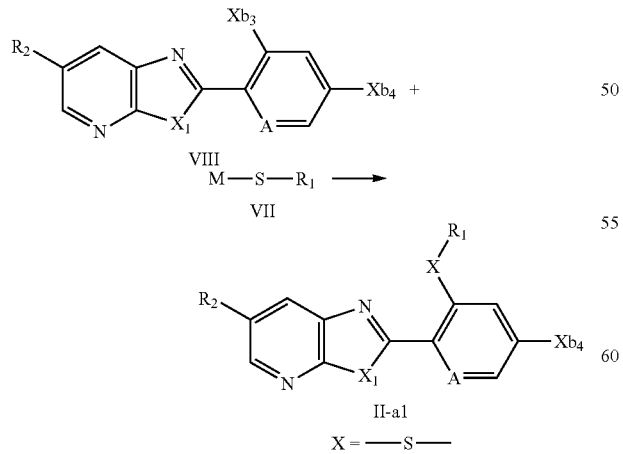

Compounds of formula II-a3, wherein A, $R_1$, $R_2$ and $X_1$ have the values defined in formula I, and X is —$SO_2$—, and wherein $X_{b4}$ is a halogen, preferentially chlorine, bromine or iodine, or a sulfonate, like for example a trifluoromethane-sulfonate, can be prepared (scheme 12) by oxidation of compounds of formula II-a2, wherein A, $R_1$, $R_2$ and $X_1$ have the values defined in formula I, and X is —SO—, and wherein $X_{b4}$ is a halogen, preferentially chlorine, bromine or iodine, or a sulfonate, like for example a trifluoromethane-sulfonate. The reaction can be performed with reagents like, for example a peracid as peracetic acid or m-chloroperbenzoic acid, or a hydroperoxide as for example hydrogen peroxide or tert-butylhydroperoxide, or an inorganic oxidant, like a mono-peroxodisulfate salt or potassium permanganate, preferentially meta-chloroperbenzoic acid. In a similar way, compounds of formula II-a2, wherein A, $R_1$, $R_2$ and $X_1$ have the values defined in formula I, and X is —SO—, and wherein $X_{b4}$ is a halogen, preferentially chlorine, bromine or iodine, or a sulfonate like for example a trifluoromethane-sulfonate, can be prepared by oxidation of compounds of formula II-a1, wherein A, $R_1$, $R_2$ and $X_1$ have the values defined in formula I, and X is —S—, and wherein $X_{b4}$ is a halogen, preferentially chlorine, bromine or iodine, or a sulfonate, like for example a trifluoromethanesulfonate. These reactions can be performed in various organic or aqueous solvents compatible to these conditions, by temperatures from below 0° C. up to the boiling point of the solvent system.

Scheme 12

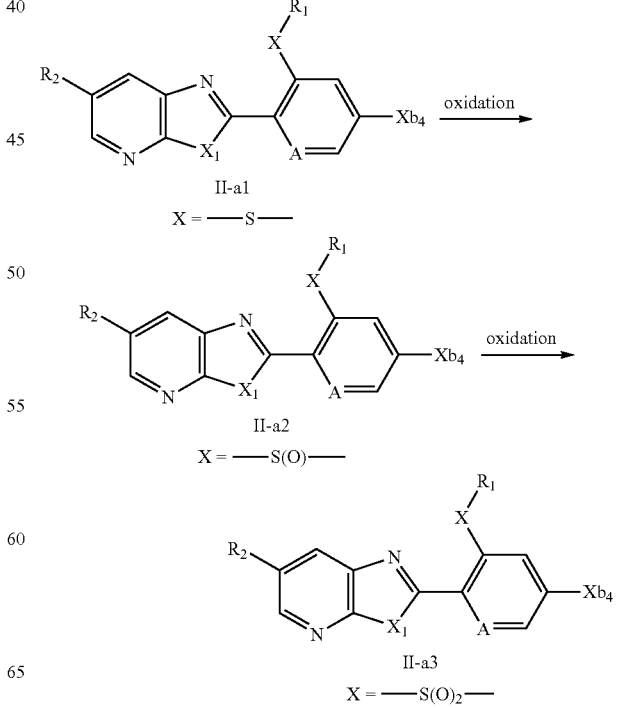

Many compounds of the formula V and XI, wherein Q has the values defined in formula I, and wherein $X_{b2}$ and $X_{b5}$ are as defined above, are commercially available or can be accessible to the person skilled in the art, by analogy to procedures described in the literature.

A large number of compounds of the formula III are commercially available or can be prepared by those skilled in the art. Many chemical transformations, well known by those skilled in the art, can be used to access boronic acid derivatives of formula III, starting from various and easily available starting materials, as for example, to cite only a few (scheme 13), hydrogen abstraction on a compound of the formula III-a wherein $Zb_1$ is hydrogen, with a strong base (step A), like butyllithium or lithium diisopropylamide or (i-PrMgCl, LiCl), followed by reaction of the metallated intermediate of the formula III-b, wherein $Zb_2$ is a metal such as $Li^+$ or $MgCl^+$ for example, with, for example, a trialkylborate (step B). Another way to access an organo-metal intermediate of the formula III-b is from a compound of the formula III-a wherein $Zb_1$ is chlorine, bromine or iodine, via metal-halogen exchange with an organometallic species (step C), like butyllithium or an organomagnesium compound, or direct metallation with a metal, like magnesium.

Introduction of a pinacolborate functional group via a palladium catalyzed reaction with bispinacol diborane on a compound of the formula III-a, wherein $Zb_1$ is chlorine, bromine, iodine or triflate, is another common strategy (scheme 13, step D). In the compounds of formula III-a, III-b and III within scheme 13, Q has the values defined for the formula I. A person skilled in the art will be able to select an adequate preparation method to access compounds of formula III from III-a depending on the values of Q.

Compounds of formula IV, wherein A, X, $X_1$, $R_1$ and $R_2$ are as described in formula I, can be prepared from compounds of formula II (scheme 14), wherein A, X, $X_1$, $R_1$ and $R_2$ are as described in formula I. Indeed, compounds of formula II, wherein $Xb_1$ is chlorine, bromine or iodine, can be treated with an organometallic species like, for example, butyllithium or an organomagnesium compound, to generate an intermediate compound of the formula II-a, wherein $Zb_3$ is as defined in the scheme, via metal-halogen exchange. This reaction is preferentially performed in an anhydrous aprotic solvent, such as THF, at low temperature (between −120° C. and 0° C.), preferentially between −110° C. and −60° C.). The intermediate organometal compound of formula II-a is preferably directly converted into compound of formula IV by reaction with a boronate compound $B(OR_{b2})_3$, wherein $R_{b2}$ is a $C_1$-$C_6$alkyl group. Depending on the nature of the boronate, the reaction treatment conditions and the workup conditions, the boronic acid IV, wherein $Yb_2$ is —$B(OH)_2$, or a dialkylboronate IV, wherein $Yb_2$ is —$B(OR_{b2})_2$, can be formed.

Introduction of a pinacolborate functional group via a palladium catalyzed reaction with bispinacol diborane $B_2Pin_2$ on a compound of the formula II, wherein A, X, $X_1$, $R_1$ and $R_2$ are as described in formula I, and wherein $Xb_1$ is chlorine, bromine, iodine or triflate, is another common strategy. This reaction, generating a cyclic boronate IV, wherein $Yb_2$ is

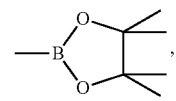

can be performed in an aprotic solvent, in presence of a base, preferentially a weak base, such as potassium acetate KOAc.

Scheme 13

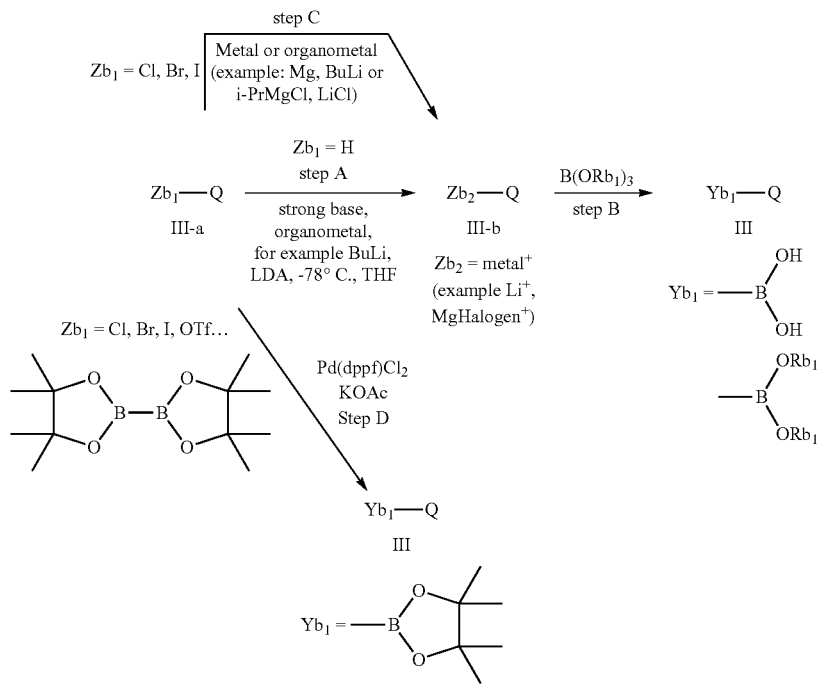

The very same preparation methods described in scheme 13 may be applied for the synthesis of intermediates of the formula IX.

Compounds of formula IV, wherein A, X, $X_1$, $R_1$ and $R_2$ are as described in formula I, can be prepared from com-

[1,1'-Bis(diphenylphosphino)ferrocene]dichloropalladium (II), also known as palladium dppf dichloride or Pd(dppf)$Cl_2$, is a common catalyst for this type of reaction. The temperature of the reaction is preferably comprised between 0° C. and the boiling point of the reaction mixture.

Scheme 14

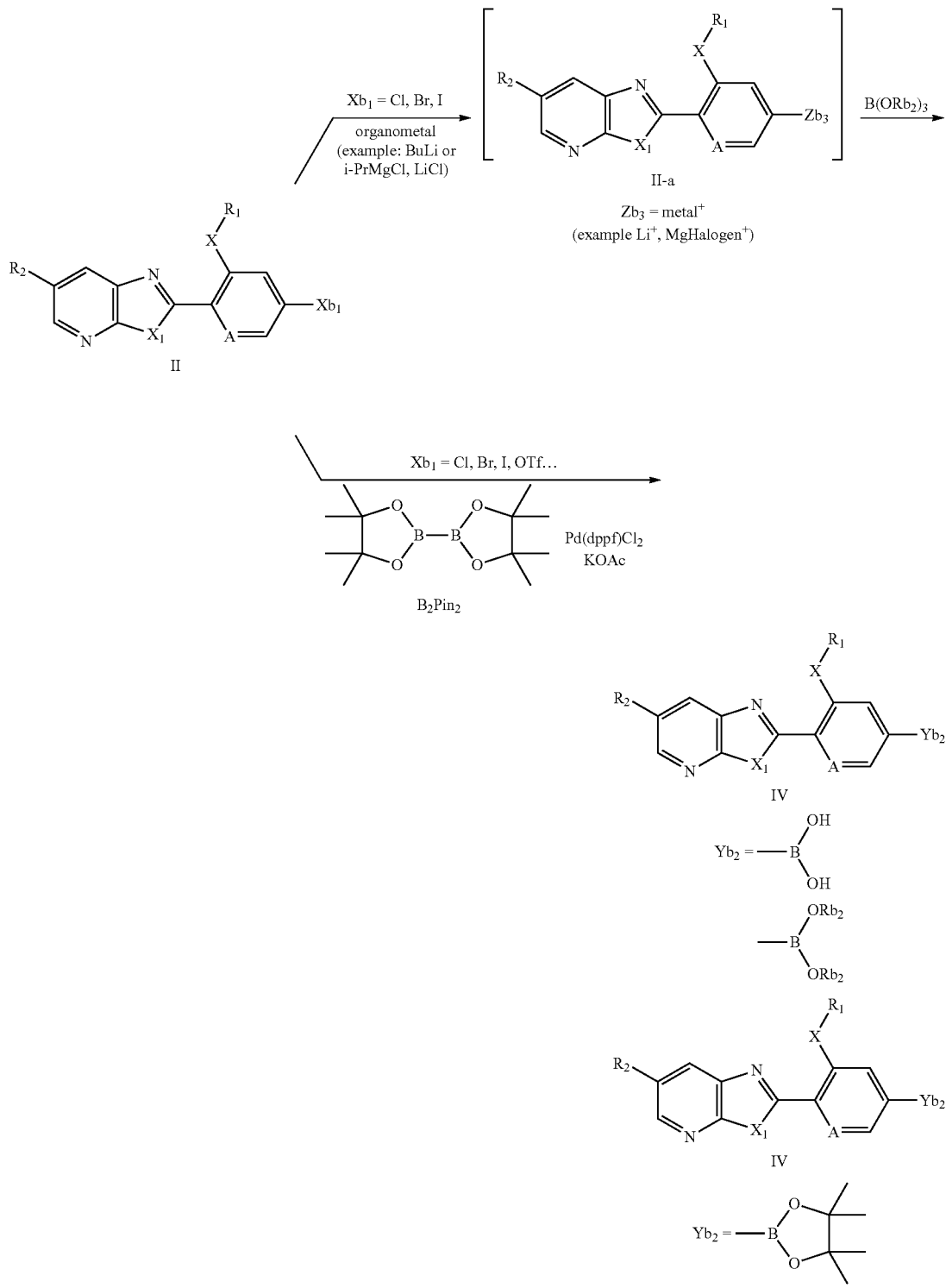

Compounds of formula I wherein Q is $C_3$-$C_6$cycloalkyl, or $C_3$-$C_6$cycloalkyl mono- or polysubstituted by substituents selected from the group consisting of halogen, cyano, $C_1$-$C_4$haloalkyl, and phenyl, may be prepared by methods described above (in particular, compounds of formula I wherein Q is cyclopropyl may be prepared by a Suzuki reaction involving cyclopropyl-boronic acid according to descriptions made in scheme 1). For the special case of compounds of formula I wherein Q is $C_3$-$C_6$cycloalkyl substituted by cyano (e.g. compounds Iaa) and $C_1$-$C_4$haloalkyl (e.g. compounds Iad), the compounds can be prepared by the methods shown in scheme 15.

Scheme 15

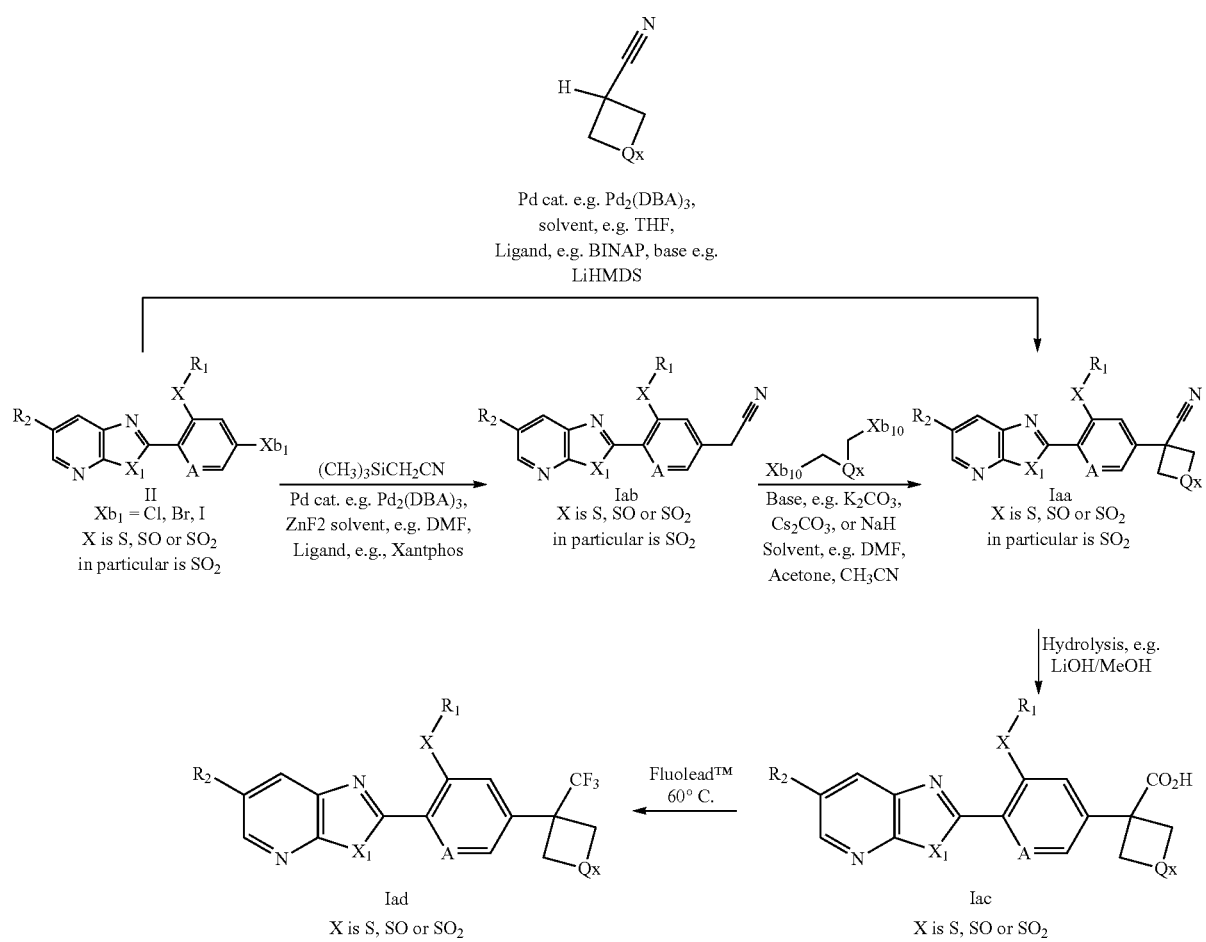

As shown in scheme 15, treatment of compounds of formula II, wherein X is S, SO or SO$_2$ (in particular SO$_2$), and wherein A, X$_1$, R$_1$ and R$_2$ are as defined above, and in which Xb$_1$ is a leaving group like, for example, chlorine, bromine or iodine (preferably bromine), or an aryl- or alkylsulfonate such as trifluoromethanesulfonate, with trimethylsilyl-acetonitrile TMSCN, in the presence of zinc(II) fluoride ZnF$_2$, and a palladium(0) catalyst such as tris(dibenzylideneacetone)dipalladium(0)-chloroform adduct (Pd$_2$(dba)$_3$), with a ligand, for example Xantphos, in an inert solvent, such as N,N-dimethylformamide DMF at temperatures between 100-180° C., optionally under microwave heating, leads to compounds of formula Iab, wherein X is S, SO or SO$_2$ (in particular SO$_2$). Such chemistry has been described in the literature, e.g. in *Org. Lett.* 16(24), 6314-6317, 2014. Compounds of formula Iab can be treated with compounds of formula XXXII, wherein Qx is a direct bond or is (CH$_2$)$_n$ and n is 1, 2 or 3, and in which Xb$_{10}$ is a leaving group such as a halogen (preferably chlorine, bromine or iodine), in the presence of a base such as sodium hydride, potassium carbonate K$_2$CO$_3$, or cesium carbonate Cs$_2$CO$_3$, in an inert solvent such as N,N-dimethylformamide DMF, acetone, or acetonitrile, at temperatures between 0-120° C., to give compounds of formula Iaa, wherein X is S, SO or SO$_2$ (in particular SO$_2$), and wherein A, X$_1$, R$_1$ and R$_2$ are as defined above and in which Qx is a direct bond or is (CH$_2$)$_n$ and n is 1, 2 or 3. Alternatively, compounds of formula Iaa can be prepared directly from compounds of formula II by treatment with compounds of formula XXXIII, wherein Qx is is as described in XXII, in presence of a catalyst such as Pd$_2$(dba)$_3$, with a ligand, such as BINAP, a strong base such as lithium hexamethyldisilazane LiHMDS, in an inert solvent such as tetrahydrofuran THF, at temperatures between 30-80° C. Such chemistry has been described in, for example, *J. Am. Chem. Soc.* 127(45), 15824-15832, 2005.

Compounds of the formula Iaa may further be utilized for the preparation of compounds of formula Iad (scheme 15). Indeed, compounds of formula Iaa, wherein X is S, SO or SO$_2$, and wherein A, X$_1$, R$_1$ and R$_2$ are as defined above and in which Qx is a direct bond or is (CH$_2$)$_n$ and n is 1, 2 or 3, may be hydrolyzed, under conditions known to a person skilled in the art (aqueous basic or acidic conditions; for example, lithium or sodium hydroxide in an alcoholic solvent such as methanol, at temperatures between 20° C. to refluxing conditions), to compounds of formula Iac, wherein X is S, SO or SO$_2$, and wherein A, X$_1$, R$_1$ and R$_2$ are as defined above and in which Qx is a direct bond or is (CH$_2$)$_n$ and n is 1, 2 or 3. Treatment of compounds of formula Iac with reagents such as sulfur tetrafluoride SF$_4$ or Fluolead (4-tert-butyl-2,6-dimethyl phenylsulfur trifluoride), optionally in the presence of hydrogen fluoride HF, at temperatures between 20-100° C., leads to compounds of formula Iad, wherein X is S, SO or $SO_2$, and wherein A, $X_1$, $R_1$ and $R_2$ are as defined above and in which Qx is a direct bond or is $(CH_2)_n$ and n is 1, 2 or 3.

Compounds of the formula Iaa may also be utilized for the preparation of compounds of formula Iaf (scheme 15a).

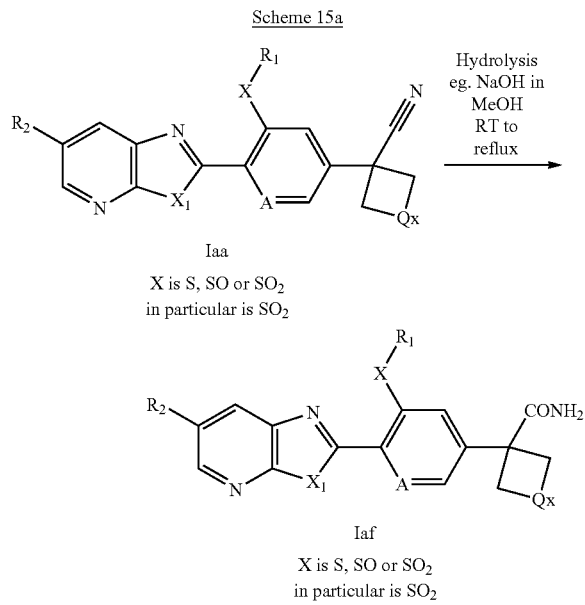

As shown in scheme 15a, compounds of formula Iaa, wherein X is S, SO or $SO_2$, and wherein A, $X_1$, $R_1$ and $R_2$ are as defined above and in which Qx is a direct bond or is $(CH_2)_n$ and n is 1, 2 or 3, may be hydrolyzed, under conditions known to a person skilled in the art (aqueous basic or acidic conditions; for example, lithium or sodium hydroxide in an alcoholic solvent such as methanol, at temperatures between 20° C. to refluxing conditions; or aqueous sulphuric acid, optionally in presence of a co-solvent, at temperatures between 20° C. to refluxing conditions), to compounds of formula Iaf, wherein X is S, SO or $SO_2$, and wherein A, $X_1$, $R_1$ and $R_2$ are as defined above and in which Qx is a direct bond or is $(CH_2)_n$ and n is 1, 2 or 3.

Alternatively compounds of formula Iaa can be prepared as shown in schemes 16 and 17. As shown in scheme 16, the chemistry used is identical to that described in scheme 15, it is just that the substrates for the reactions are different. Thus, reaction of the previously described compounds XXIV and/or XXIV-a, wherein X is S, SO or $SO_2$ (in particular $SO_2$), and wherein A, R1 are as defined above, and in which $Xb_4$ is a halogen like, for example, chlorine, bromine or iodine (preferably bromine), or an aryl- or alkylsulfonate such as trifluoromethanesulfonate, and in which $R_{LG}$ is $C_1$-$C_4$alkyl, with trimethylsilyl-acetonitrile TMSCN as described in scheme 15, leads to compounds of formula XXV, wherein X is S, SO or $SO_2$ (in particular $SO_2$), and wherein A, R1 are as defined above, and in which $R_{50}$ is $C_1$-$C_4$alkyl. These are converted into compounds of formula XXVI, wherein X is S, SO or $SO_2$ (in particular $SO_2$), and wherein Qx, A, $R_1$ are as defined above, and in which $R_{50}$ is $C_1$-$C_4$alkyl, by reacting with compounds of formula XXXII as described in scheme 15. Similarly, compounds XXVI can be prepared directly from XXIV and/or XXIV-a by the chemistry discussed in scheme 15 involving reagent XXXIII. Compounds of formula XXVI are readily hydrolysed by methods known to those skilled in the art to give compounds of formula XXVII, wherein X is S, SO or $SO_2$ (in particular $SO_2$), and wherein Qx, A, $R_1$ are as defined above.

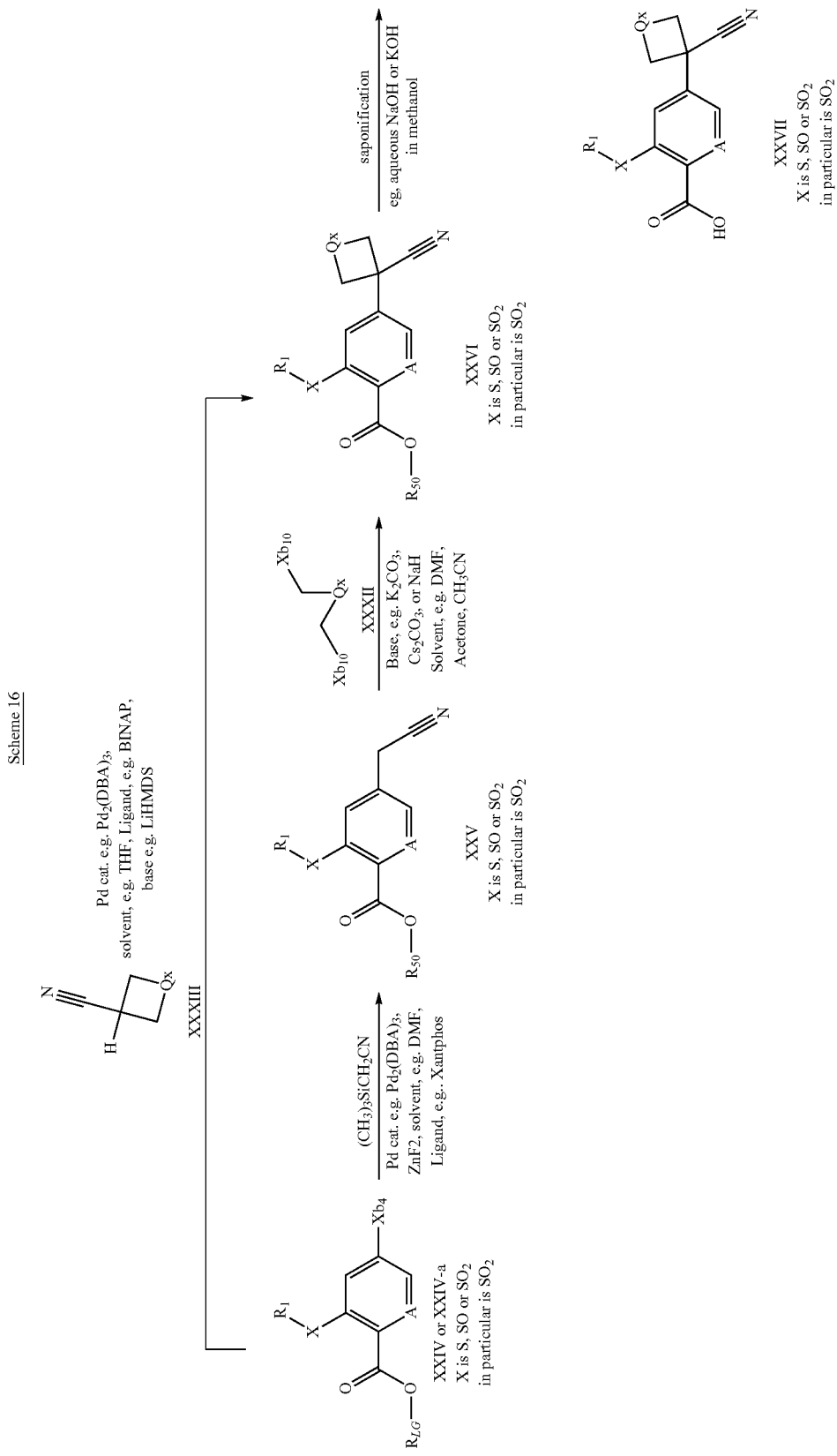

The chemistry shown in scheme 17 has previously been described in detail (see, for example, scheme 8). This chemistry involves forming an activated species XXVIIa, wherein X is S, SO or SO$_2$ (in particular SO$_2$), and wherein Qx, A, R$_1$ are as defined above, and in which LG$_1$ typically is chlorine, followed by amide coupling with a compound of formula XIII, or a salt thereof, to give the compounds of formula XV-a. Those compounds of formula XV-a can in turn be converted to compounds of formula Iaa by a formal dehydration step, previously described in scheme 8. All substituent definitions in scheme 17 are as described previously.

Scheme 17

XXVII
X is S, SO or SO$_2$
in particular is SO$_2$ (COCl)$_2$, inert solvent, e.g. CH$_2$Cl$_2$, room temp, or SOCl$_2$, CH$_2$Cl$_2$ room temp. or DCC, EDC, THF, or Pyridine rt-120° C.

XXVIIa
X is S, SO or SO$_2$
in particular is SO$_2$

XIII
optionaly in the presence of a base e.g. Et$_3$N, pyridine

1) PPh$_3$, DIAD, solvent, e.g. THF r.t to 50° C.
or
TsOH, inert solvent, e.g NMP, Microwave, rt to 180° C.

XV-a
X is S, SO or SO$_2$
in particular is SO$_2$

Iaa
X is S, SO or SO$_2$
in particular is SO$_2$

LG$_1$ = Cl,

X$_{01}$    X$_{02}$

The compounds of formula XV-int (XV-int)

wherein
R$_1$, R$_2$, R$_3$, X and A are as defined under formula I above, and wherein
Q is a group

R$_{0002}$ wherein R$_{0002}$ is cyano, are novel, especially developed for the preparation of the compounds of formula I according to the invention and therefore represent a further object of the invention. The preferences and preferred embodiments of the substituents of the compounds of formula I are also valid for the compounds of formula XV-int.

Compounds of formula I wherein Q is substituted C$_3$-cycloalkyl, forming the subgroup represented by compounds of formula Iae, can be prepared from compounds of formula XXVIII by the chemistry illustrated in scheme 18.

Scheme 18

XXVIII
R$_{01}$ = halogen, cyano, C$_1$-C$_4$alkyl, C$_1$-C$_4$haloalkyl, C$_3$-C$_6$cycloalkyl and phenyl CH$_2$N$_2$, Pd catalyst,
e.g. Pd(OAc)$_2$
solvent e.g. CH$_2$Cl$_2$
or
Et$_2$O

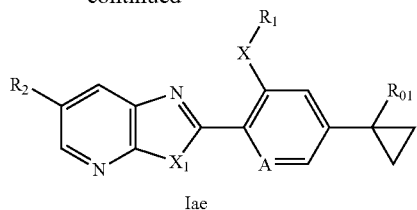

Iae $R_{01}$ = halogen, cyano, $C_1$-$C_4$alkyl, $C_1$-$C_4$haloalkyl, $C_3$-$C_6$cycloalkyl and phenyl In scheme 18, compounds of formula XXVIII, wherein $R_1$, $R_2$, $X_1$ and A are as previously defined, and in which X is S, SO or $SO_2$, and wherein $R_{01}$ is halogen, cyano, $C_1$-$C_4$alkyl, $C_1$-$C_4$haloalkyl, $C_3$-$C_6$cycloalkyl or phenyl, are treated with diazomethane $CH_2N_2$ in the presence of a catalyst, such as $Pd(OAc)_2$ or bis(benzonitrile)palladium(II) dichloride, in an inert solvent such as methylene chloride or ether, at ambient temperature or below, to form compounds of formula Iae, wherein the substituents are as defined under formula XXVIII. Such chemistry has been described in the literature (see for example *Org. Biomol. Chem.* 2, 2471, 2004, WO03/064418, or Med. Chem. Letts., 4, 514-516, 2013).

Another particular case of compounds of formula I is represented by compounds of formula I-b, wherein A, $R_1$, $R_2$, X and $X_1$ are as described in formula I and Q is a $C_3$-cycloalkyl disubstituted by halogen:

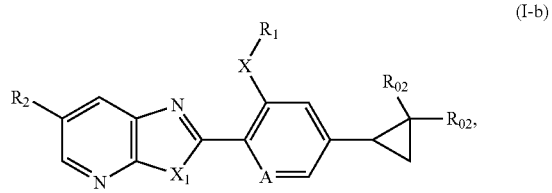

wherein $R_{02}$ is halogen, preferably fluorine, chlorine or bromine.

Compounds of the formula I-b-1 (a particular subset of compounds I-b wherein X is S (sulfide)), wherein A, $R_1$, $R_2$ and $X_1$ are as described in formula I and in which $R_{02}$ is chlorine or bromine,

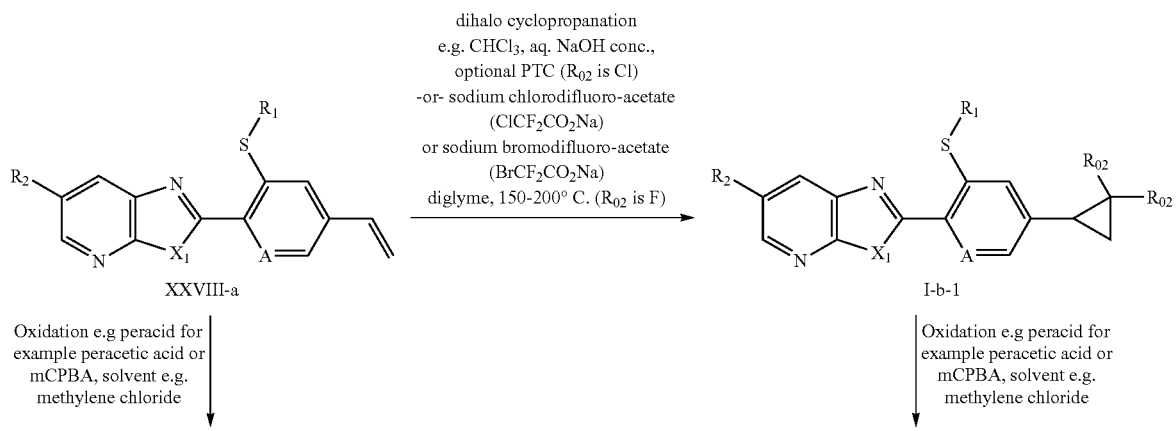

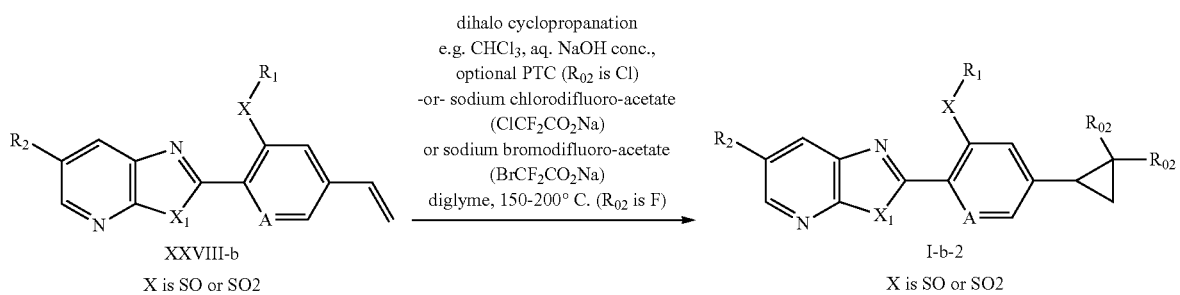

may be prepared, for example, by reacting compounds of formula XXVIII-a, wherein A, $R_1$, $R_2$ and $X_1$ are as described in formula I, with chloroform $CHCl_3$ or bromoform $CHBr_3$ (possibly acting as reagent and solvent) in presence of concentrated aqueous sodium or potassium hydroxide, optionally in presence of a phase transfer catalyst PTC, such as for example tetrabutyl ammonium bromide or triethyl benzyl ammonium chloride, optionally in the presence of an additional solvent such as dichloromethane, preferably at temperatures around 0° C. to 30° C. Such chemistry has been described in the literature (see for example Science of Synthesis, 34, 245-265, 2006). Alternatively, compounds of the formula I-b-1, wherein A, $R_1$, $R_2$ and $X_1$ are as described in formula I and in which $R_{02}$ is fluorine, may be prepared, for example, by reacting compounds of formula XXVIII-a, wherein A, $R_1$, $R_2$ and $X_1$ are as described in formula I, with reagents such as sodium chlorodifluoro-acetate ($ClCF_2CO_2Na$), sodium bromodifluoro-acetate ($BrCF_2CO_2Na$) or sodium trifluoro-acetate ($CF_3CO_2Na$) in solvents such as diglyme, tetrahydrofuran, dioxane or dimethoxyethane, at temperatures between 100 and 200° C. (preferably in the range 150-200° C.). Such chemistry has been described in the literature (see for example Synthesis, 2080-2084, 2010).

Oxidation of compounds of formula I-b-1, wherein A, $R_1$, $R_2$ and $X_1$ are as described in formula I, and wherein $R_{02}$ is halogen, preferably fluorine, chlorine or bromine, with a suitable oxidizing agent, into compounds of formula I-b-2, wherein A, $R_1$, $R_2$ and $X_1$ are as described in formula I, and wherein $R_{02}$ is halogen, preferably fluorine, chlorine or bromine, and in which X is SO or $SO_2$ may be achieved under conditions already described above.

Alternatively, compounds of formula I-b-2, wherein X is SO or $SO_2$, may be prepared from the sulfide compounds of formula XXVIII-a by involving the same chemistry as described above, but by changing the order of the steps (i.e. by running the sequence XXVIII-a to XXVIII-b via oxidation, followed by a dihalo cyclopropanation step to form I-b-2, wherein X is SO or $SO_2$).

The processes according to the invention for preparing compounds of formula I wherein Q is in the 4-position described above, as well as descriptions on all relevant associated intermediates (see text, descriptions and preparation methods above), may be applied analogously for the preparation of compounds of formula I, wherein Q is in the 3-position, possibly by changing the order of certain steps in a sequence and by slightly adapting reaction conditions in a manner known to a person skilled in the art. In scheme 19, compounds of formula I, wherein Q is in the 3-position, are represented by the compounds of formula I-A (I-A)

wherein the substituents are as defined as under formula I above. Compounds of formula Iaa-p constitutes a particular subset of compounds of formula I-A, wherein Q is a group

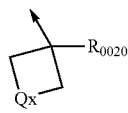

wherein $R_{0020}$ is cyano and Qx is as defined above.

Such a transposition is illustrated in scheme 19 for the preparation of compounds of formula I-A (respectively Iaa-p) from intermediates II-p, wherein all substituent definitions mentioned previously are also valid for the compounds shown.

Scheme 19:

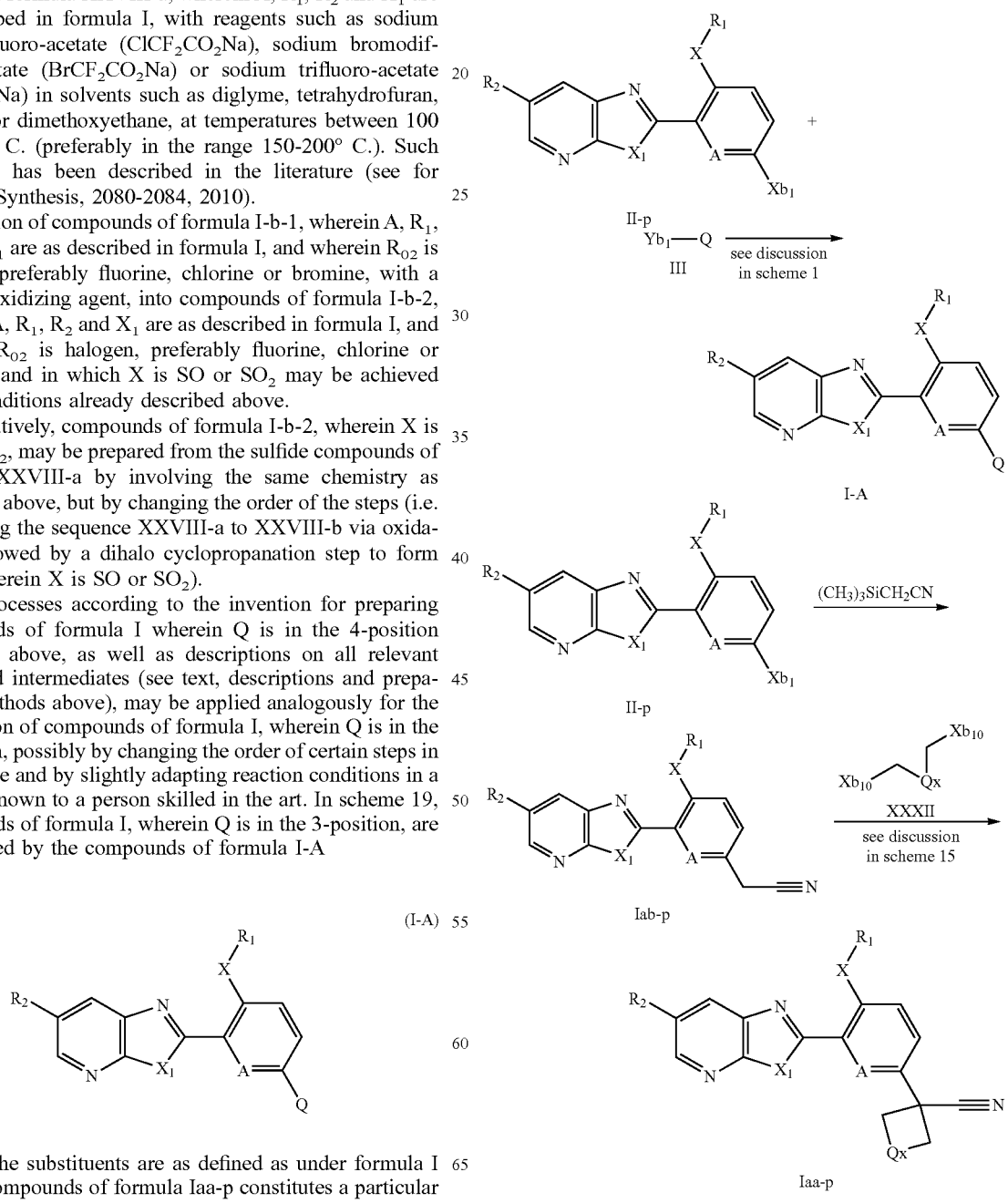

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 18 below can be prepared according to the methods described above. The examples which follow are intended to illustrate the invention and show preferred compounds of formula I.

Table X:

This table discloses 18 substituent definitions X.001 to X.018 of the formula I-1a:

and the N-oxides of the compounds of Table X. Ph represents the phenyl group, cyclo-C3 is the cyclopropyl group.

Table 1:

This table discloses the 18 compounds 1.001 to 1.018 of the formula I-1a, wherein $Xa_1$ is S, and $Ra_1$, $R_2$, $G_1$, $G_2$, $G_3$, $G_4$ and $G_5$ are as defined in Table X. For example, compound No. 1.001 has the following structure:

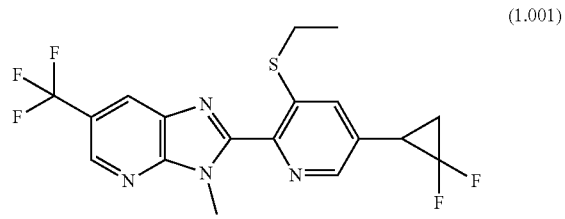

(1.001)

Table 2:

This table discloses the 18 compounds 2.001 to 2.018 of the formula I-1a, wherein $Xa_1$ is SO, and $Ra_1$, $R_2$, $G_1$, $G_2$, $G_3$, $G_4$ and $G_5$ are as defined in Table X.

Table 3:

This table discloses the 18 compounds 3.001 to 3.018 of the formula I-1a, wherein $Xa_1$ is $SO_2$, and $Ra_1$, $R_2$, $G_1$, $G_2$, $G_3$, $G_4$ and $G_5$ are as defined in Table X.

Table Y:

This table discloses 18 substituent definitions Y.001 to Y.018 of the formula I-2a:

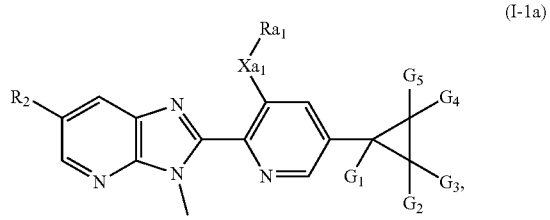

(I-1a)

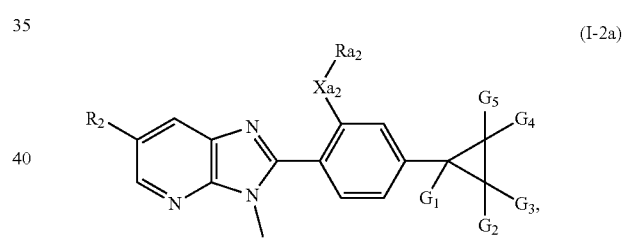

(I-2a)

wherein $Ra_1$, $R_2$, $G_1$, $G_2$, $G_3$, $G_4$ and $G_5$ are as defined below:

wherein $Ra_2$, $R_2$, $G_1$, $G_2$, $G_3$, $G_4$ and $G_5$ are as defined below:

TABLE X

| Comp. No | $R_2$ | $Ra_1$ | $G_1$ | $G_2$ | $G_3$ | $G_4$ | $G_5$ |
|---|---|---|---|---|---|---|---|
| X.001 | $CF_3$ | $CH_2CH_3$ | H | F | F | H | H |
| X.002 | $CF_3$ | $CH_2CH_3$ | H | Cl | Cl | H | H |
| X.003 | $CF_3$ | $CH_2CH_3$ | H | $CH_3$ | $CH_3$ | H | H |
| X.004 | $CF_3$ | $CH_2CH_3$ | H | H | H | H | H |
| X.005 | $CF_3$ | $CH_2CH_3$ | F | H | H | H | H |
| X.006 | $CF_3$ | $CH_2CH_3$ | Cl | H | H | H | H |
| X.007 | $CF_3$ | $CH_2CH_3$ | $CH_3$ | H | H | H | H |
| X.008 | $CF_3$ | $CH_2CH_3$ | $CF_3$ | H | H | H | H |
| X.009 | $CF_3$ | $CH_2CH_3$ | CN | H | H | H | H |
| X.010 | $CF_3$ | $CH_2CH_3$ | 4-Cl—Ph | H | H | H | H |
| X.011 | $CF_3$ | $CH_2CH_3$ | H | $CF_3$ | H | H | H |
| X.012 | $CF_3$ | $CH_2CH_3$ | H | CN | H | H | H |
| X.013 | $CF_3$ | $CH_2CH_3$ | H | cyclo-$C_3$ | H | H | H |
| X.014 | $CF_3$ | $CH_2CH_3$ | H | H | Ph | H | H |
| X.015 | $CF_3$ | $CH_2CH_3$ | H | H | H | 4-Cl—Ph | H |
| X.016 | $SCF_3$ | $CH_2CH_3$ | H | H | H | H | H |
| X.017 | $S(O)CF_3$ | $CH_2CH_3$ | H | H | H | H | H |
| X.018 | $S(O)_2CF_3$ | $CH_2CH_3$ | H | H | H | H | H |

TABLE Y

| Comp. No | $R_2$ | $Ra_2$ | $G_1$ | $G_2$ | $G_3$ | $G_4$ | $G_5$ |
|---|---|---|---|---|---|---|---|
| Y.001 | $CF_3$ | $CH_2CH_3$ | H | F | F | H | H |
| Y.002 | $CF_3$ | $CH_2CH_3$ | H | Cl | Cl | H | H |
| Y.003 | $CF_3$ | $CH_2CH_3$ | H | $CH_3$ | $CH_3$ | H | H |
| Y.004 | $CF_3$ | $CH_2CH_3$ | H | H | H | H | H |
| Y.005 | $CF_3$ | $CH_2CH_3$ | F | H | H | H | H |
| Y.006 | $CF_3$ | $CH_2CH_3$ | Cl | H | H | H | H |
| Y.007 | $CF_3$ | $CH_2CH_3$ | $CH_3$ | H | H | H | H |
| Y.008 | $CF_3$ | $CH_2CH_3$ | $CF_3$ | H | H | H | H |
| Y.009 | $CF_3$ | $CH_2CH_3$ | CN | H | H | H | H |
| Y.010 | $CF_3$ | $CH_2CH_3$ | 4-Cl—Ph | H | H | H | H |
| Y.011 | $CF_3$ | $CH_2CH_3$ | H | $CF_3$ | H | H | H |
| Y.012 | $CF_3$ | $CH_2CH_3$ | H | CN | H | H | H |
| Y.013 | $CF_3$ | $CH_2CH_3$ | H | cyclo-$C_3$ | H | H | H |
| Y.014 | $CF_3$ | $CH_2CH_3$ | H | H | Ph | H | H |
| Y.015 | $CF_3$ | $CH_2CH_3$ | H | H | H | 4-Cl—Ph | H |
| Y.016 | $SCF_3$ | $CH_2CH_3$ | H | H | H | H | H |
| Y.017 | $S(O)CF_3$ | $CH_2CH_3$ | H | H | H | H | H |
| Y.018 | $S(O)_2CF_3$ | $CH_2CH_3$ | H | H | H | H | H | and the N-oxides of the compounds of Table Y. Ph represents the phenyl group, cyclo-$C_3$ is the cyclopropyl group.

Table 4:
This table discloses the 18 compounds 4.001 to 4.018 of the formula I-2a, wherein $Xa_2$ is S, and $Ra_2$, $R_2$, $G_1$, $G_2$, $G_3$, $G_4$ and $G_5$ are as defined in Table Y.

Table 5:
This table discloses the 18 compounds 5.001 to 5.018 of the formula I-2a, wherein $Xa_2$ is SO, and $Ra_2$, $R_2$, $G_1$, $G_2$, $G_3$, $G_4$ and $G_5$ are as defined in Table Y.

Table 6:
This table discloses the 18 compounds 6.001 to 6.018 of the formula I-2a, wherein $Xa_2$ is $SO_2$, and $Ra_2$, $R_2$, $G_1$, $G_2$, $G_3$, $G_4$ and $G_5$ are as defined in Table Y.

Table Z:
This table discloses 6 substituent definitions Z.001 to Z.006 of the formula I-3a:

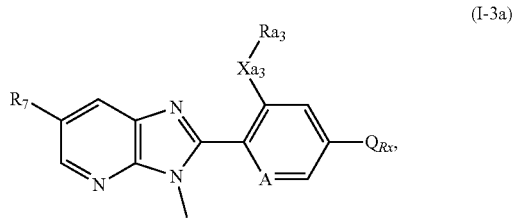

(I-3a)

wherein A, $Ra_3$, $R_7$ and $Q_{Rx}$ are as defined below:

TABLE Z

| Comp. No | $R_7$ | A | $Ra_3$ | $Q_{Rx}$ |
|---|---|---|---|---|
| Z.001 | $CF_3$ | N | $CH_2CH_3$ | cyclo-C4 |
| Z.002 | $CF_3$ | N | $CH_2CH_3$ | cyclo-C5 |
| Z.003 | $CF_3$ | N | $CH_2CH_3$ | cyclo-C6 |
| Z.004 | $CF_3$ | CH | $CH_2CH_3$ | cyclo-C4 |
| Z.005 | $CF_3$ | CH | $CH_2CH_3$ | cyclo-C5 |
| Z.006 | $CF_3$ | CH | $CH_2CH_3$ | cyclo-C6 | and the N-oxides of the compounds of Table Z. Cyclo-C4 represents the cyclobutyl group, cyclo-C5 is the cyclopentyl group, and cyclo-$C_6$ is the cyclohexyl group.

Table 7:
This table discloses the 6 compounds 7.001 to 7.006 of the formula I-3a, wherein $Xa_3$ is S, and $Ra_3$, $R_7$, A and $Q_{Rx}$ are as defined in Table Z.

Table 8:
This table discloses the 6 compounds 8.001 to 8.006 of the formula I-3a, wherein $Xa_3$ is SO, and $Ra_3$, $R_7$, A and $Q_{Rx}$ are as defined in Table Z.

Table 9:
This table discloses the 6 compounds 9.001 to 9.006 of the formula I-3a, wherein $Xa_3$ is $SO_2$, and $Ra_3$, $R_7$, A and $Q_{Rx}$ are as defined in Table Z.

Table U:
This table discloses 18 substituent definitions U.001 to U.018 of the formula I-4a:

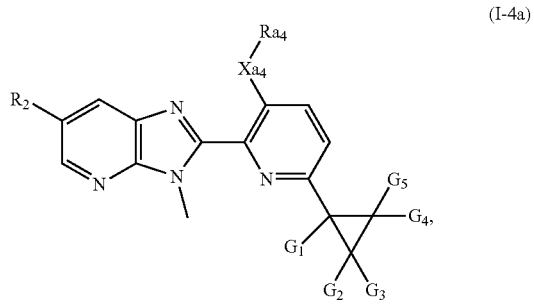

(I-4a)

wherein $Ra_4$, $R_2$, $G_1$, $G_2$, $G_3$, $G_4$ and $G_5$ are as defined below:

TABLE U

| Comp. No | $R_2$ | $Ra_4$ | $G_1$ | $G_2$ | $G_3$ | $G_4$ | $G_5$ |
|---|---|---|---|---|---|---|---|
| U.001 | $CF_3$ | $CH_2CH_3$ | H | F | F | H | H |
| U.002 | $CF_3$ | $CH_2CH_3$ | H | Cl | Cl | H | H |
| U.003 | $CF_3$ | $CH_2CH_3$ | H | $CH_3$ | $CH_3$ | H | H |
| U.004 | $CF_3$ | $CH_2CH_3$ | H | H | H | H | H |

TABLE U-continued

| Comp. No | $R_2$ | $Ra_4$ | $G_1$ | $G_2$ | $G_3$ | $G_4$ | $G_5$ |
|---|---|---|---|---|---|---|---|
| U.005 | $CF_3$ | $CH_2CH_3$ | F | H | H | H | H |
| U.006 | $CF_3$ | $CH_2CH_3$ | Cl | H | H | H | H |
| U.007 | $CF_3$ | $CH_2CH_3$ | $CH_3$ | H | H | H | H |
| U.008 | $CF_3$ | $CH_2CH_3$ | $CF_3$ | H | H | H | H |
| U.009 | $CF_3$ | $CH_2CH_3$ | CN | H | H | H | H |
| U.010 | $CF_3$ | $CH_2CH_3$ | 4-Cl—Ph | H | H | H | H |
| U.011 | $CF_3$ | $CH_2CH_3$ | H | $CF_3$ | H | H | H |
| U.012 | $CF_3$ | $CH_2CH_3$ | H | CN | H | H | H |
| U.013 | $CF_3$ | $CH_2CH_3$ | H | cyclo-$C_3$ | H | H | H |
| U.014 | $CF_3$ | $CH_2CH_3$ | H | H | Ph | H | H |
| U.015 | $CF_3$ | $CH_2CH_3$ | H | H | H | 4-Cl—Ph | H |
| U.016 | $SCF_3$ | $CH_2CH_3$ | H | H | H | H | H |
| U.017 | $S(O)CF_3$ | $CH_2CH_3$ | H | H | H | H | H |
| U.018 | $S(O)_2CF_3$ | $CH_2CH_3$ | H | H | H | H | H | and the N-oxides of the compounds of Table U. Ph represents the phenyl group, cyclo-$C_3$ is the cyclopropyl group.

Table 10:
This table discloses the 18 compounds 10.001 to 10.018 of the formula I-4a, wherein $Xa_4$ is S, and $Ra_4$, $R_2$, $G_1$, $G_2$, $G_3$, $G_4$ and $G_5$ are as defined in Table U.

Table 11:
This table discloses the 18 compounds 11.001 to 11.018 of the formula I-4a, wherein $Xa_4$ is SO, and $Ra_4$, $R_2$, $G_1$, $G_2$, $G_3$, $G_4$ and $G_5$ are as defined in Table U.

Table 12:
This table discloses the 18 compounds 12.001 to 12.018 of the formula I-4a, wherein $Xa_4$ is $SO_2$, and $Ra_4$, $R_2$, $G_1$, $G_2$, $G_3$, $G_4$ and $G_5$ are as defined in Table U.

Table V:
This table discloses 18 substituent definitions V.001 to V.018 of the formula I-5a:

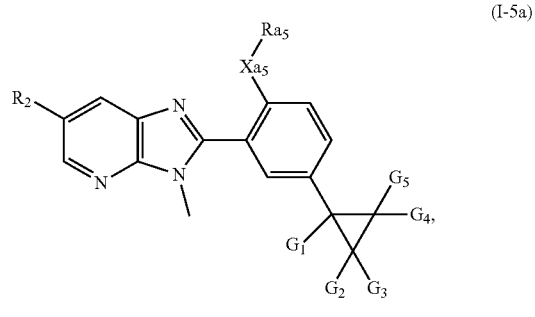

(I-5a)

wherein $Ra_5$, $R_2$, $G_1$, $G_2$, $G_3$, $G_4$ and $G_5$ are as defined below:

TABLE V

| Comp. No | $R_2$ | $Ra_5$ | $G_1$ | $G_2$ | $G_3$ | $G_4$ | $G_5$ |
|---|---|---|---|---|---|---|---|
| V.001 | $CF_3$ | $CH_2CH_3$ | H | F | F | H | H |
| V.002 | $CF_3$ | $CH_2CH_3$ | H | Cl | Cl | H | H |
| V.003 | $CF_3$ | $CH_2CH_3$ | H | $CH_3$ | $CH_3$ | H | H |
| V.004 | $CF_3$ | $CH_2CH_3$ | H | H | H | H | H |
| V.005 | $CF_3$ | $CH_2CH_3$ | F | H | H | H | H |
| V.006 | $CF_3$ | $CH_2CH_3$ | Cl | H | H | H | H |
| V.007 | $CF_3$ | $CH_2CH_3$ | $CH_3$ | H | H | H | H |
| V.008 | $CF_3$ | $CH_2CH_3$ | $CF_3$ | H | H | H | H |
| V.009 | $CF_3$ | $CH_2CH_3$ | CN | H | H | H | H |
| V.010 | $CF_3$ | $CH_2CH_3$ | 4-Cl—Ph | H | H | H | H |
| V.011 | $CF_3$ | $CH_2CH_3$ | H | $CF_3$ | H | H | H |
| V.012 | $CF_3$ | $CH_2CH_3$ | H | CN | H | H | H |
| V.013 | $CF_3$ | $CH_2CH_3$ | H | cyclo-$C_3$ | H | H | H |
| V.014 | $CF_3$ | $CH_2CH_3$ | H | H | Ph | H | H |
| V.015 | $CF_3$ | $CH_2CH_3$ | H | H | H | 4-Cl—Ph | H |
| V.016 | $SCF_3$ | $CH_2CH_3$ | H | H | H | H | H |
| V.017 | $S(O)CF_3$ | $CH_2CH_3$ | H | H | H | H | H |
| V.018 | $S(O)_2CF_3$ | $CH_2CH_3$ | H | H | H | H | H | and the N-oxides of the compounds of Table V. Ph represents the phenyl group, cyclo-C3 is the cyclopropyl group.

Table 13:
This table discloses the 18 compounds 13.001 to 13.018 of the formula I-5a, wherein $Xa_5$ is S, and $Ra_5$, $R_2$, $G_1$, $G_2$, $G_3$, $G_4$ and $G_5$ are as defined in Table V.

Table 14:
This table discloses the 18 compounds 14.001 to 14.018 of the formula I-5a, wherein $Xa_5$ is SO, and $Ra_5$, $R_2$, $G_1$, $G_2$, $G_3$, $G_4$ and $G_5$ are as defined in Table V.

Table 15:
This table discloses the 18 compounds 15.001 to 15.018 of the formula I-5a, wherein $Xa_5$ is $SO_2$, and $Ra_5$, $R_2$, $G_1$, $G_2$, $G_3$, $G_4$ and $G_5$ are as defined in Table V.

Table W:
This table discloses 6 substituent definitions W.001 to W.006 of the formula I-6a:

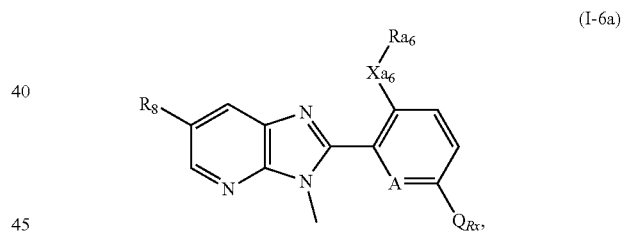

(I-6a)

wherein A, $Ra_6$, $R_8$ and $Q_{Rx}$ are as defined below:

TABLE W

| Comp. No | $R_8$ | A | $Ra_6$ | $Q_{Rx}$ |
|---|---|---|---|---|
| W.001 | $CF_3$ | N | $CH_2CH_3$ | cyclo-C4 |
| W.002 | $CF_3$ | N | $CH_2CH_3$ | cyclo-C5 |
| W.003 | $CF_3$ | N | $CH_2CH_3$ | cyclo-C6 |
| W.004 | $CF_3$ | CH | $CH_2CH_3$ | cyclo-C4 |
| W.005 | $CF_3$ | CH | $CH_2CH_3$ | cyclo-C5 |
| W.006 | $CF_3$ | CH | $CH_2CH_3$ | cyclo-C6 | and the N-oxides of the compounds of Table W. Cyclo-C4 represents the cyclobutyl group, cyclo-C5 is the cyclopentyl group, and cyclo-C6 is the cyclohexyl group.

Table 16:

This table discloses the 6 compounds 16.001 to 16.006 of the formula I-6a, wherein $Xa_6$ is S, and $Ra_6$, $R_8$, A and $Q_{Rx}$ are as defined in Table W.

Table 17:

This table discloses the 6 compounds 17.001 to 17.006 of the formula I-6a, wherein $Xa_6$ is SO, and $Ra_6$, $R_8$, A and $Q_{Rx}$ are as defined in Table W.

Table 18:

This table discloses the 6 compounds 18.001 to 18.006 of the formula I-6a, wherein $Xa_6$ is $SO_2$, and $Ra_6$, $R_8$, A and $Q_{Rx}$ are as defined in Table W.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate.

Examples of the abovementioned animal pests are:

from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri* Mats, *Odonaspis ruthae*, *Oregma lanigera* Zehnter, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, *Zyginidia scutellaris*;

from the order Hymenoptera, for example,

*Acromyrmex*, *Arge* spp, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order Isoptera, for example,

*Coptotermes* spp, *Corniternes cumulans*, *Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Grapholita* spp., *Hedya nubiferana*, *Heliothis* spp., *Hellula undalis*, *Herpetogramma* spp, *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp, *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis*;

from the order Thysanoptera, for example,

*Calliothrips phaseoli*, *Frankliniella* spp., *Heliothrips* spp, *Hercinothrips* spp., *Parthenothrips* spp, *Scirtothrips aurantii*, *Sericothrips variabilis*, *Taeniothrips* spp., *Thrips* spp;

from the order Thysanura, for example, *Lepisma saccharina*.

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis*, *Anthemis* spp., *Antirrhinum* spp., *Aster* spp., *Begonia* spp. (e.g. *B. elatior*, *B. semperflorens*, *B. tubéreux*), *Bougainvillea* spp., *Brachycome* spp., *Brassica* spp. (ornamental), *Calceolaria* spp., *Capsicum annuum*, *Catharanthus roseus*, *Canna* spp., *Centaurea* spp., *Chrysanthemum* spp., *Cineraria* spp. (*C. maritime*), *Coreopsis* spp., *Crassula coccinea*, *Cuphea ignea*, *Dahlia* spp., *Delphinium* spp., *Dicentra spectabilis*, *Dorotheantus* spp., *Eustoma grandiflorum*, *Forsythia* spp., *Fuchsia* spp., *Geranium gnaphalium*, *Gerbera* spp., *Gomphrena globosa*, *Heliotropium* spp., *Helianthus* spp., *Hibiscus* spp., *Hortensia* spp., *Hydrangea* spp., *Hypoestes phyllostachya*, *Impatiens* spp. (*I. Walleriana*), *Iresines* spp., *Kalanchoe* spp., *Lantana camara*, *Lavatera trimestris*, *Leonotis leonurus*, *Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum*, *P. Zonale*), *Viola* spp. (pansy), *Petunia* spp., *Phlox* spp., *Plecthranthus* spp., *Poinsettia* spp., *Parthenocissus* spp. (*P. quinquefolia*, *P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola*, *Schizanthus wisetonensis*, *Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba*.

Preferred ornamental species include African violet, Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; Arion (*A. ater, A. circumscriptus, A. hortensis, A. rufus*); Bradybaenidae (*Bradybaena fruticum*); Cepaea (*C. hortensis, C. Nemoralis*); ochlodina; Deroceras (*D. agrestis, D. empiricorum, D. laeve, D. reticulatum*); Discus (*D. rotundatus*); Euomphalia; Galba (*G. trunculata*); Helicelia (*H. itala, H. obvia*); Helicidae Helicigona arbustorum); Helicodiscus; Helix (*H. aperta*); Limax (*L. cinereoniger, L. flavus, L. marginatus, L. maximus, L. tenellus*); Lymnaea; Milax (*M. gagates, M. marginatus, M. sowerbyi*); Opeas; Pomacea (*P. canaticulata*); Vallonia and Zanitoides.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810). Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1 Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Btl 1 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Btl 1 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium, Anthracnose*, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store ambients and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO 2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
| --- | --- | --- |
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
| --- | --- | --- |
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, *Sassafras*, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, *Viburnum*, Elm, Sourwood, Blueberry, *Rhododendron*, Azalea, Laurel, Poplar, Willow, Mulberry |
| | *Oncideres cingulata* | Hickory, Pecan, Persimmon, Elm, Sourwood, Basswood, Honeylocust, Dogwood, *Eucalyptus*, Oak, Hackberry, Maple, Fruit trees |
| | *Saperda calcarata* | Poplar |
| | *Strophiona nitens* | Chestnut, Oak, Hickory, Walnut, Beech, Maple |

TABLE B-continued

Examples of native woodborers of economic importance.

| Family | Species | Host or Crop Infested |
| --- | --- | --- |
| Scolytidae | Corthylus columbianus | Maple, Oak, Yellow-poplar, Beech, Boxelder, Sycamore, Birch, Basswood, Chestnut, Elm |
|  | Dendroctonus frontalis | Pine |
|  | Dryocoetes betulae | Birch, Sweetgum, Wild cherry, Beech, Pear |
|  | Monarthrum fasciatum | Oak, Maple, Birch, Chestnut, Sweetgum, Blackgum, Poplar, Hickory, Mimosa, Apple, Peach, Pine |
|  | Phloeotribus liminaris | Peach, Cherry, Plum, Black cherry, Elm, Mulberry, Mountain-ash |
|  | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
|  | Sannina uroceriformis | Persimmon |
|  | Synanthedon exitiosa | Peach, Plum, Nectarine, Cherry, Apricot, Almond, Black cherry |
|  | Synanthedon pictipes | Peach, Plum, Cherry, Beach, Black Cherry |
|  | Synanthedon rubrofascia | Tupelo |
|  | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
|  | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergatesspp., Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mp" means melting point in ° C. Free radicals represent methyl groups. $^1$H NMR measurements were recorded on a Brucker 400 MHz spectrometer, chemical shifts are given in ppm relevant to a TMS standard. Spectra measured in deuterated solvents as indicated. Either one of the LCMS or GCMS methods below was used to characterize the compounds. The characteristic LCMS values obtained for each compound were the retention time ("$R_t$", recorded in minutes) and the measured molecular ion $(M+H)^-$.

LCMS and GCMS Methods:
Method 1 (LCMS/MS-API 2000/Q trap)
API 2000 Mass Spectrometer from Applied Biosystems (Single quadrupole mass spectrometer); Ionisation method: Electrospray; Polarity: positive ions. Capillary (kV) 5.5, DP (V) 50.00, Entrance Potential (V)10, Focusing Potential (V) 400, Source Temperature (° C.) 200, Ion Source Gas1 (Psi) 40, Ion Source Gas 2 (Psi) 50, Curtain Gas (Psi)40; Mass range: 100 to 800 amu; UV Wavelength range (nm): 220 to 260; Type of column: Zorbax Extend C18; Column length: 50 mm; Internal diameter of column: 4.6 mm; Particle Size: 5 micron Instrument Shimadzu Prominance with the following HPLC gradient conditions
(Solvent A: 10 Mm $NH_4OAc$ in Water and Solvent B: Acetonitrile)
Flow rate: 1.2 ml/min

| TIME | MODULE | % A (Buffer) | % B ($CH_3CN$) |
|---|---|---|---|
| 0.01 | Pumps | 90 | 10 |
| 1.50 | Pumps | 70 | 30 |
| 3.00 | Pumps | 10 | 90 |
| 4.00 | Pumps | 10 | 90 |
| 5.00 | Pumps | 90 | 10 |
| 5.10 | System Controller | Stop | |

Method 2 (UPLC1)
ACQUITY SQD Mass Spectrometer from Waters (Single quadrupole mass spectrometer); Ionisation method: Electro spray; Polarity: positive ions. Capillary (kV) 3.00, Cone (V) 40.00, Extractor (V) 3.00, Source Temperature (° C.) 150, Desolvation Temperature (° C.) 400, Cone Gas Flow (L/Hr) 50, Desolvation Gas Flow (L/Hr) 750; Mass range: 100 to 800 Da; DAD Wavelength range (nm): 210 to 400; Flow rate: 1.5 ml/min; Type of column: Resteck; Column length: 30 mm; Internal diameter of column: 2.1 mm; Particle Size: 1.8 micron; Temperature: 50° C.
Method Waters ACQUITY UPLC with the following HPLC gradient conditions
(Solvent A: 0.05% Formic acid in water and Solvent B: Acetonitrile)

| TIME | MODULE | % A (Buffer) | % B (CH3CN) |
|---|---|---|---|
| 0.00 | Pumps | 98 | 2 |
| 0.75 | Pumps | 98 | 2 |

| TIME | MODULE | % A (Buffer) | % B (CH3CN) |
| --- | --- | --- | --- |
| 1.00 | Pumps | 90 | 10 |
| 2.00 | Pumps | 2 | 98 |
| 2.25 | Pumps | 2 | 98 |
| 2.90 | Pumps | 98 | 2 |
| 3.00 | Pumps | 98 | 2 |

Method 3:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH; gradient: 0 min 0% B, 100% A; 1.2-1.5 min 100% B; Flow (ml/min) 0.85.

Method 4:

GCMS analyses were performed on a Thermo Electron instrument where a TRACE GC ULTRA gas chromatograph (equipped with a Zebron Phenomenex ZB-5 ms 15 m, diam: 0.25 mm, 0.25 µm column; $H_2$ flow 1.2 mL/min; temp injector: 250° C.; temp detector: 220° C.; method: start at 70° C., then 25° C./min until 320° C., hold 2 min at 320° C.) was linked to a DSQ mass spectrometer characterizing the compounds by electron ionisation (EI).

Example P1: Preparation of 2-(5-cyclopropyl-3-ethylsulfanyl-2-pyridyl)-3-methyl-6-(trifluoromethyl) imidazo[4,5-b]pyridine (compound P1)

Step 1: Preparation of 5-bromo-3-chloro-N-[2-(methylamino)-5-(trifluoromethyl)-3-pyridyl]pyridine-2-carboxamide

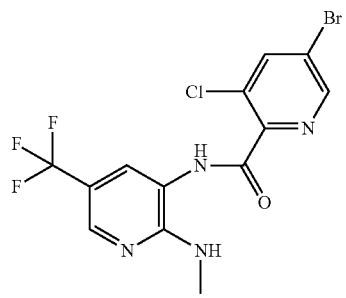 [SMILES: CNc1ncc(C(F)(F)F)cc1NC(=O)c1ncc(Br)cc1Cl]

To a stirred solution of 5-bromo-3-chloro-pyridine-2-carboxylic acid (1 g, 4.22 mmol) in dichloromethane (10 ml) was added oxalyl chloride (1.0 ml, 12.68 mmol) and a catalytic amount of N,N-dimethylformamide at 0° C. After addition, temperature of the reaction mixture was slowly raised to ambient temperature and stirring continued at ambient temperature for 2 hours. After completion of the reaction, the solvent was evaporated under reduced pressure to give the crude 5-bromo-3-chloro-pyridine-2-carbonyl chloride. This crude material was dissolved in dichloromethane and added dropwise to a solution of N2-methyl-5-(trifluoromethyl)pyridine-2,3-diamine (0.88 g, 4.65 mmol) and triethylamine (0.71 ml, 5.07 mmol) in dichloromethane at 0° C. The reaction mixture was stirred at ambient temperature for 16 hours. After completion of the reaction, the mixture was quenched with water (100 ml) and extracted with dichloromethane. The combined organic layers were washed with brine (100 ml), dried over sodium sulfate and concentrated. The residue was purified by combi flash (gradient 20-40% ethyl acetate in hexane) to afford 5-bromo-3-chloro-N-[2-(methylamino)-5-(trifluoromethyl)-3-pyridyl]pyridine-2-carboxamide as an off-white solid (1.0 g). LCMS (method 1): 409/411/413 (M+H)$^+$; retention time: 3.45 min.

Step 2: Preparation of 2-(5-bromo-3-chloro-2-pyridyl)-3-methyl-6-(trifluoromethyl)imidazo [4,5-b]pyridine

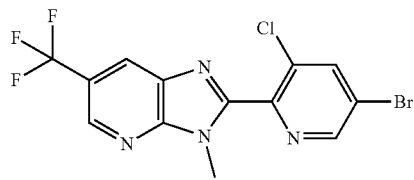 [SMILES: Cn1c(-c2ncc(Br)cc2Cl)nc2cc(C(F)(F)F)cnc21]

To a stirred solution of 5-bromo-3-chloro-N-[2-(methylamino)-5-(trifluoromethyl)-3-pyridyl]pyridine-2-carboxamide (500 mg, 1.2 mmol) in xylene (5 ml) was added p-toluenesulfonic acid (930 mg, 4.88 mmol) and the mixture was refluxed for 6 hours. The reaction was monitored by TLC and after maximum conversion of the starting material, the mixture was dissolved in ethyl acetate (50 ml) and washed with water (50 ml) and brine (50 ml), dried over sodium sulfate and concentrated under reduced pressure. The crude compound was purified by combi-flash (gradient 5-15% ethyl acetate in hexane) to give 2-(5-bromo-3-chloro-2-pyridyl)-3-methyl-6-(trifluoromethyl)imidazo[4,5-b]pyridine as an off-white solid (200 mg). LCMS (method 1): 391/393/395 (M+H)$^+$; retention time: 3.63 min.

Step 3: Preparation of 2-(3-chloro-5-cyclopropyl-2-pyridyl)-3-methyl-6-(trifluoromethyl)imidazo [4,5-b]pyridine

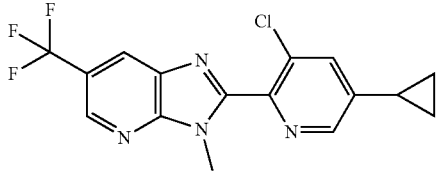 [SMILES: Cn1c(-c2ncc(C3CC3)cc2Cl)nc2cc(C(F)(F)F)cnc21]

To a stirred solution of 2-(5-bromo-3-chloro-2-pyridyl)-3-methyl-6-(trifluoromethyl)imidazo [4,5-b]pyridine (2 g, 5.1 mmol) in toluene (40 ml; degas the solution with $N_2$ for 15 minutes) was added cyclopropylboronic acid (790 mg, 9.19 mmol), tricyclohexylphophine (573 mg, 2.04 mmol), potassium phosphate $K_3PO_4$ (4.3 g, 20.4 mmol) under nitrogen atmosphere. The reaction mixture was again degassed with $N_2$ over 10 minutes before adding palladium(II) acetate Pd(OAc)$_2$ (57 mg, 0.25 mmol) and water (3.0 ml). After addition, temperature of the reaction mixture was slowly raised to reflux condition and stirring continued for 16 hours. After completion of the reaction, the mixture was diluted with ethyl acetate (250 ml), washed with water (250 ml) and brine (250 ml), dried over sodium sulfate and concentrated under reduced pressure. The crude compound was purified by column chromatography (gradient 10-15% ethyl acetate in hexane) to afford 2-(3-chloro-5-cyclopropyl-2-pyridyl)-3-methyl-6-(trifluoromethyl)imidazo[4,5-b]pyridine as an off-white solid (510 mg). LCMS (method 1): 353/355 (M+H)$^+$; retention time: 3.63 min.

Step 4: Preparation of 2-(5-cyclopropyl-3-ethylsulfanyl-2-pyridyl)-3-methyl-6-(trifluoromethyl) imidazo[4,5-b]pyridine (compound P1)

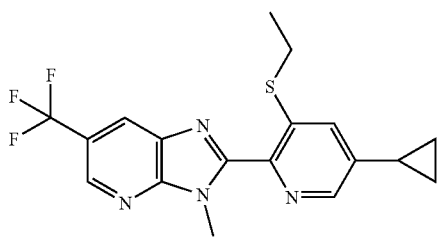 [SMILES: CCSc1cc(C2CC2)cnc1-c1nc2cc(C(F)(F)F)cnc2n1C]

To a stirred solution of 2-(3-chloro-5-cyclopropyl-2-pyridyl)-3-methyl-6-(trifluoromethyl)imidazo [4,5-b]pyridine (300 mg, 0.85 mmol) in N,N-dimethylformamide (3 ml) was added sodium ethanethiolate (143 mg, 1.7 mmol) at ambient temperature. After addition, temperature of the reaction mixture was slowly raised to reflux and stirring continued for 6 hours. The reaction was monitored by LC-MS and after completion, the mixture was diluted with ethyl acetate (20 ml), washed with water, dried over sodium sulfate and concentrated under reduced pressure. The crude compound was triturated using 10% diethyl ether in hexane, filtered and dried to give 2-(5-cyclopropyl-3-ethylsulfanyl-2-pyridyl)-3-methyl-6-(trifluoromethyl)imidazo[4,5-b]pyridine (title compound P1) as an off-white solid (90 mg), mp 119-121° C. LCMS (method 1): 379 (M+H)$^+$; retention time: 3.76 min.

Example P2: Preparation of 2-(5-cyclopentyl-3-ethylsulfanyl-2-pyridyl)-3-methyl-6-(trifluoromethyl) imidazo [4,5-b]pyridine (compound P2)

Step 1: Preparation of 2-(3-chloro-5-cyclopentyl-2-pyridyl)-3-methyl-6-(trifluoromethyl)imidazo [4,5-b]pyridine

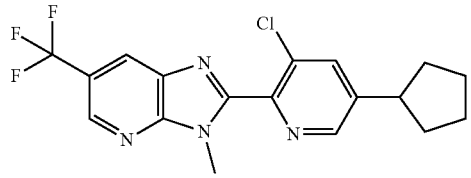 [SMILES: Cn1c(-c2ncc(C3CCCC3)cc2Cl)nc2cc(C(F)(F)F)cnc21]

A mixture of zinc Zn (4.36 g, 67.1 mmol) and lithium chloride LiCl (2.85 g, 67.1 mmol) were heated under high vacuum using hot gun over 10 minutes, then cooled to ambient temperature under argon atmosphere. Dry tetrahydrofuran (25 ml) was added to the mixture, followed by 1,2-dibromo ethylene (0.2 ml), then the mixture was heated to 50° C. slowly. Suddenly an exothermic reaction was observed. The suspension was stirred for 20 minutes at 50° C. under argon atmosphere. Trimethylsilyl chloride TMS-Cl (0.05 ml) and then an iodine solution (0.05 ml, 0.5 M in tetrahydrofuran) were added. The reaction was stirred at 50° C. for 30 minutes, cyclopentylbromide was added dropwise at the same temperature. The reaction was stirred at 50° C. for 16 hours, cooled to ambient temperature and stirring stopped to settle all suspended solid materials. The upper clear solution was used for the reaction.

To a stirred degassed solution of 2-(5-bromo-3-chloro-2-pyridyl)-3-methyl-6-(trifluoromethyl)imidazo [4,5-b]pyridine (700 mg, 1.7 mmol) in dry tetrahydrofuran (10 ml) was added 2-dicyclohexyl-phosphino-2',6'-dimethoxybiphenyl S-PHOS (74 mg, 0.17 mmol), bis(triphenylphosphine)palladium(II) dichloride Pd(PPh$_3$)$_2$Cl$_2$ (120 mg, 0.17 mmol), cyclopentyl zinc bromide (2.3 ml, 3.4 mmol) under an argon atmosphere. The reaction mixture was again degassed with argon over 10 min and stirred for 16 hours at ambient temperature. After completion of the reaction, the mixture was quenched with water (50 ml), filtered through a celite bed, the residue was washed with ethyl acetate and the aqueous layer extracted with ethyl acetate (3×10 ml). The combined organic layers were washed with brine (10 ml), dried over sodium sulfate and concentrated under reduced pressure. The crude compound was purified by column chromatography (gradient 10-15% ethyl acetate in dichloromethane) to give the desired compound as an orange sticky solid. This material was washed with diethyl ether (0.5 ml) and n-pentane (5 ml), filtered and dried to give the desired 2-(3-chloro-5-cyclopentyl-2-pyridyl)-3-methyl-6-(trifluoromethyl)imidazo[4,5-b]pyridine as a light yellow solid (400 mg), mp 112-114° C. LCMS (method 1): 381/383 (M+H)$^+$; retention time: 4.06 min.

Step 2: Preparation of 2-(5-cyclopentyl-3-ethylsulfanyl-2-pyridyl)-3-methyl-6-(trifluoromethyl) imidazo [4,5-b]pyridine (compound P2)

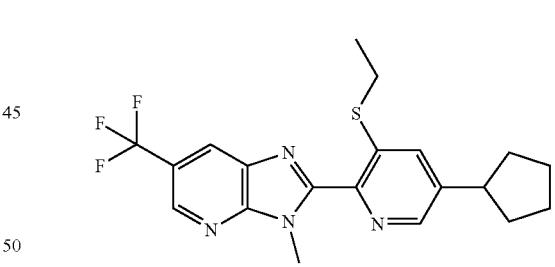

To a stirred solution of 2-(3-chloro-5-cyclopentyl-2-pyridyl)-3-methyl-6-(trifluoromethyl)imidazo[4,5-b]pyridine (300 mg, 0.79 mmol) in N,N-dimethylformamide (3 ml) was added sodium ethanethiolate (132 mg, 1.6 mmol) at ambient temperature. After addition, the temperature of the reaction was slowly raised to 90° C. and stirring continued for 3 hours. The reaction was monitored by LC-MS and after completion of the reaction, the mixture was diluted with ethyl acetate (20 ml), washed with water, dried over sodium sulfate and concentrated under reduced pressure. The crude product was purified by column chromatography using silica gel (gradient 15% ethyl acetate in hexane) to give 2-(5-cyclopentyl-3-ethylsulfanyl-2-pyridyl)-3-methyl-6-(trifluoromethyl) imidazo[4,5-b]pyridine (title compound P2) as an off-white solid (250 mg). LCMS (method 1): 407 (M+H)$^+$; retention time: 4.28 min.

Example P3: Preparation of 2-(5-cyclohexyl-3-ethylsulfanyl-2-pyridyl)-3-methyl-6-(trifluoromethyl) imidazo [4,5-b]pyridine (compound P3)

Step 1: Preparation of 2-(3-chloro-5-cyclohexyl-2-pyridyl)-3-methyl-6-(trifluoromethyl)imidazo [4,5-b]pyridine

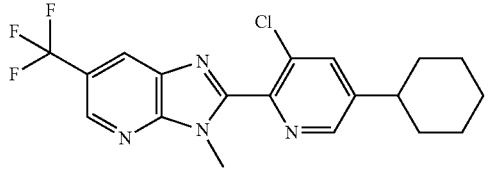 [SMILES: Cn1c(-c2ncc(C3CCCCC3)cc2Cl)nc2cc(C(F)(F)F)cnc21]

To a stirred, degassed solution of 2-(5-bromo-3-chloro-2-pyridyl)-3-methyl-6-(trifluoromethyl)imidazo [4,5-b]pyridine (1 g, 2.5 mmol) in dry tetrahydrofuran (10 ml) was added [1,1'-bis(diphenylphosphino) ferrocene]dichloropalladium(II) Pd(dppf)Cl$_2$ (183 mg, 0.25 mmol) and cyclohexyl zinc bromide (10.2 ml, 5.1 mmol, 0.5 M in tetrahydrofuran) under an argon atmosphere. The reaction mixture was again degassed with argon over 10 minutes. The temperature of the reaction mixture was slowly raised to 70° C. and stirring was continued for 16 hours. The reaction was monitored by TLC and after completion of the reaction, the mixture was quenched with water (50 ml), filtered through a celite bed and the residue was washed with ethyl acetate. The aqueous layer was extracted with ethyl acetate (3×10 ml) and the combined organic layers were washed with brine (10 ml), dried over sodium sulfate and concentrated under reduced pressure. The crude compound was purified by column chromatography (gradient 10-15% ethyl acetate in dichloromethane) to give the desired compound as an orange sticky solid. This material was washed with diethyl ether (0.5 ml) give the desired product 2-(3-chloro-5-cyclohexyl-2-pyridyl)-3-methyl-6-(trifluoromethyl)imidazo[4,5-b]pyridine as a light yellow solid (250 mg), mp 144-146° C. LCMS (method 2): 395/397 (M+H)$^+$; retention time: 1.86 min.

Step 2: Preparation of 2-(5-cyclohexyl-3-ethylsulfanyl-2-pyridyl)-3-methyl-6-(trifluoromethyl) imidazo [4,5-b]pyridine (compound P3)

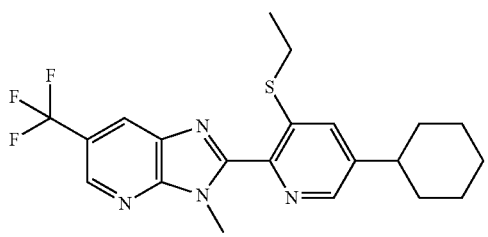 [SMILES: CCSc1cc(C2CCCCC2)cnc1-c1nc2cc(C(F)(F)F)cnc2n1C]

To a stirred solution of 2-(3-chloro-5-cyclohexyl-2-pyridyl)-3-methyl-6-(trifluoromethyl)imidazo[4,5-b]pyridine (300 mg, 0.76 mmol) in N,N-dimethylformamide (3 ml) was added sodium ethanethiolate (128 mg, 1.5 mmol) at ambient temperature. After addition, the temperature of the reaction mixture was slowly raised to 90° C. and stirring was continued for 3 hours. The reaction was monitored by LC-MS and after completion of the reaction, the mixture was diluted with ethyl acetate (20 ml), washed with water, dried over sodium sulfate and concentrated under reduced pressure. The crude compound was purified by column chromatography using silica gel (gradient 15% ethyl acetate in hexane) to give the desired product 2-(5-cyclohexyl-3-ethylsulfanyl-2-pyridyl)-3-methyl-6-(trifluoromethyl) imidazo[4,5-b]pyridine (title compound P3) as an off-white solid (220 mg), m.p. 148-150° C. LCMS (method 1): 421 (M+H)$^+$; retention time: 4.52 min.

Example P4: Preparation of 2-(5-cyclopropyl-3-ethylsulfonyl-2-pyridyl)-3-methyl-6-(trifluoromethyl) imidazo[4,5-b]pyridine (compound P4)

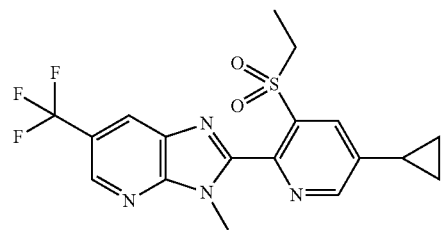 [SMILES: CCS(=O)(=O)c1cc(C2CC2)cnc1-c1nc2cc(C(F)(F)F)cnc2n1C]

To a stirred solution of 2-(5-cyclopropyl-3-ethylsulfanyl-2-pyridyl)-3-methyl-6-(trifluoromethyl) imidazo[4,5-b]pyridine (100 mg, 0.26 mmol) in dichloromethane (2 ml) was added meta-chloro-peroxybenzoic acid (128 mg, m-CPBA, ~77%, 0.57 mmol) at 0° C. After addition, temperature of the reaction mixture was slowly raised to ambient temperature and stirring continued for 2 hours. After completion of the reaction, the mixture was diluted with dichloromethane (50 ml), washed with aqueous saturated sodium thiosulfite (100 ml) and aqueous saturated sodium hydrogen carbonate solution (100 ml), dried over sodium sulfate and concentrated under reduced pressure. The crude compound was purified by column chromatography (gradient 20-25% ethyl acetate in hexane) to give 2-(5-cyclopropyl-3-ethylsulfonyl-2-pyridyl)-3-methyl-6-(trifluoromethyl) imidazo[4,5-b]pyridine (title compound P4) as a sticky solid (40 mg). LCMS (method 1): 411 (M+H)$^+$; retention time: 3.47 min.

Example P5: Preparation of 1-[5-ethylsulfonyl-6-[3-methyl-6-(trifluoromethyl)imidazo[4,5-b]pyridin-2-yl]-3-pyridyl]cyclopropanecarbonitrile (compound P9)

Step 1: Preparation of 5-bromo-3-ethylsulfanyl-pyridine-2-carbonitrile

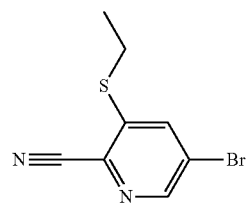

Under nitrogen atmosphere, a solution of 5-bromo-3-fluoro-pyridine-2-carbonitrile (1.005 g, 5.00 mmol) in dry N,N-dimethylformamide (15 ml) was cooled to −50° C. and to this was added dropwise a freshly prepared solution of sodium ethanethiolate (0.429 g, 5.10 mmol) in dry N,N-dimethylformamide (5 ml). After stirring at −50° C. for 30 minutes, the cooling bath was removed and the mixture was allowed to warm to ambient temperature. Water and brine were added and the aqueous mixture was extracted with ethyl acetate. After separation, the organic layer was washed twice with brine, dried over sodium sulfate and concentrated. The crude product was purified over silica by flash column chromatography (0 to 40% gradient of ethyl acetate in heptane) to afford the title compound (0.93 g) as a solid. GCMS (method 4): 242/244 (M)+, retention time 6.33 min. ¹H-NMR (CDCl₃, ppm) 1.41 (3H), 3.06 (2H), 7.82 (1H), 8.49 (1H).

Alternative preparation method: Under nitrogen atmosphere, a solution of 5-bromo-3-nitro-pyridine-2-carbonitrile (45.35 g, 199 mmol) in dry N,N-dimethylformamide (500 ml) was cooled to −50° C. and to this was added dropwise a freshly prepared solution of sodium ethanethiolate (17.4 g, 207 mmol) in dry N,N-dimethylformamide (200 ml) (not a completely clear solution). After complete addition, stirring was continued at −50° C. for 30 minutes. Water and brine were added and the cooling bath was removed. The aqueous mixture was extracted with ethyl acetate. After separation, the water layer was extracted with ethyl acetate once more. The combined the organic layers were washed twice with brine, dried over sodium sulfate and concentrated. The crude product was purified over silica by flash column chromatography (0 to 25% gradient of ethyl acetate in heptane) to afford the title compound (33.9 g) as a solid. LCMS (method 1): 243/245 (M+H)+; retention time: 0.95 min.

Step 2: Preparation of 5-bromo-3-ethylsulfanyl-pyridine-2-carboxylic acid

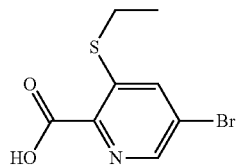

A solution of 5-bromo-3-ethylsulfanyl-pyridine-2-carbonitrile (43 g, 170 mmol, 1.0 eq.) in 800 ml aqueous hydrogen chloride HCl 32% was heated to 60° C. overnight. Dioxane (100 ml) was added and the mixture was further stirred at 60° C. for 48 h. The reaction mixture was cooled to 0-5° C., treated with an aqueous sodium hydroxide solution (NaOH 30%) until pH11 and washed with 2×200 ml tert-butyl methyl ether. The water phase was acidified with HCl 10% back to pH 4, the resulting solid was filtrated, washed with water and dried in vacuo. LCMS (method 1): 262, 264 (M+H)+; retention time: 0.77 min. ¹H NMR (400 MHz, CDCl₃) δ ppm: 8.50 (s, 1H); 8.06 (s, 1H); 3.03 (q, 2H); 1.24 (t, 3H).

Step 3: Preparation of methyl 5-bromo-3-ethylsulfanyl-pyridine-2-carboxylate

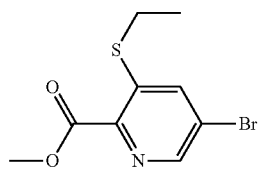

To a suspension of 5-bromo-3-ethylsulfanyl-pyridine-2-carboxylic acid (15.0 g, 57.23 mmol) in methanol (350 ml) was added sulfuric acid (0.5 ml) and the mixture stirred at reflux overnight. After cooling, the solution was concentrated under reduced pressure. The residue was triturated with diethyl ether (200 ml), the suspension filtered, the solid washed with cold diethyl ether and dried in vacuo to afford methyl 5-bromo-3-ethylsulfanyl-pyridine-2-carboxylate (13.9 g) as a solid, mp 72-74° C. LCMS (method 1): 276/278 (M+H)+, retention time 0.98 min. ¹H-NMR (CDCl₃, ppm) 1.42 (3H), 2.94 (2H), 4.00 (3H), 7.78 (1H), 8.46 (1H).

Step 4: Preparation of methyl 5-bromo-3-ethylsulfonyl-pyridine-2-carboxylate

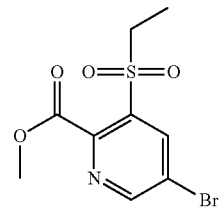 [SMILES: CCS(=O)(=O)c1cc(Br)cnc1C(=O)OC]

Methyl 5-bromo-3-ethylsulfanyl-pyridine-2-carboxylate (24.4 g, 88.4 mmol) was suspended in dichloromethane (250 mL), cooled to 00° C., and treated portion wise with mCPBA (37.6 g, 185.7 mmol). The mixture was stirred at ambient temperature for 18 hours. The mixture was diluted with water and dichloromethane, the aqueous phase was back extracted with dichloromethane (2×), and the combined organic phases washed with Na₂S₂O₄, dried over Na₂SO₄. Partial concentration of the solvent, led to a solid (the desired title compound) that was filtered. The filtrate was evaporated to dryness, which was purified by chromatography on silica to give further pure title compound as white solid. LCMS (method 3): 308/310 (M+H)+; retention time: 0.76 min. 1H NMR (d⁶-DMSO, 400 MHz): 9.08 (d, J=2.4 Hz, 1H), 8.58 (d, J=2.4 Hz, 1H), 3.87 (s, 3H), 3.52 (q, J=7.8 Hz, 2H), 1.18 (t, J=7.8 Hz, 3H).

Step 5: Preparation of methyl 5-(cyanomethyl)-3-ethylsulfonyl-pyridine-2-carboxylate

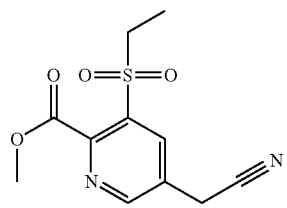 [SMILES: CCS(=O)(=O)c1cc(CC#N)cnc1C(=O)OC]

A solution of methyl 5-bromo-3-ethylsulfonyl-pyridine-2-carboxylate, (2.00 g, 6.49 mmol) in DMF (13.0 mL) was treated with TMS-acetonitrile (2.25 g, 2.71 mL, 19.5 mmol), difluorozinc (0.403 g, 3.89 mmol), XANTPHOS (0.153 g, 0.260 mmol) and Pd₂(dba)₃ (0.119 g, 0.130 mmol) under argon. The resulting mixture was stirred for 5 hours at 100° C. LCMS after this time showed no further reaction progression. The mixture was cooled, diluted with EtOAc, and filtered over hyflo. The filtrate was washed with water/ NH₄Cl, brine, dried over Na₂SO₄, filtered and concentrated in vacuo. The crude product was purified by combi flash chromatography with a column of 40 g and a gradient cyclohexane+0-50% ethylacetate. This gave the title compound as yellow oil. LCMS (method 3): 269 (M+H)+; retention time: 0.58 min. ¹H NMR (400 MHz, CDCl₃) δ ppm: 1.38 (t, J=7.5 Hz, 3H), 3.58 (q, J=7.5 Hz, 2H), 3.95 (s, 2H), 4.06 (s, 3H), 8.37 (d, J=2.20 Hz, 1H), 8.86 (d, J=2.20 Hz, 1H).

Step 6: Preparation of methyl 5-(1-cyanocyclopropyl)-3-ethylsulfonyl-pyridine-2-carboxylate

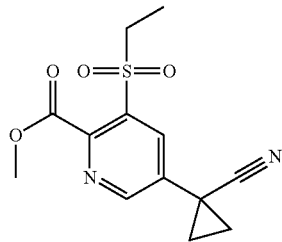 [SMILES: CCS(=O)(=O)c1cc(C2(C#N)CC2)cnc1C(=O)OC]

Methyl 5-(cyanomethyl)-3-ethylsulfonyl-pyridine-2-carboxylate (0.63 g, 2.3 mmol) was dissolved in acetonitrile (19 mL) and cesium carbonate (2.3 g, 7.0 mmol) was added to the colourless solution (solution darkened), followed by addition of 1,2-dibromoethane (0.90 g, 0.41 mL, 4.7 mmol) The brown solution was stirred at 80° C. bath temperature. LC/MS detected desired mass at Rt=0.73 min after 1.5 h. The reaction mixture was concentrated in vacuo and diluted with EtOAc and water. The organic layer was separated, washed successively with water and brine, dried over $Na_2SO_4$, filtered and concentrated in vacuo. The crude product was dissolved in dichloromethane and adsorbed onto TEFLON BULK SORBENTS. Purification over a silica gel cartridge (Rf200) eluting with Cyclohexane/EtOAc, gave the title compound as a beige resin. LCMS (method 3): 295 (M+H)+; retention time: 0.72 min. $^1$H NMR (400 MHz, $CDCl_3$) δ ppm: 1.36 (t, J=7.5 Hz, 3H), 1.57-1.62 (m, 2H), 1.95-2.00 (m, 2H), 2.05 (s, 2H), 4.04 (s, 4H), 8.13 (d, J=2.20 Hz, 1H), 8.87 (d, J=2.20 Hz, 1H).

Step 7: Preparation of 5-(1-cyanocyclopropyl)-3-ethylsulfonyl-pyridine-2-carboxylic acid

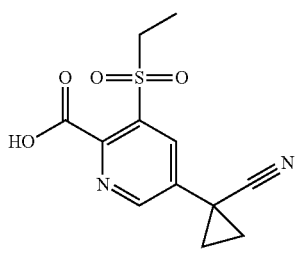 [SMILES: CCS(=O)(=O)c1cc(C2(C#N)CC2)cnc1C(=O)O]

A solution of methyl 5-(1-cyanocyclopropyl)-3-ethylsulfonyl-pyridine-2-carboxylate (0.27 g, 0.92 mmol) was dissolved in THF (4 mL) and water (1.5 mL) (red solution), and then treated with $LiOH.H_2O$ (0.058 g, 1.4 mmol). The mixture was stirred at ambient temperature for 2 hours by which time LCMS analysis showed reaction completion (only desired product at Rt=0.32 min, method 3). The THF was evaporated in vacuo and the residue was acidified with 1M HCl and extracted with EtOAc. The organic layer was washed with brine, dried over $Na_2SO_4$ filtrated and concentrated in vacuo to give pure title product as a beige solid. LCMS (method 3): 281 (M+H)+; retention time: 0.30 min. $^1$H NMR (400 MHz, methanol-$d_4$) δ ppm: 1.31 (t, J=7.3 Hz, 3H), 1.71-1.78 (m, 2H), 1.92-1.98 (m, 2H), 3.60 (q, J=7.3 Hz, 2H), 8.28 (d, J=2.20 Hz, 1H), 8.83 (d, J=2.20 Hz, 1H).

Step 8: Preparation of 5-(1-cyanocyclopropyl)-3-ethylsulfonyl-N-[2-(methylamino)-5-(trifluoromethyl)-3-pyridyl]pyridine-2-carboxamide

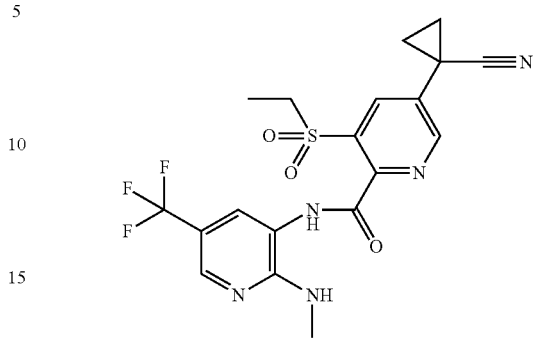

(a) 5-(1-cyanocyclopropyl)-3-ethylsulfonyl-pyridine-2-carbonyl chloride: obtained from 5-(1-cyanocyclopropyl)-3-ethylsulfonyl-pyridine-2-carboxylic acid (1.0 g, 3.57 mmol) and oxalyl chloride (0.405 ml, 4.64 mmol) in dichloromethane (15 ml) according to procedure Example P1, step 1. The mixture was stirred at ambient temperature for 2 hours, then evaporated to dryness to afford the acid chloride (1.06 g) as a solid.
(b) To a solution of N2-methyl-5-(trifluoromethyl)pyridine-2,3-diamine (600 mg, 3.14 mmol) and triethylamine (1.09 ml, 7.85 mmol) in dichloromethane (24 ml) at 0-5° C. was added a solution of 5-(1-cyanocyclopropyl)-3-ethylsulfonyl-pyridine-2-carbonyl chloride (1.03 g, 3.45 mmol) in dichloromethane (4 ml) dropwise. The reaction mixture was stirred at 0-5° C. for 30 minutes, then at ambient temperature overnight. Water was added to the mixture and the aqueous layer was extracted 3 times with dichloromethane. The combined organic layers were washed with water and brine, dried over $Na_2SO_4$, filtered and evaporated under vacuum. The crude was purified by flash chromatography over silicagel to give the title compound 5-(1-cyanocyclopropyl)-3-ethylsulfonyl-N-[2-(methylamino)-5-(trifluoromethyl)-3-pyridyl]pyridine-2-carboxamide (1.1 g) as a solid. LCMS (method 3): 454 (M+H)+; retention time: 0.91 min. $^1$H NMR (400 MHz, $CDCl_3$) δ ppm: 1.4 (t, J=7 Hz, 3H), 1.6-1.7 (m, 2H), 2.0-2.1 (m, 2H), 3.1 (d, J=5 Hz, 3H), 3.9 (q, J=7 Hz, 2H), 5.5 (d, J=4 Hz, 1H), 7.7 (d, J=4 Hz, 1H), 8.2 (d, J=2 Hz, 1H), 8.3 (s, 1H), 8.4 (s, 1H), 8.9 (d, J=3 Hz, 1H).

Step 9: Preparation of 1-[5-ethylsulfonyl-6-[3-methyl-6-(trifluoromethyl)imidazo[4,5-b]pyridin-2-yl]-3-pyridyl]cyclopropanecarbonitrile (compound P9)

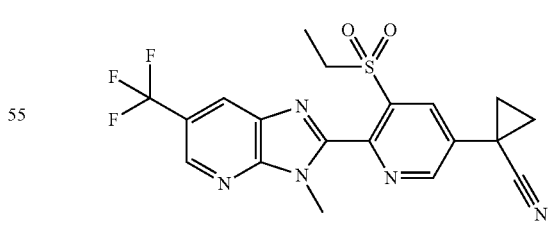

A solution of 5-(1-cyanocyclopropyl)-3-ethylsulfonyl-N-[2-(methylamino)-5-(trifluoromethyl)-3-pyridyl]pyridine-2-carboxamide (62 mg, 0.137 mmol) in glacial acetic acid (1.5 mL) was heated in the microwave at 150° C. for 20 minutes. The reaction mixture was poured into water (10 ml) and the resulting suspension stirred at ambient temperature for 20 minutes. The precipitate formed was filtered and washed 3 times with water. The solid was dried under vacuum at 50°

C. to give the title compound 1-[5-ethylsulfonyl-6-[3-methyl-6-(trifluoromethyl)imidazo[4,5-b]pyridin-2-yl]-3-pyridyl]cyclopropanecarbonitrile (compound P9) as a white solid (40 mg), mp 171-173° C. LCMS (method 3): 436 (M+H)+; retention time: 0.98 min. $^1$H NMR (400 MHz, CDCl$_3$) δ ppm: 1.4 (t, J=7 Hz, 3H), 1.7-1.7 (m, 2H), 2.0-2.1 (m, 2H), 3.9-4.0 (q, 2H), 3.93 (s, 3H), 8.3 (d, J=2 Hz, 1H), 8.3 (d, J=1 Hz, 1H), 8.8 (d, J=1 Hz, 1H), 9.1 (d, J=2 Hz, 1H).

Example P6: Preparation of 1-[5-ethylsulfonyl-6-[3-methyl-6-(trifluoromethyl)imidazo[4,5-b]pyridin-2-yl]-3-pyridyl]cyclopropanecarboxamide (compound P11)

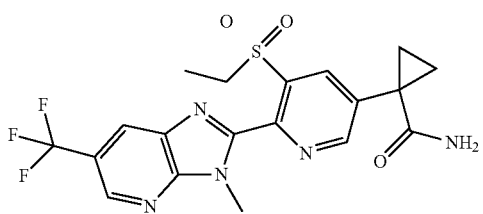

To a suspension of 1-[5-ethylsulfonyl-6-[3-methyl-6-(trifluoromethyl)imidazo[4,5-b]pyridin-2-yl]-3-pyridyl]cyclopropanecarbonitrile (90 mg, 0.207 mmol) in methanol (4 mL) at ambient temperature was added an aqueous 4M solution of sodium hydroxide (0.258 mL, 1.034 mmol). The reaction mixture was stirred 5 hours at 60° C. and one night at ambient temperature. The mixture was evaporated under vacuum and the residue dissolved in dichloromethane. Water was added, the layers separated and the aqueous phase extracted three times with dichloromethane. The combined organic layers were washed with brine, dried over Na$_2$SO$_4$, filtered and evaporated. The crude was purified by flash chromatography over silicagel to give 1-[5-ethylsulfonyl-6-[3-methyl-6-(trifluoromethyl)imidazo[4,5-b]pyridin-2-yl]-3-pyridyl]cyclopropanecarboxamide (compound P11) as a solid (35 mg), mp 215-217° C. LCMS (method 3): 454 (M+H)+; retention time: 0.87 min. $^1$H NMR (400 MHz, CDCl$_3$) δ ppm: 1.3-1.4 (m, 2H), 1.4-1.5 (t, 3H), 1.8-1.9 (m, 2H), 3.9-3.9 (q, 2H), 4.0 (s, 3H), 5.3 (br s, 1H), 5.7 (br s, 1H), 8.3 (d, J=1 Hz, 1H), 8.6 (d, J=2 Hz, 1H), 8.8 (d, J=1 Hz, 1H), 9.1 (d, J=2 Hz, 1H).

Example P7: Preparation of 2-(6-cyclopropyl-3-ethylsulfonyl-2-pyridyl)-3-methyl-6-(trifluoromethyl)imidazo[4,5-b]pyridine (compound P14)

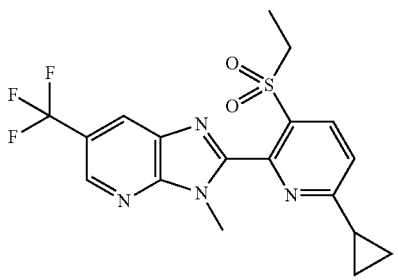 [SMILES: CCS(=O)(=O)c1ccc(C2CC2)nc1-c1nc2cc(C(F)(F)F)cnc2n1C]

A solution of 2-(6-chloro-3-ethylsulfonyl-2-pyridyl)-3-methyl-6-(trifluoromethyl)imidazo[4,5-b]pyridine (250 mg, 0.618 mmol), 2M aqueous sodium carbonate (0.926 ml, 1.853 mmol) and cyclopropylboronic acid (106 mg, 1.235 mmol) in 1,2-dimethoxyethane (4 ml) was purged with argon for 10 minutes. Bis(triphenylphosphine) palladium(II) dichloride (4.3 mg, 0.01 eq.) was added and the mixture heated in the microwave at 110° C. for 40 minutes. The mixture was diluted with ethyl acetate, washed with water (3×), the combined organic phases washed with brine, dried over sodium sulfate, filtrated and evaporated. The residue was purified by column chromatography over silica gel (cyclohexane/ethyl acetate 1:1) to afford the title compound P14 as a solid, mp 163-165° C. LCMS (method 3): 411 (M+H)+; retention time: 1.07 min. $^1$H NMR (400 MHz, CDCl$_3$) δ ppm: 1.18 (m, 4H), 1.35 (t, 3H), 2.21 (m, 1H), 3.77 (q, 2H), 3.83 (s, 3H), 7.52 (d, J=8.44 Hz, 1H), 8.29 (s, 1H), 8.31 (d, J=8.44 Hz, 1H), 8.75 (s, 1H).

Example P8: Preparation of 1-[5-ethylsulfonyl-6-[3-methyl-6-(trifluoromethyl)imidazo[4,5-b]pyridin-2-yl]-3-pyridyl]cyclopropanecarboxylic acid (compound P12)

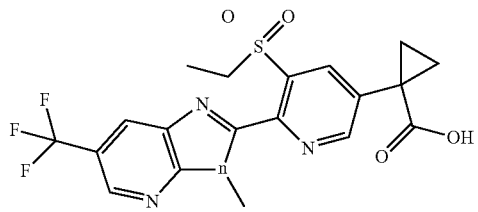

To a suspension of 1-[5-ethylsulfonyl-6-[3-methyl-6-(trifluoromethyl)imidazo[4,5-b]pyridin-2-yl]-3-pyridyl]cyclopropanecarbonitrile (90 mg, 0.207 mmol) in methanol (4 mL) at ambient temperature was added an aqueous 4M solution of sodium hydroxide (0.258 mL, 1.034 mmol). The reaction mixture was stirred 5 hours at 60° C. and one night at ambient temperature. The mixture was evaporated under vacuum and the residue dissolved in dichloromethane. Water was added, the layers separated and the aqueous phase extracted three times with dichloromethane. The aqueous layer was acidified until pH 1 and extracted with dichloromethane. The organic layer was dried over Na$_2$SO$_4$, filtered and evaporated to give 1-[5-ethylsulfonyl-6-[3-methyl-6-(trifluoromethyl)imidazo[4,5-b]pyridin-2-yl]-3-pyridyl]cyclopropanecarboxylic acid (compound P12) as a gum. LCMS (method 3): 455 (M+H)+; retention time: 0.91 min.

$^1$H NMR (400 MHz, CDCl$_3$) δ ppm: 1.3 (t, J=7 Hz, 3H), 1.4-1.5 (m, 2H), 1.9-2.0 (m, 2H), 3.6 (q, J=7 Hz, 2H), 3.9 (s, 3H), 5.3 (s, 1H), 8.4 (d, J=2 Hz, 1H), 8.5 (d, J=1 Hz, 1H), 8.8 (d, J=1 Hz, 1H), 8.9 (d, J=2 Hz, 1H).

Example P9: Preparation of 1-[5-ethylsulfonyl-6-[3-methyl-6-(trifluoromethylsulfanyl)imidazo[4,5-b]pyridin-2-yl]-3-pyridyl]cyclopropanecarbonitrile (compound P13)

Step 1: Preparation of 5-(1-cyanocyclopropyl)-3-ethylsulfonyl-N-[2-(methylamino)-5-(trifluoromethylsulfanyl)-3-pyridyl]pyridine-2-carboxamide

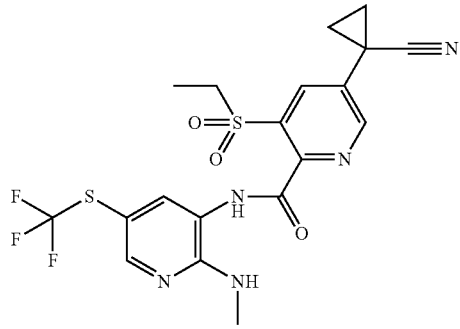 [SMILES: CCS(=O)(=O)c1cc(C2(C#N)CC2)cnc1C(=O)Nc1cc(SC(F)(F)F)cnc1NC]

To a solution of N2-methyl-5-(trifluoromethylsulfanyl) pyridine-2,3-diamine (100 mg, 0.448 mmol) and triethylamine (0.158 ml, 1.12 mmol) in ethyl acetate (5 ml) at 0-5° C. was added a solution of 5-(1-cyanocyclopropyl)-3-ethylsulfonyl-pyridine-2-carbonyl chloride [prepared according to Example P5, step 8(a) from 5-(1-cyanocyclopropyl)-3-ethylsulfonyl-pyridine-2-carboxylic acid (126 mg, 0.448 mmol) and oxalyl chloride (0.0718 ml, 0.806 mmol) in dichloromethane (5 ml)] in tetrahydrofuran (3 ml) dropwise. The reaction mixture was stirred at ambient temperature for 30 minutes. The suspension was poured into aqueous NaHCO$_3$ and the mixture extracted with ethyl acetate. The combined organic layers were washed with aqueous 1N HCl and brine, dried over magnesium sulfate, filtered and concentrated under vacuum to afford 5-(1-cyanocyclopropyl)-3-ethylsulfonyl-N-[2-(methylamino)-5-(trifluoromethylsulfanyl)-3-pyridyl]pyridine-2-carboxamide as a solid. This material was used without further purification. LCMS (method 3): 486 (M+H)+; retention time: 0.97 min.

Step 2: Preparation of 1-[5-ethylsulfonyl-6-[3-methyl-6-(trifluoromethylsulfanyl)imidazo[4,5-b]pyridin-2-yl]-3-pyridyl]cyclopropanecarbonitrile (compound P13)

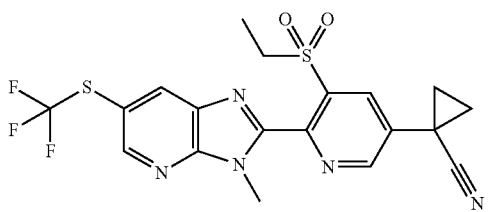 [SMILES: CCS(=O)(=O)c1cc(C2(C#N)CC2)cnc1-c1nc2cc(SC(F)(F)F)cnc2n1C]

Obtained from 5-(1-cyanocyclopropyl)-3-ethylsulfonyl-N-[2-(methylamino)-5-(trifluoromethylsulfanyl)-3-pyridyl] pyridine-2-carboxamide (218 mg, 0.448 mmol) in glacial acetic acid (2.6 ml) according to procedure Example P5, step 9. The solution was heated in the microwave at 150° C. for 30 minutes. The reaction mixture was poured into water and aqueous 1N NaOH added until formation of a precipitate. The solid was filtered and dried under vacuum, then purified by column chromatography over silica gel (0-35% gradient ethyl acetate in cyclohexane) to afford 1-[5-ethylsulfonyl-6-[3-methyl-6-(trifluoro-methylsulfanyl)imidazo[4,5-b]pyridin-2-yl]-3-pyridyl]cyclopropanecarbonitrile (compound P13) as a solid, mp 172.3-172.5. LCMS (method 3): 468 (M+H)+; retention time: 1.03 min.

$^1$H NMR (400 MHz, CDCl$_3$) δ ppm: 1.38 (t, J=7.52 Hz, 3H), 1.65-1.71 (m, 2H), 2.01-2.08 (m, 2H), 3.88 (s, 3H), 3.91 (q, J=7.52 Hz, 2H), 8.25 (d, J=2.20 Hz, 1H), 8.37 (d, J=1.83 Hz, 1H), 8.71 (d, J=1.83 Hz, 1H), 9.05 (d, J=2.20 Hz, 1H).

Example P10: Preparation of 1-[5-ethylsulfonyl-6-[3-methyl-6-(trifluoromethyl)imidazo[4,5-b]pyridin-2-yl]-2-pyridyl]cyclopropanecarbonitrile (compound P15)

Step 1: Preparation of 2-[5-ethylsulfonyl-6-[3-methyl-6-(trifluoromethyl)imidazo[4,5-b]pyridin-2-yl]-2-pyridyl]acetonitrile

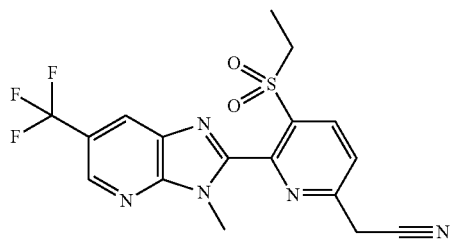 [SMILES: CCS(=O)(=O)c1ccc(CC#N)nc1-c1nc2cc(C(F)(F)F)cnc2n1C]

A solution of 2-(6-chloro-3-ethylsulfonyl-2-pyridyl)-3-methyl-6-(trifluoromethyl)imidazo[4,5-b]pyridine (500 mg, 1.235 mmol) in DMF (5 ml) was purged with argon for 10 minutes, then treated with TMS-acetonitrile (210 mg, 0.254 ml, 1.853 mmol), difluorozinc (76.6 mg, 0.741 mmol), Xantphos (28.6 mg, 0.049 mmol) and Pd$_2$(dba)$_3$ (22.6 mg, 0.025 mmol) under argon. The resulting mixture was heated in the microwave at 140° C. for 30 minutes. The reaction mixture was cooled, diluted with ethyl acetate and filtered over hyflo. The filtrate was washed with water and brine, dried over sodium sulfate, filtered and evaporated in vacuo. The residue was purified by flash column chromatography over silica gel (dichloromethane/ethyl acetate 5:1) to afford of 2-[5-ethylsulfonyl-6-[3-methyl-6-(trifluoromethyl) imidazo[4,5-b]pyridin-2-yl]-2-pyridyl]acetonitrile as a solid. LCMS (method 3): 410 (M+H)+; retention time: 0.91 min.
$^1$H NMR (400 MHz, CDCl$_3$) δ ppm: 1.38 (t, J=7.52 Hz, 3H), 3.86 (q, J=7.52 Hz, 2H), 3.92 (s, 3H), 4.13 (s, 2H), 7.84 (d, J=8.07 Hz, 1H), 8.32 (d, J=1.47 Hz, 1H), 8.60 (d, J=8.07 Hz, 1H), 8.78 (d, J=1.47 Hz, 1H).

Step 2: Preparation of 1-[5-ethylsulfonyl-6-[3-methyl-6-(trifluoromethyl)imidazo[4,5-b]pyridin-2-yl]-2-pyridyl]cyclopropanecarbonitrile (compound P15)

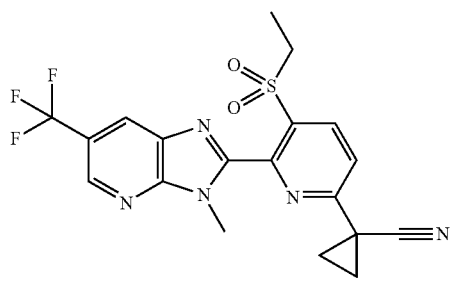 [SMILES: CCS(=O)(=O)c1ccc(C2(C#N)CC2)nc1-c1nc2cc(C(F)(F)F)cnc2n1C]

To a solution of 2-[5-ethylsulfonyl-6-[3-methyl-6-(trifluoromethyl)imidazo[4,5-b]pyridin-2-yl]-2-pyridyl]acetonitrile (100 mg, 0.244 mmol) and cesium carbonate (240 mg, 0.733 mmol) in acetonitrile (2.55 ml) was added 1,2-dibromoethane (92 mg, 0.042 ml, 0.489 mmol). The reaction mixture was heated at 80° C. for 30 minutes, then concentrated in vacuo. The mixture was diluted with ethyl acetate and water, the layers separated, the organic phase washed with water (3×) and brine, dried over sodium sulfate, filtrated and evaporated. The residue was purified by column chromatography over silica gel (cyclohexane/ethyl acetate 2:1) to afford 1-[5-ethylsulfonyl-6-[3-methyl-6-(trifluoromethyl)imidazo[4,5-b]pyridin-2-yl]-2-pyridyl]cyclopropanecarbonitrile (compound P15) as a gum. LCMS (method 3): 436 (M+H)+; retention time: 1.01 min. $^1$H NMR (400 MHz, CDCl$_3$) δ ppm: 1.36 (t, J=7.52 Hz, 3H), 1.92 (m, 4H), 3.78 (q, J=7.52 Hz, 2H), 3.81 (s, 3H), 8.12 (d, J=8.41 Hz, 1H), 8.30 (d, J=1.47 Hz, 1H), 8.52 (d, J=8.41 Hz, 1H), 8.77 (d, J=1.83, 1.47 Hz, 1H).

TABLE P

Examples of compounds of formula (I)
The compounds in Table P can be prepared as described in the examples above or similar methodology.

| Compound No. | Structures | Melting Point | MS/NMR |
|---|---|---|---|
| P1 | 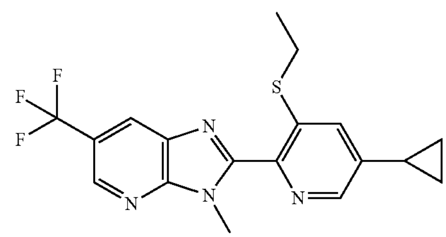 [SMILES: CCSc1cc(C2CC2)cnc1-c1nc2cc(C(F)(F)F)cnc2n1C] | 119-121° C. | LCMS (method 1): 379 (M + H)$^+$ retention time: 3.76 min |
| P2 | 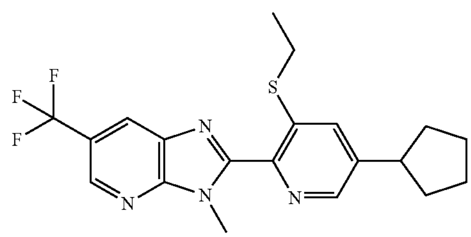 [SMILES: CCSc1cc(C2CCCC2)cnc1-c1nc2cc(C(F)(F)F)cnc2n1C] | 130-132° C. | LCMS (method 1): 407 (M + H)$^+$ retention time: 4.28 min |
| P3 | 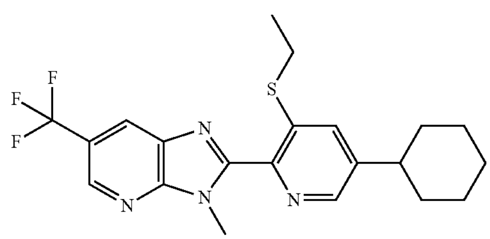 [SMILES: CCSc1cc(C2CCCCC2)cnc1-c1nc2cc(C(F)(F)F)cnc2n1C] | 148-150° C. | LCMS (method 1): 421 (M + H)$^+$ retention time: 4.52 min |
| P4 | 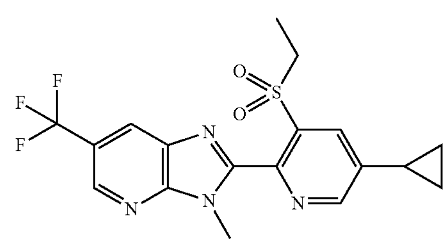 [SMILES: CCS(=O)(=O)c1cc(C2CC2)cnc1-c1nc2cc(C(F)(F)F)cnc2n1C] | sticky solid | LCMS (method 1): 411 (M + H)$^+$ retention time: 3.47 min |
| P5 | 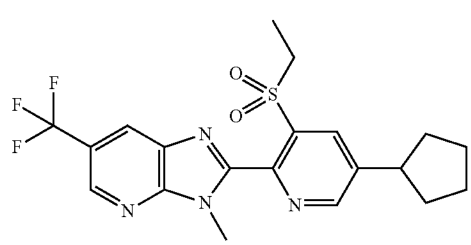 [SMILES: CCS(=O)(=O)c1cc(C2CCCC2)cnc1-c1nc2cc(C(F)(F)F)cnc2n1C] | 146-148° C. | LCMS (method 2): 439 (M + H)$^+$ retention time: 1.76 min |

TABLE P-continued

| Compound No. | Structures | Mp | LCMS |
|---|---|---|---|
| P6 | | 140-142° C. | LCMS (method 1): 453 (M + H)+ retention time: 3.88 min |

| Compound No. | Structures | LCMS R_t (min) | [M + H]+ (measured) | Method | Mp (° C.) |
|---|---|---|---|---|---|
| P7 | 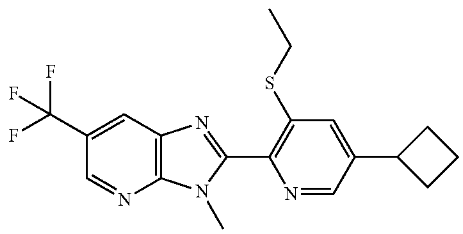 [SMILES: CCSc1cc(C2CCC2)cnc1-c1nc2cc(C(F)(F)F)cnc2n1C] | 4.05 | 393 | 1 | 136-138 |
| P8 | 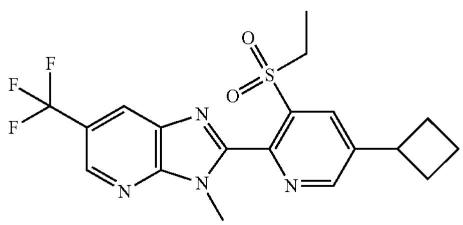 [SMILES: CCS(=O)(=O)c1cc(C2CCC2)cnc1-c1nc2cc(C(F)(F)F)cnc2n1C] | 3.63 | 425 | 1 | 130-132 |
| P9 | 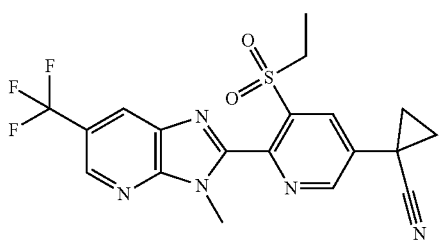 [SMILES: CCS(=O)(=O)c1cc(C2(C#N)CC2)cnc1-c1nc2cc(C(F)(F)F)cnc2n1C] | 0.98 | 436 | 3 | 171-173 |
| P10 | 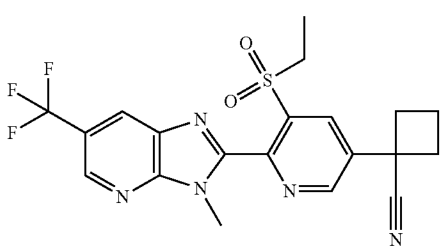 [SMILES: CCS(=O)(=O)c1cc(C2(C#N)CCC2)cnc1-c1nc2cc(C(F)(F)F)cnc2n1C] | 1.02 | 450 | 3 | gum |
| P11 | 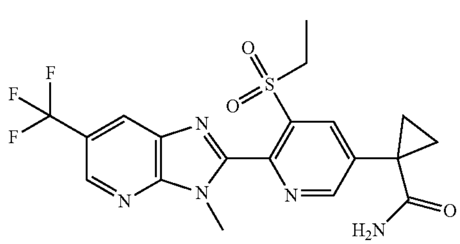 [SMILES: CCS(=O)(=O)c1cc(C2(C(N)=O)CC2)cnc1-c1nc2cc(C(F)(F)F)cnc2n1C] | 0.87 | 454 | 3 | 215-217 |

TABLE P-continued

| | | | | | |
|---|---|---|---|---|---|
| P12 | [structure] | 0.91 | 455 | 3 | gum |
| P13 | [structure] | 1.03 | 468 | 3 | 172.3-172.5 |
| P14 | [structure] | 1.07 | 411 | 3 | 163-165 |
| P15 | [structure] | 1.01 | 436 | 3 | gum |

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables 1 to 18 and Table P of the present invention"): an adjuvant selected from the group of substances consisting of petroleum oils (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin 1 (696)+TX, cinerin II (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinactin (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram [CCN]+TX, disulfoton (278)+TX, DNOC (282)+TX, dofenapyn (1113)+TX, doramectin [CCN]+TX, endosulfan (294)+TX, endothion (1121)+TX, EPN (297)+TX, eprinomectin [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad+TX, fen-pyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin 1 (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+TX, nifluridide (1309)+TX, nikkomycins [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin 1 (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos+TX, selamectin [CCN]+TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+TX, tetranactin (653)+TX, tetrasul (1425)+TX, thiafenox+TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of *Adoxophyes orana* GV (12)+TX, *Agrobacterium radiobacter* (13)+TX, *Amblyseius* spp. (19)+TX, *Anagrapha falcifera* NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, *Bacillus firmus* (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (53)+TX, *Beauveria brongniartii* (54)+TX, *Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, *Helicoverpa zea* NPV (431)+TX, *Heterorhabditis bacteriophora* and *H. megidis* (433)+TX, *Hippodamia convergens* (442)+TX, *Leptomastix dactylopii* (488)+TX, *Macrolophus caliginosus* (491)+TX, *Mamestra brassicae* NPV (494)+TX, *Metaphycus helvolus* (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (575)+TX, *Orius* spp. (596)+TX, *Paecilomyces fumosoroseus* (613)+TX, *Phytoseiulus persimilis* (644)+TX, *Spodoptera exigua* multicapsid nuclear polyhedrosis virus (scientific name) (741)+TX, *Steinernema bibionis* (742)+TX, *Steinernema carpocapsae* (742)+TX, *Steinernema feltiae* (742)+TX, *Steinernema glaseri* (742)+TX, *Steinernema riobrave* (742)+TX, *Steinernema riobravis* (742)+TX, *Steinernema scapterisci* (742)+TX, *Steinernema* spp. (742)+TX, *Trichogramma* spp. (826)+TX, *Typhlodromus occidentalis* (844) and *Verticillium lecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CCN]+TX, diflubenzuron (250)+TX, dimatif [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlure I (421)+TX, grandlure II (421)+TX, grandlure III (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone [CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure B$_1$ (839)+TX, trimedlure B$_2$ (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin [CCN]+TX, allyxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, *Bacillus thuringiensis* delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin [CCN]+TX, jasmolin 1 (696)+TX, jasmolin II (696)+TX, jodfenphos (1248)+TX, juvenile hormone I [CCN]+TX, juvenile hormone II [CCN]+TX, juvenile hormone III [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquinbutyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metoflutrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex (1294)+TX, monocrotophos (561)+TX, morphothion (1300)+TX, moxidectin [CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene III [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin 1 (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, *Myrothecium verrucaria* composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebucon-azole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a, 12,12a, 12b-decahydro-6,12-dihydroxy-4,6a, 12b-trimethyl-11-oxo-9-(3-pyridinyl)-2H, 11Hnaphtho[2,1-b]pyrano[3,4-e]pyran-4-yl]methyl-cyclopropanecarboxylate [915972-17-7]+TX, 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide [926914-55-8]+TX, flufiprole [704886-18-0]+TX, cyclaniliprole [1031756-98-5]+TX, tetraniliprole [1229654-66-3]+TX, guadipyr (described in WO2010/060231)+TX and
cycloxaprid (described in WO 2005/077934)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright @ 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used. "CAS Reg. No" means the Chemical Abstracts Registry Number.

The active ingredient mixture of the compounds of formula I selected from Tables 1 to 18 and Table P with active ingredients described above comprises a compound selected from Tables 1 to 18 and Table P and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1 to 18 and Table P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 18 and Table P and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

Example B1: Activity Against *Spodoptera littoralis* (Egyptian Cotton Leaf Worm)

Cotton leaf discs were placed on agar in 24-well microtiter plates and sprayed with aqueous test solutions prepared from 10,000 ppm DMSO stock solutions. After drying the leaf discs were infested with five L1 larvae. The samples were assessed for mortality, anti-feedant effect, and growth inhibition in comparison to untreated samples 3 days after infestation. Control of *Spodoptera littoralis* by a test sample is when at least one of mortality, anti-feedant effect, and growth inhibition is higher than the untreated sample. The following compound gave an effect of at least 80% control in at least one of the three categories (mortality, anti-feedancy or growth inhibition) at an application rate of 200 ppm: P1, P4, P5, P8, P9, P10, P12 and P13.

Example B2: Activity Against *Spodoptera littoralis* (Egyptian Cotton Leaf Worm)

Test compounds were applied by pipette from 10,000 ppm DMSO stock solutions into 24-well plates and mixed with agar. Lettuce seeds were placed on the agar and the multi well plate was closed by another plate which contains also agar. After 7 days the roots have absorbed the compound and the lettuce has grown into the lid plate. The lettuce leafs were now cut off into the lid plate. *Spodoptera* eggs were pipetted through a plastic stencil on a humid gel blotting paper and the plate closed with it. The samples were assessed for mortality, anti-feedant effect and growth inhibition in comparison to untreated samples 6 days after infestation. The following compound gave an effect of at least 80% control in at least one of the three categories (mortality, anti-feedancy or growth inhibition) at an application rate of 12.5 ppm: P1, P4, P9, P12 and P13.

Example B3: Activity Against *Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation. The following compound gave an effect of at least 80% in at least one of the two categories (mortality or growth inhibition) at an application rate of 200 ppm: P1, P4, P5, P6, P8, P9, P10, P11, P12 and P13.

Example B4: Activity Against *Diabrotica balteata* (Corn Root Worm)

Maize sprouts, placed on an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation. The following compounds gave an effect of at least 80% in at least one of the two categories (mortality or growth inhibition) at an application rate of 200 ppm: P1, P4, P5, P6, P8, P9, P10, P11, P12 and P13.

Example B5: Activity Against *Myzus persicae* (Green Peach Aphid)

Sunflower leaf discs were placed on agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation. The following compound resulted in at least 80% mortality at an application rate of 200 ppm: P1, P4, P5, P6, P8, P9, P10, P11, P12 and P13.

Example B6: Activity Against *Myzus persicae* (Green Peach Aphid)

Test compounds from 10,000 ppm DMSO stock solutions were applied by pipette into 24-well microtiter plates and mixed with sucrose solution. The plates were closed with a stretched Parafilm. A plastic stencil with 24 holes was placed onto the plate and infested pea seedlings were placed directly on the Parafilm. The infested plate was closed with a gel blotting paper and another plastic stencil and then turned upside down. The samples were assessed for mortality 5 days after infestation.
The following compounds resulted in at least 80% mortality at a test rate of 12 ppm: P1.

Example B7: Activity Against *Bemisia tabaci* (Cotton White Fly)

Cotton leaf discs were placed on agar in 24-well microtiter plates and sprayed with aqueous test solutions prepared from 10,000 ppm DMSO stock solutions. After drying the leaf discs were infested with adult white flies. The samples were checked for mortality 6 days after incubation. The following compound resulted in at least 80% mortality at an application rate of 200 ppm: P4, P6, P8, P9, P10, P11, P12 and P13.

Example B8: Activity Against *Euschistus heros* (Neotropical Brown Stink Bug)

Soybean leaf on agar in 24-well microtiter plates were sprayed with aqueous test solutions prepared from 10,000 ppm DMSO stock solutions. After drying the leaf were infested with N-2 nymphs. The samples were assessed for mortality 5 days after infestation. The following compound resulted in at least 80% mortality at an application rate of 200 ppm: P1, P4, P5, P6, P8, P9, P10, P11, P12 and P13.

Example B9: Activity Against *Myzus persicae* (Green Peach Aphid)

Roots of pea seedlings infested with an aphid population of mixed ages were placed directly into aqueous test solutions prepared from 10,000 DMSO stock solutions. The samples were assessed for mortality 6 days after placing seedlings into test solutions.
The following compounds resulted in at least 80% mortality at a test rate of 24 ppm: P9 and P11.

Example B10: Activity Against *Frankliniella occidentalis* (Western Flower *Thrips*)

Sunflower leaf discs were placed on agar in 24-well microtiter plates and sprayed with aqueous test solutions prepared from 10,000 DMSO stock solutions. After drying the leaf discs were infested with a *Frankliniella* population of mixed ages. The samples were assessed for mortality 7 days after infestation. The following compounds resulted in at least 80% mortality at an application rate of 200 ppm: P4, P9, P11 and P13.

Example B11: Activity Against *Thrips tabaci* (Onion *Thrips*)

Sunflower leaf discs were placed on agar in 24-well microtiter plates and sprayed with aqueous test solutions prepared from 10,000 ppm DMSO stock solutions. After drying the leaf discs were infested with a *thrips* population of mixed ages. The samples were assessed for mortality 6 days after infestation. The following compounds resulted in at least 80% mortality at an application rate of 200 ppm: P9 and P13.

Example B12: Activity Against *Aedes aegypti* (Yellow Fever Mosquito)

Test solutions, at an application rate of 200 ppm in ethanol, were applied to 12 well tissue culture plates. Once the deposits were dry, five, two to five day old adult female *Aedes aegypti* were added to each well, and sustained with a 10% sucrose solution in a cotton wool plug. Assessment of knockdown was made one hour after introduction, and mortality was assessed at 24 and 48 hours after introduction. The following compounds gave at least 80% control of *Aedes aegypti* after 48 h and/or 24 h: P9 and P13.

Example B13: Activity Against *Anopheles stephensi* (Indian Malaria Mosquito)

Test solutions, at an application rate of 200 ppm in ethanol, were applied to 12 well tissue culture plates. Once the deposits were dry, five, two to five day old adult female *Anopheles stephensi* were added to each well, and sustained with a 10% sucrose solution in a cotton wool plug. Assessment of knockdown was made one hour after introduction, and mortality was assessed at 24 and 48 hours after introduction. The following compounds gave at least 80% control of *Anopheles stephensi* after 48 h and/or 24 h: P4, P9 and P13.

The invention claimed is:
1. A compound of formula I

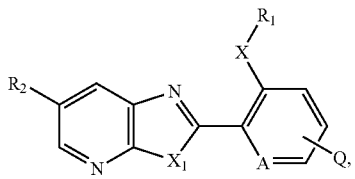

wherein
A represents CH or N;
Q is attached to the 3- or 4-position; and is $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, $C_3$-$C_6$cycloalkyl, —C(O)OH, —C(O)NH$_2$, phenyl and phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and —C(O)$C_1$-$C_4$haloalkyl;
X is S, SO or SO$_2$;
$R_1$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl or $C_3$-$C_6$cycloalkyl mono- or polysubstituted by substituents selected from the group consisting of halogen, cyano and $C_1$-$C_4$alkyl; or
$R_1$ is $C_3$-$C_6$cycloalkyl-$C_1$-$C_4$alkyl mono- or polysubstituted by substituents selected from the group consisting of halogen, cyano and $C_1$-$C_4$alkyl; or
$R_1$ is $C_2$-$C_6$alkenyl, $C_2$-$C_6$haloalkenyl or $C_2$-$C_6$alkynyl;
$R_2$ is halogen, cyano, $C_1$-$C_6$haloalkyl or $C_1$-$C_6$haloalkyl substituted by one or two substituents selected from the group consisting of hydroxyl, methoxy and cyano; or
$R_2$ is $C_1$-$C_4$haloalkylsulfanyl, $C_1$-$C_4$haloalkylsulfinyl, $C_1$-$C_4$haloalkylsulfonyl, O($C_1$-$C_4$haloalkyl), or —C(O)$C_1$-$C_4$haloalkyl; or
$R_2$ is $C_3$-$C_6$cycloalkyl which can be mono- or polysubstituted by substituents selected from the group consisting of halogen, cyano and $C_1$-$C_4$alkyl;
$X_1$ is O, S or NR$_3$, wherein R$_3$ is hydrogen, $C_1$-$C_4$alkyl, $C_2$-$C_6$alkenyl, $C_2$-$C_6$alkynyl, $C_1$-$C_4$alkoxy-$C_1$-$C_4$alkyl or $C_3$-$C_6$cycloalkyl; or an agrochemically acceptable salt, a stereoisomer, an enantiomer, a tautomer or an N-oxide of a compound of formula I.

2. The compound of claim 1, represented by the compounds of formula I-1

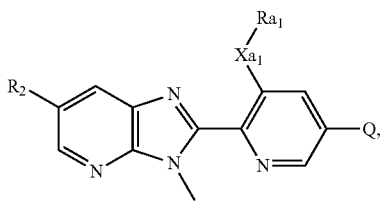

wherein R$_2$ and Q are as defined under formula I in claim 1;
Xa$_1$ is S, SO or SO$_2$; and
Ra$_1$ is methyl, ethyl, n-propyl, i-propyl or cyclopropylmethyl.

3. The compound of claim 1, represented by the compounds of formula I-2

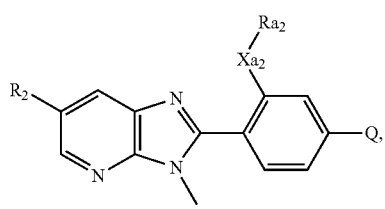

wherein R$_2$ and Q are as defined under formula I in claim 1;
Xa$_2$ is S, SO or SO$_2$; and
Ra$_2$ is methyl, ethyl, n-propyl, i-propyl or cyclopropylmethyl.

4. The compound of claim 1, represented by the compounds of formula I-3

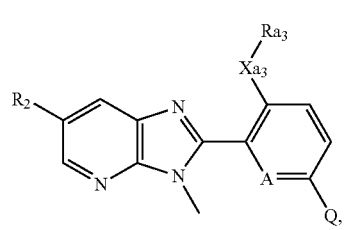

wherein R$_2$ and Q are as defined under formula I in claim 1;
Xa$_3$ is S, SO or SO$_2$; and
Ra$_3$ is methyl, ethyl, n-propyl, i-propyl or cyclopropylmethyl.

5. The compound of claim 1, represented by the compounds of formula Ia-1

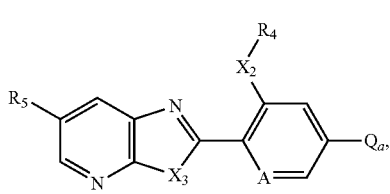

wherein
A is CH or N;
$X_2$ is S or SO$_2$;
$X_3$ is N—($C_1$-$C_4$alkyl);
$R_4$ is $C_1$-$C_4$alkyl;
$R_5$ is $C_1$-$C_4$haloalkyl or $C_1$-$C_4$haloalkylsulfanyl; and
$Q_a$ is $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, —C(O)OH and —C(O)NH$_2$.

6. The compound of claim 1, represented by the compounds of formula Ia-2

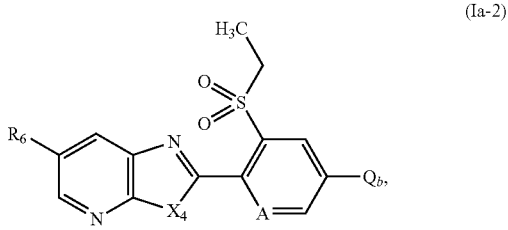

(Ia-2)

wherein
A is CH or N;
$X_4$ is N—($C_1$-$C_4$alkyl);
$R_6$ is $C_1$-$C_4$haloalkyl or $C_1$-$C_4$haloalkylsulfanyl; and
$Q_b$ is $C_3$-$C_6$cycloalkyl, or $C_3$-$C_6$cycloalkyl monosubstituted by substituents selected from the group consisting of cyano, —C(O)OH and —C(O)NH$_2$.

7. The compound of claim 1, represented by the compounds of formula Ia-3

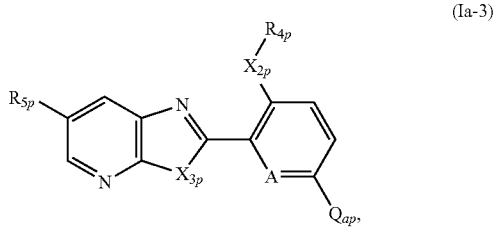

(Ia-3)

wherein
A is CH or N;
$X_{2p}$ is S or SO$_2$;
$X_{3p}$ is N—($C_1$-$C_4$alkyl);
$R_{4p}$ is $C_1$-$C_4$alkyl;
$R_{5p}$ is $C_1$-$C_4$haloalkyl or $C_1$-$C_4$haloalkylsulfanyl; and
$Q_{ap}$ is $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, —C(O)OH, —C(O)NH$_2$ and phenyl.

8. The compound of claim 1, represented by the compounds of formula Ia-4

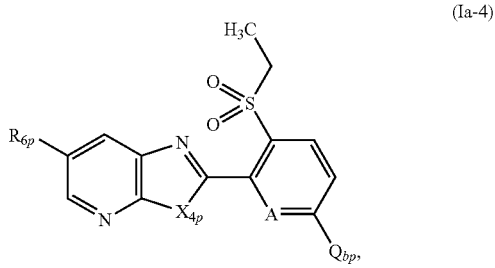

(Ia-4)

wherein
A is CH or N;
$X_{4p}$ is N—($C_1$-$C_4$alkyl);
$R_{6p}$ is $C_1$-$C_4$haloalkyl or $C_1$-$C_4$haloalkylsulfanyl; and
$Q_{bp}$ is $C_3$-$C_6$cycloalkyl, or $C_3$-$C_6$cycloalkyl monosubstituted by substituents selected from the group consisting of cyano, —C(O)OH and —C(O)NH$_2$.

9. The compound of claim 1, represented by a compound of formula VI-a

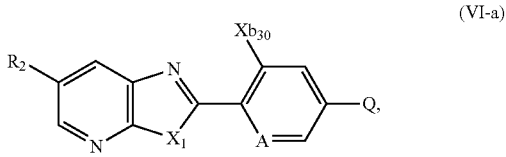

(VI-a)

wherein
A, Q, $X_1$ and $R_2$ are as defined under formula I in claim 1; and
$Xb_{30}$ is halogen.

10. A pesticidal composition, which comprises at least one compound of formula I according to claim 1 or a tautomer thereof, in each case in free form or in agrochemically utilizable salt form, as active ingredient and at least one auxiliary.

11. A method for controlling pests, which comprises applying a composition according to claim 10 the pests or their environment with the exception of a method for treatment of the human or animal body by surgery or therapy and diagnostic methods practised on the human or animal body.

12. A method for the protection of plant propagation material from the attack by pests, which comprises treating the propagation material or the site, where the propagation material B is planted, with a composition according to claim 10.

13. Plant propagation material treated in accordance with the method described in claim 12.

14. The compound of claim 1, wherein $R_2$ is halogen, cyano, $C_1$-$C_6$haloalkyl or $C_1$-$C_6$haloalkyl substituted by one or two substituents selected from the group consisting of hydroxyl, methoxy and cyano; or
$R_2$ is $C_1$-$C_4$haloalkylsulfanyl, $C_1$-$C_4$haloalkylsulfinyl, $C_1$-$C_4$haloalkylsulfonyl, O($C_1$-$C_4$haloalkyl), or —C(O) $C_1$-$C_4$haloalkyl; or
$R_2$ is cyclopentyl or cyclohexyl which can be mono- or polysubstituted by substituents selected from the group consisting of halogen, cyano and $C_1$-$C_4$alkyl.

* * * * *